(12) United States Patent
Murphy et al.

(10) Patent No.: US 7,767,399 B2
(45) Date of Patent: Aug. 3, 2010

(54) PURIFICATION PROCESS FOR PLASMID DNA

(75) Inventors: Jason C. Murphy, Ambler, PA (US); David B. Boyd, Quakertown, PA (US); Adam Joel Kristopeit, North Wales, PA (US); Russel Jackson Lander, Lansdale, PA (US); Michael Albert Winters, Doylestown, PA (US)

(73) Assignee: Merck & Co., Inc., Rahway, NJ (US)

( * ) Notice: Subject to any disclaimer, the term of this patent is extended or adjusted under 35 U.S.C. 154(b) by 360 days.

(21) Appl. No.: 11/795,908

(22) PCT Filed: Jan. 27, 2006

(86) PCT No.: PCT/US2006/003015

§ 371 (c)(1),
(2), (4) Date: Jul. 24, 2007

(87) PCT Pub. No.: WO2006/083721

PCT Pub. Date: Aug. 10, 2006

(65) Prior Publication Data

US 2008/0138886 A1   Jun. 12, 2008

Related U.S. Application Data

(60) Provisional application No. 60/648,670, filed on Jan. 31, 2005.

(51) Int. Cl.
C12Q 1/68 (2006.01)
(52) U.S. Cl. .................................................. 435/6
(58) Field of Classification Search ............... 435/6
See application file for complete search history.

(56) References Cited

U.S. PATENT DOCUMENTS

| | | | |
|---|---|---|---|
| 4,923,978 A | 5/1990 | McCormick | |
| 5,561,064 A | 10/1996 | Marquet et al. | |
| 5,576,196 A * | 11/1996 | Horn et al. | 435/91.1 |
| 5,707,812 A | 1/1998 | Horn et al. | |
| 5,981,735 A | 11/1999 | Thatcher et al. | |
| 6,197,553 B1 | 3/2001 | Lee et al. | |
| 6,503,738 B1 | 1/2003 | Thatcher et al. | |
| 6,797,476 B2 | 9/2004 | Lander et al. | |
| 2002/0012990 A1 | 1/2002 | Lander et al. | |
| 2002/0197637 A1 | 12/2002 | Willson, III | |

FOREIGN PATENT DOCUMENTS

| | | |
|---|---|---|
| WO | WO 96/02658 | 2/1996 |
| WO | WO 96/36706 | 11/1996 |
| WO | WO 98/04730 | 2/1998 |
| WO | 98/16653 A1 | 4/1998 |
| WO | 99/58664 A1 | 11/1999 |
| WO | 00/09680 A1 | 2/2000 |
| WO | 01/07599 A1 | 2/2001 |
| WO | 01/46215 A1 | 6/2001 |
| WO | 02/42317 A2 | 5/2002 |
| WO | 2006/004611 A2 | 1/2006 |

OTHER PUBLICATIONS

Kahn et al., Biotechnology and Bioengineering, vol. 69, No. 1, pp. 101-106, Jul. 2000.*
Ferreira et al., TIBTECH, vol. 18, ppp. 380-387, Sep. 2000.*
Agerkvist et al., 'Selective flocculation with Chitosan in *Escherichia coli* disintegrates: effects of pH and nuclease treatment', Enzyme Microb. Technol. vol. 12, pp. 584-590 (1990).
Basha et al., 'Two simple non-enzymatic procedures to isolate high molecular weight DNA from fungi', Current Science, vol. 68, No. 6, pp. 587-588 (1995).
Biggs et al., 'Aggregate structures formed via a bridging flocculation mechanism', Chemical Engineering Journal, vol. 80, pp13-22 (2000).
Birnboim et al., 'A rapid alkaline extraction procedure for screening recombinant plasmid DNA', Nucleic Acid Res., vol. 7, No. 6, pp. 1513-1523 (1979).
Chamsart et al., 'The Impact of Fluid-Dynamic-Generated Stresses on chDNA and pDNA Stability during Alkaline Cell Lysis for Gene Therapy Products', Biotechnol. Bioeng., vol. 75, pp. 387-392 (2001).
Clemson et al. 'Optimizing alkaline lysis for DNA plasmid recovery', Biotechnol. Appl. Biochem. vol. 37, pp. 235-244 (2003).
Cumming et al.,'Flocculation of Esch. coli with cationic polymers: A method for the dose curve based on charge', Bioseparation, vol. 6, pp. 17-23 (1996).
Del Sal et al. 'The CTAB-DNA Precipitation Method: A Common Mini-Scale Preparation of Template DNA from Phagemids, Phages or Plasmids Suitable for Sequencing', BioTechniques, vol. 7, pp. 514-519 (1989).
Gustincich et al. 'A Fast Method for High-Quality Genomic DNA Extraction from Whole Human Blood', BioTechniques, vol. 11, pp. 298-301 (1991).
He et al., 'An Improved and Rapid Procedure for Isolating RNA-Free *Escherichia coli* Plasmid DNA', GATA, vol. 8, Issue 3, pp. 107-110 (1991).
Horn et al., 'Cancer Gene Therapy Using Plasmid DNA: Purification of DNA for Human Clinical Trials', Human Gene Therapy, vol. 6, pp. 565-573 (1995).

(Continued)

*Primary Examiner*—Gary Benzion
*Assistant Examiner*—Cynthia B Wilder
(74) *Attorney, Agent, or Firm*—Michael D. Yablonsky; Sheldon O. Heber

(57) ABSTRACT

Methods of isolating clinical-grade plasmid DNA from manufacturing processes, including large-scale fermentation regimes, are disclosed which encompass alternatives to two core unit operations common to plasmid DNA purification processes. The novel upstream and downstream purification processes disclosed herein provide for reduced production costs and increase process robustness. Either or both of the purification processes disclosed herein may be used in combination with additional purification steps known in the art that are associated with DNA plasmid purification technology.

23 Claims, 18 Drawing Sheets

OTHER PUBLICATIONS

Humphreys et al. 'A Simple Method For The Preparation of Large Quantities of Pure Plasmid DNA', Biochimica et Biophysica Acta, vol. 383, pp. 457-463 (1975).

Ishaq et al., 'Large-Scale Isolation of Plasmid DNA Using Cetyltrimethylammonium Bromide', BioTechniques, vol. 9, No. 1, pp. 19-24 (1990).

Kim et al., 'Removal of Cell and Cell Debris By Electrostatic Adsorption of Positively Charged Polymeric Particles', Flocculation in Biotechnology and Separation Systems, Ed. Y.A. Attia, Amsterdam: Elsevier, pp. 429-439 (1987).

Lee et al., 'Chemical flocculation as an alternative method to centrifugation in the collection of bacterial cells from growth medium for phospholipid isolation', Laboratory Practice, vol. 23, pp. 297-298 (1974).

Lerman, L.S., 'A Transition to a Compact Form of DNA in Polymer Solutions', Proc. Natl. Acad. Sci., USA, vol. 68, Issue 8, pp. 1886-1890 (1971).

Lis et al., 'Size fractionation of double stranded DNA by precipitation with polyethylene glycel', Nucleic Acids Res. vol. 2, Issue 3, pp. 383-389 (1975).

Lyddiatt et al., 'Biochemical recovery and purification of gene therapy vectors', Current Opinion in Biotechnology, vol. 9, pp. 177-185 (1998).

McGregor et al., 'Factors Affecting the Flocculation of Bacteria by Chemical Additives', Biotechnology and Bioengineering, vol. 11, pp. 127-138 (1969).

Minagawa et al.., 'Direct Observation of the Coil-Globule Transition in DNA Molecules', Biopolymers, vol. 34, pp. 555-558 (1994).

Nicoletti et al., Optimized PEG Method for Rapid Plasmid DNA Purification: High Yield from "Midi-Prep", BioTechniques, vol. 14, Issue 4, pp. 532-536 (1993).

Persson et al., 'Flocculation of Cell Debris For Improved Separation by Centrifugation', Flocculation in Biotechnology and Separation Systems, edited by Y.A. Attia, Elsevier Science Publishers B.V. Amsterdam, pp. 457-466 (1987).

Prazeres et al., 'Large-scale production of pharmaceutical-grade plasmid DNA for gene therapy: problems and bottlenecks', TIBTECH, Vol. 17, pp. 169-174 (1999).

Pulleyblank et al., 'A method for the purification of *E. coli* plasmid DNA by homogeneous lysis and polyethylene glycol precipitation', Molec. Biol. Rep., vol. 9, pp. 191-195 (1983).

Sadhu et al., 'A Procedure for the Preparation of RNA-Free Plasmid DNA', BioTechnique, vol. 6, Issue 1, pp. 115-116 (1988).

Shamlou, P.A., 'Scaleable processes for the manufacture of therapeutic quantities of plasmid DNA', Biotechnol. Appl. Biochem., vol. 37, pp. 207-218 (2003).

Strand et al., 'Screening of Chitosans and Conditions for Bacterial Flocculation', Biomacromolecules, vol. 2, pp. 126-133 (2001).

Tang et al., 'The fractal nature of *Escherichia coli* biological flocs', Colloids and Surfaces B: Biointerfaces, vol. 20, pp. 211-218 (2001).

Vorauer-Uhi et al., Flocculation: An alternative process to ion-exchange chromatography? (A scale-up study using recombinant human superoxide dismutase as model protein), Bioseparation, vol. 3, pp. 217-226 (1993).

Yeung et al., 'Fast and Economical Large-Scale Preparation of High-Quality Plasmid DNA', BioTechniques, vol. 15, Issue 3, pp. 149-150 (1993).

Yoshikawa et al., 'Nucleation and Growth in Single DNA Molecules', J. Am. Chem. Soc., vol. 118, pp. 929-930 (1996).

Braid et al., "Removal of PCR inhibitors from soil DNA by chemical flocculation", Journal of Microbiological Methods, 2003, vol. 52, pp. 389-393.

Milburn et al. "Selective flocculation of nucleic acids, lipids, and colloidal particles from a yeast cell homogenate by polyethyleneimine, and its scale-up", Enzyme and Microbial Technology, 1990, vol. 12, pp. 527-532.

* cited by examiner

A.
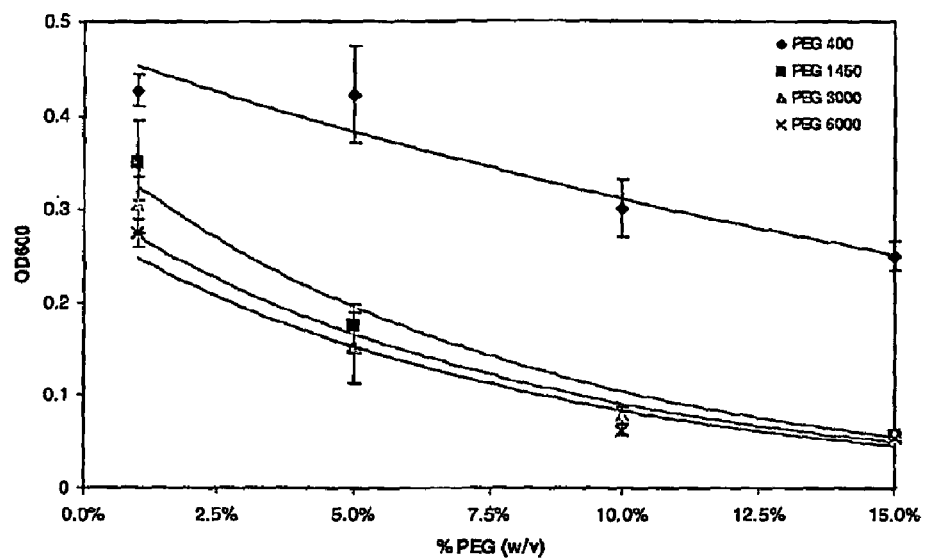
B.
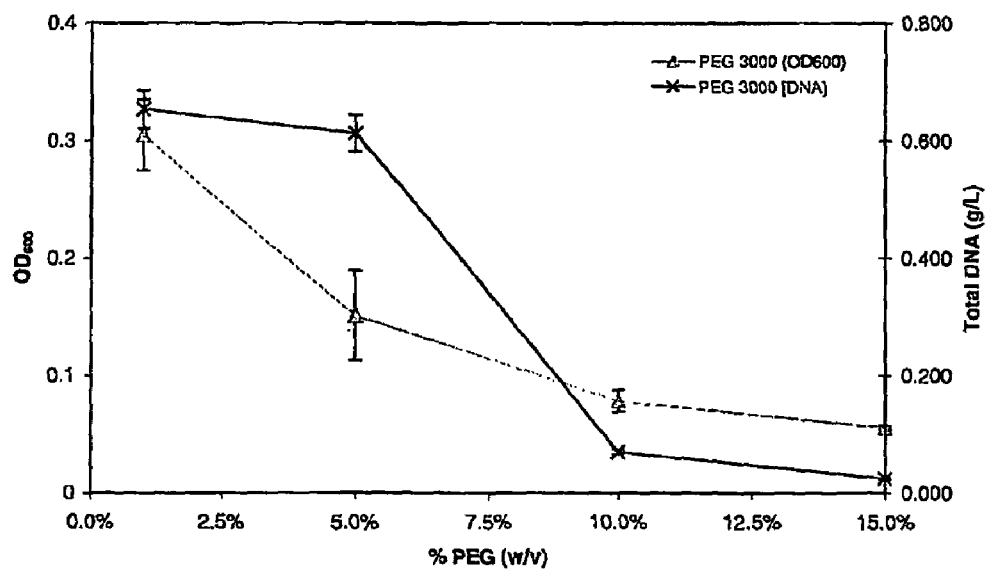
FIG. 4A & B

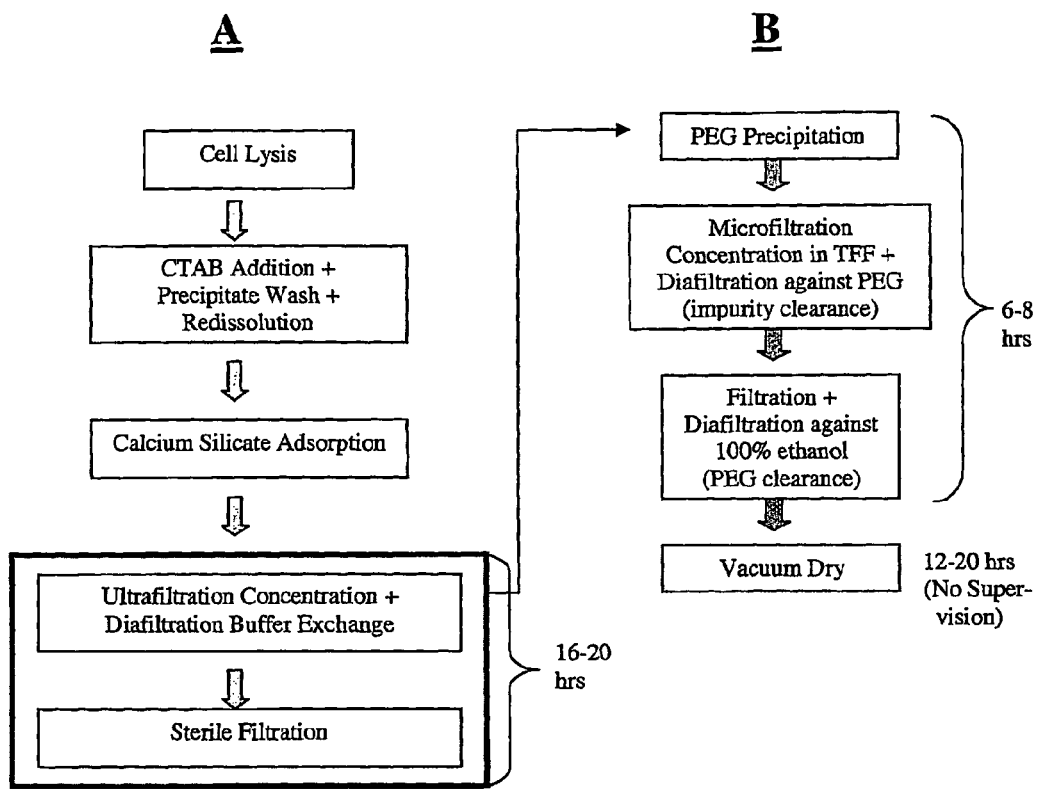
FIG.6A & B

A.
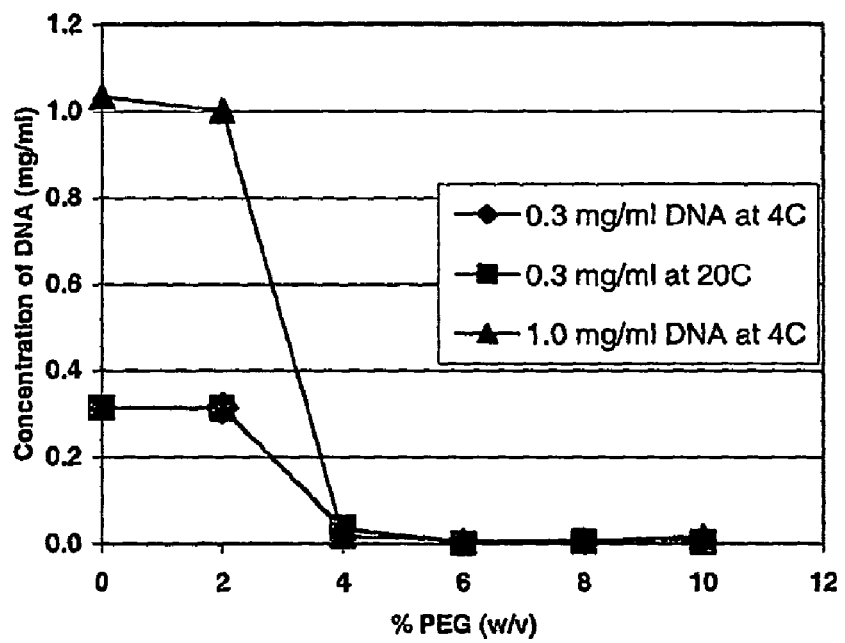
B.
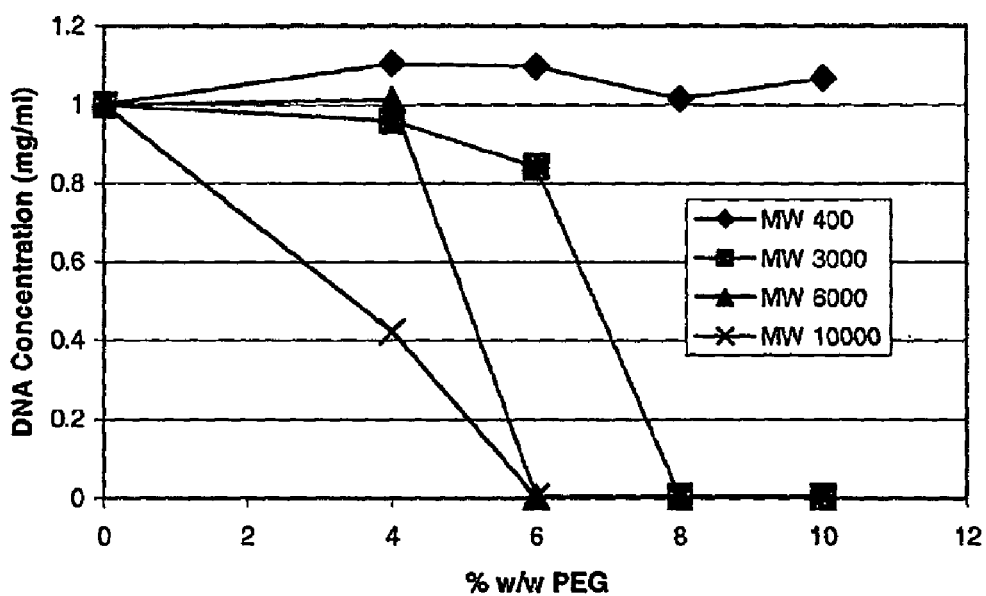
FIG.7A & B

A.
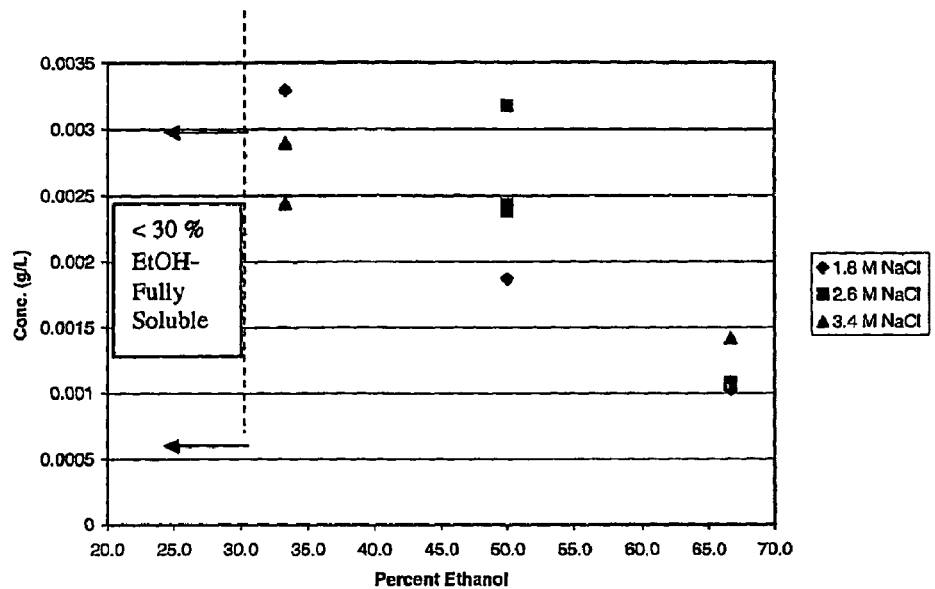
B.
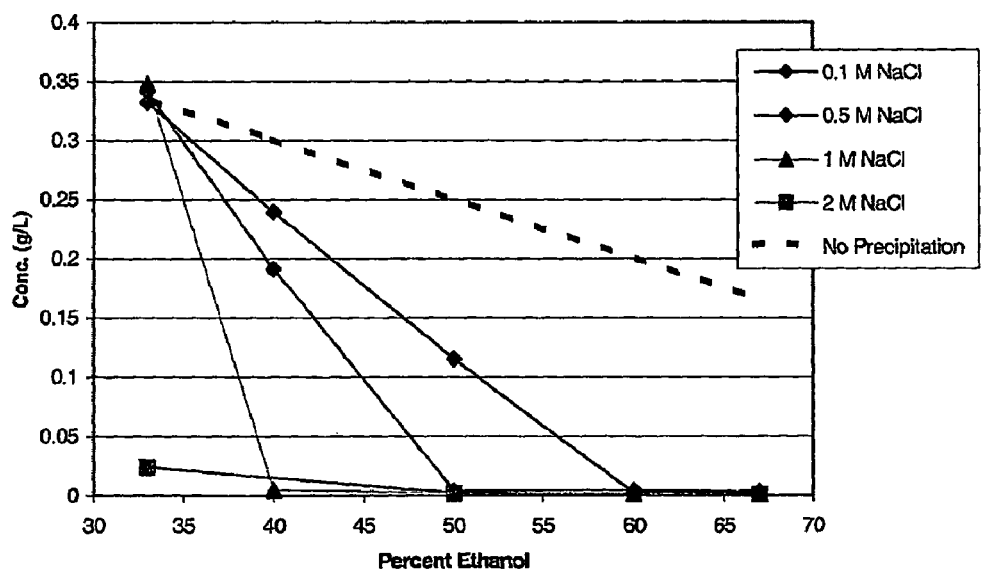
FIG. 9A & B

A.
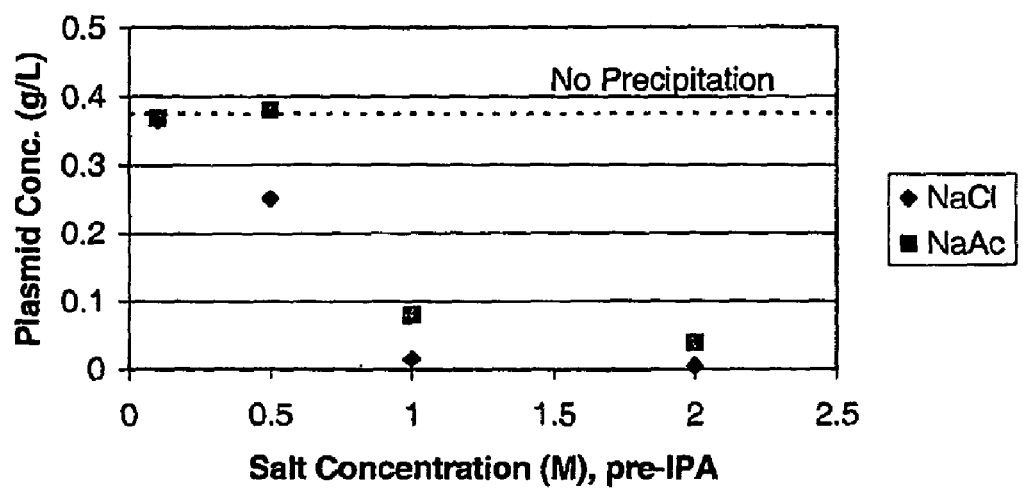
B.
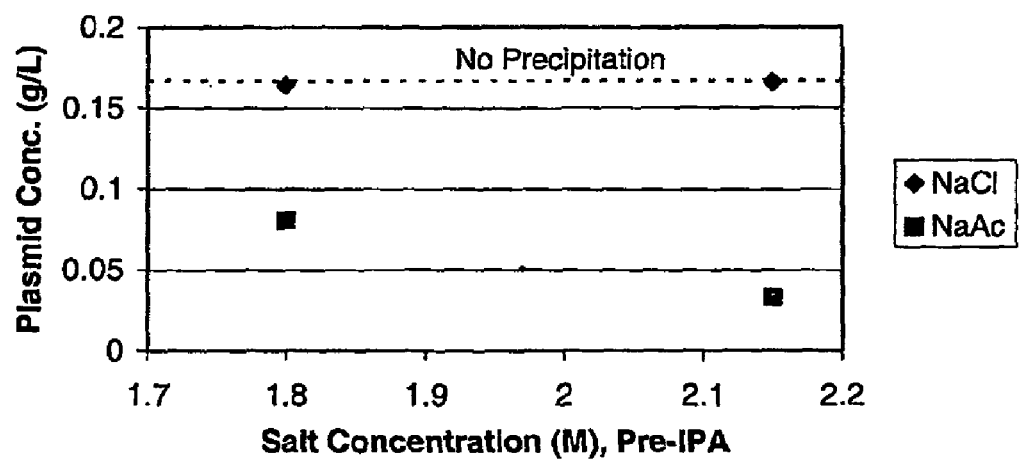
FIG.12A & B

A.
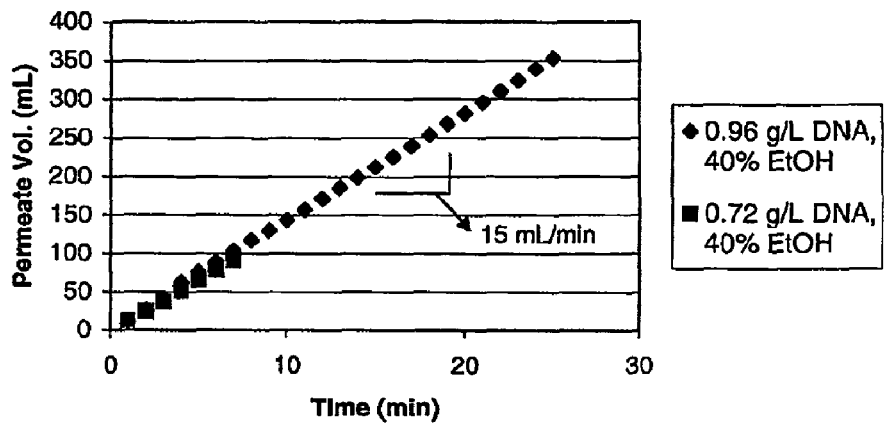
B.
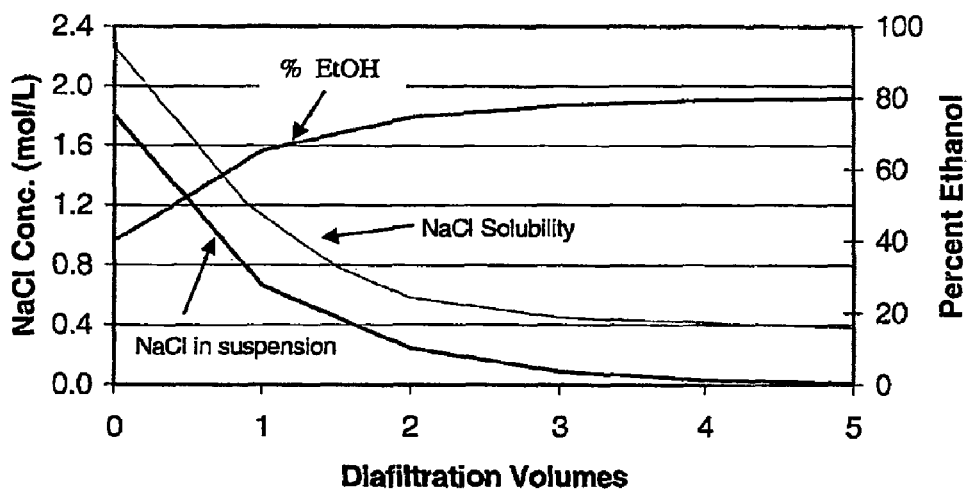
FIG. 14 A & B

A.
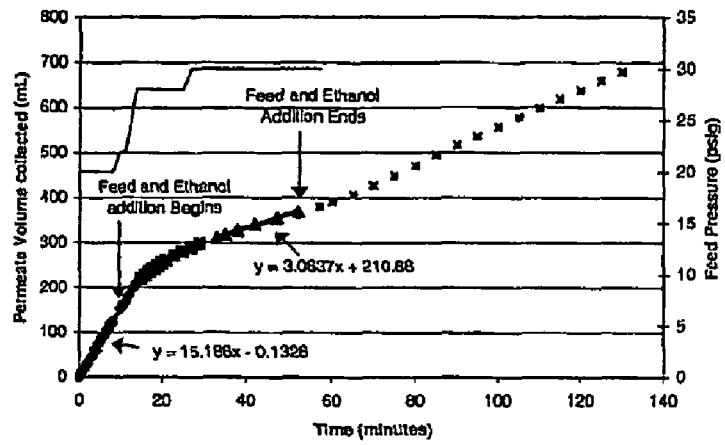
B.
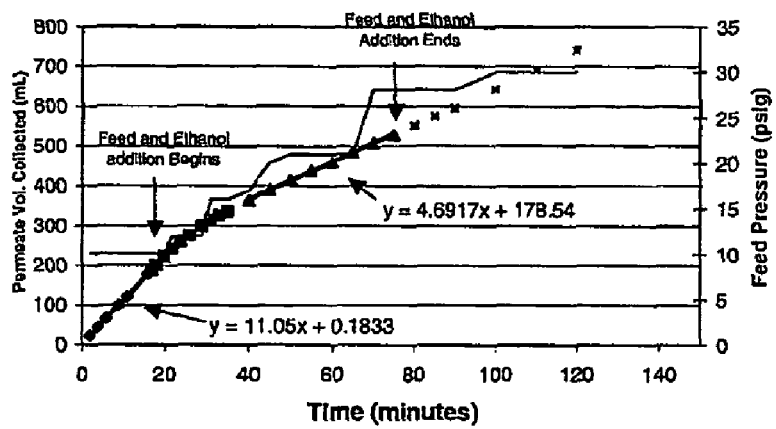
C.
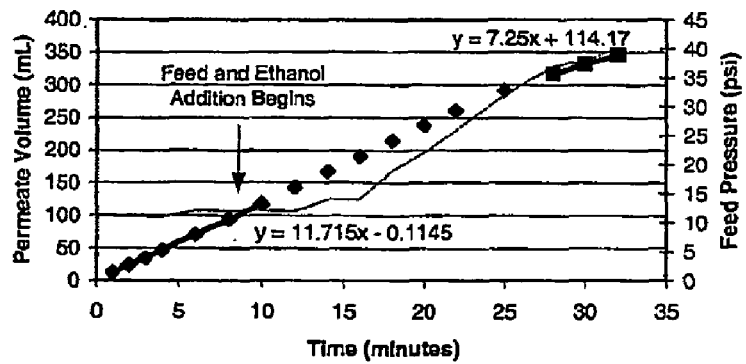
FIG. 15A, B & C

A.
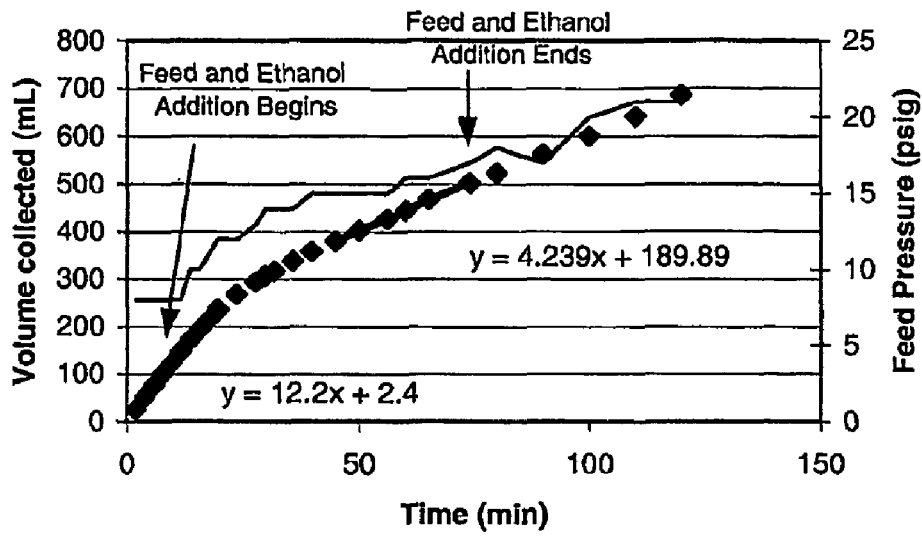
B.
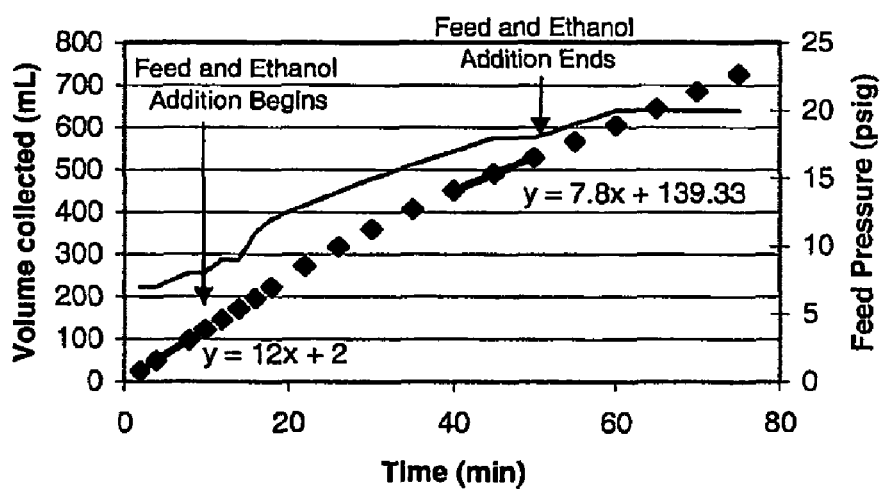
FIG. 16A & B

A.
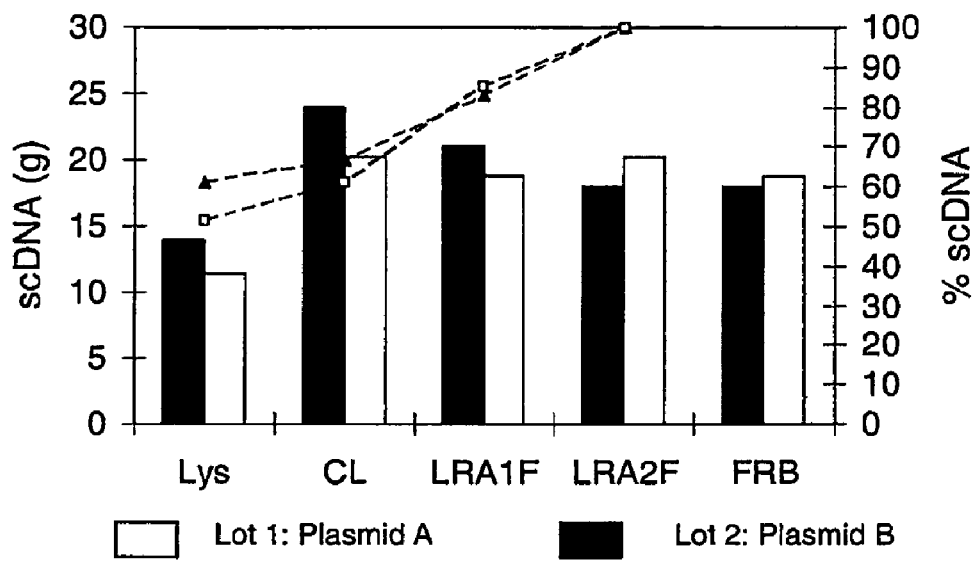
B.
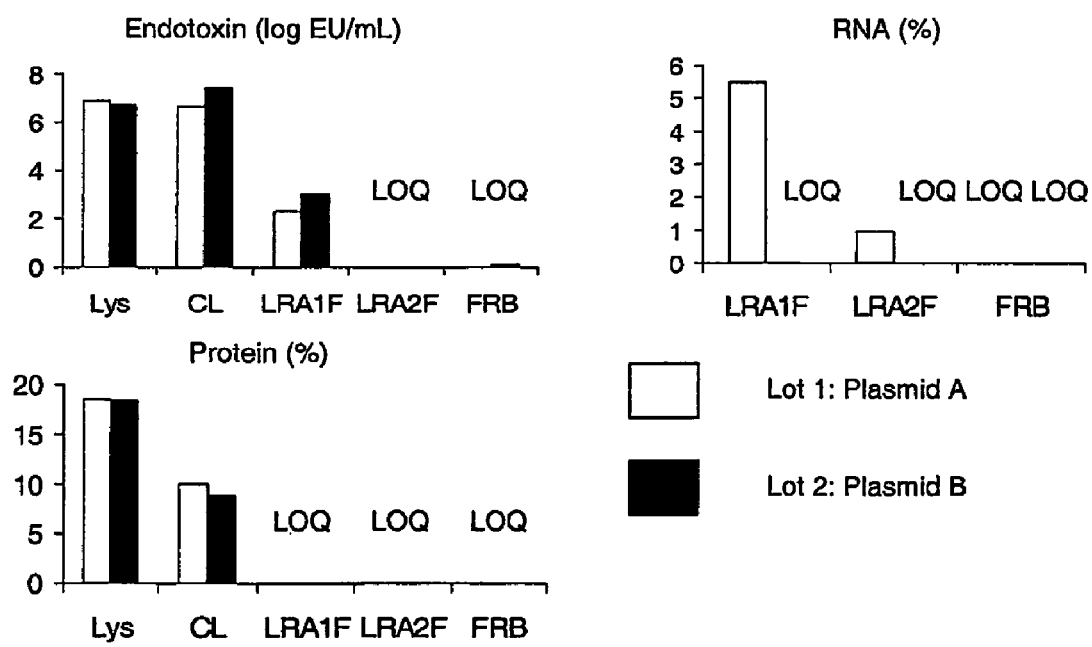
FIG. 17A & B

PURIFICATION PROCESS FOR PLASMID DNA

CROSS-REFERENCE TO RELATED APPLICATIONS

The present application is the §371 National Stage application of PCT International Application Ser. No. PCT/US2006/003015, having an international filing date of Jan. 27, 2006, which claims priority to U.S. Provisional Application No. 60/648,670, filed Jan. 31, 2005, now expired.

FIELD OF THE INVENTION

The present invention relates to methods of isolating clinical-grade plasmid DNA from manufacturing processes, including large-scale fermentation regimes, encompassing alternatives to two core unit operations common to plasmid DNA purification processes. The novel upstream and downstream purification processes disclosed herein provide for reduced production costs and increased process robustness. A novel upstream purification process described as part of the present invention comprises a two step lysis/lysate clarification process wherein a host cell lysate containing plasmid DNA is first generated and then clarified by flocculation of host cell debris. A novel downstream purification process described as part of the present invention encompasses precipitation of plasmid DNA from a host cell lysate enriched in said DNA and microfiltration of said precipitated DNA under a tangential flow filtration mode. Either or both of the purification processes disclosed herein may be used in combination with additional purification steps known in the art that are associated with plasmid DNA purification technology.

BACKGROUND OF THE INVENTION

Polynucleotide vaccines are an innovative approach for inducing protective immunity against specific diseases, both generating neutralizing antibodies as well as activating the more preferable cell-mediated immune responses (Montgomery, D. L. et al., 1993, *Cell Biol.* 169:244-247; Ulmer, J. B. et al., 1993, *Science* 259:1745-1749). Plasmid DNA comprising a gene encoding an antigen of interest and a promoter active in mammalian cells is administered to the body and internalized by muscle cells. The antigen DNA is transcribed and translated, and the expressed protein is transported to the cell surface for T-cell presentation. Preclinical immunogenicity and efficacy of DNA vaccines in disease models have been demonstrated for a number of infectious diseases (for a review, see Gurunathan, S. et al., 2000, *Ann. Rev. Immunol.* 18:927-974). Plasmid DNA has additionally been approved for gene therapy treatment, encompassing the administration of a functional gene into the body, delivery of said gene to a target cell, and expression of the therapeutic product with the intent to selectively modulate disease conditions. Thus, gene therapy represents an alternative for the prevention, treatment or cure of genetic defects. Many plasmid DNA-based gene therapy clinical trials have been initiated (for a review, see Mountain, A., 2000, *TIBTECH* 18:119-128; and Ferber, D., 2001, *Science* 294:1638-1642).

The manufacture and purification of large quantities of pharmaceutical-grade plasmid DNA is crucial to the applicability of both polynucleotide vaccine and gene therapy protocols. The potential number of human users for DNA vaccines or gene therapy treatments to combat disease, as part of either a prophylactic or therapeutic regimen is very large, creating a high demand for clinical-grade plasmid DNA.

Thus, high yield plasmid DNA production and purification processes are necessary to fully develop and exploit the advantages that both DNA vaccine and gene therapy treatment options have to offer (Shamlou, P. A., 2003, *Biotechnol. Appl. Biochem.* 77: 207-218). Despite prior investigations into small-scale plasmid DNA purification methodologies, scaling-up the manufacture and purification of clinical-grade plasmid DNA has been proven to be problematic (Prazeres, D. M. F. et al., 1999, *TIBTECH* 17:169-174). In addition, innovative large-scale manufacturing processes must balance optimization and economic concerns against demand and need for speed-to-market (Shamlou, 2003, supra). The present invention discloses a highly productive, scalable and reproducible process for the purification of plasmid DNA that reduces production costs and increases process robustness. The process discloses a new lysis and lysate clarification procedure which includes polymer flocculation of host cell debris. This new lysis and flocculation procedure may be combined with a novel, downstream polishing step encompassing precipitation of plasmid DNA (utilizing polyethylene glycol or alcohols) and subsequent microfiltration under a tangential flow filtration mode.

Chemical flocculation is commonly used to isolate bacterial cells from growth medium, representing a less expensive alternative to centrifugation (see, e.g., Lee, J. and C. V. Viswanathan, 1974, *Lab. Pract.* 23:297-298; Cumming, R. H., et al., 1996, *Bioseparation* 6:17-23). The mechanism of flocculation is complex, depending on many variables such as temperature, ionic environment, physiological age, flocculant, surface shear and material to be flocculated (McGregor, W. C. and R. K. Finn, 1969, *Biotechnol. Bioeng.* 11: 127-138). Only a few studies have analyzed this mechanism in relation to bacterial cell debris. Persson, I.-L. and B. Lindman ("Flocculation of Cell Debris for Improved Separation by Centrifugation," *Flocculation in Biotechnology and Separation Systems*, Ed. Y. A. Attia, Amsterdam: Elsevier, 1987, 429-439) used a combination of cationic polyelectrolytes, chitosan and polyethylene imine, to flocculate *E. coli* cell debris in laboratory and pilot plant studies. Positively charged polymeric particles have also been used to flocculate *E. coli* cell debris (Kim, C. W., et al., "Removal of Cell and Cell Debris by Electrostatic Adsorption of Positively Charged Polymeric Particles," *Flocculation in Biotechnology and Separation Systems*, Ed. Y. A. Attia, Amsterdam: Elsevier, 1987, 429-439). However, the ability of using a polymer flocculant to generate a clarified bacterial lysate for scalable process design has not been recognized.

The last step in purifying clinical grade plasmid DNA from microbial cell fermentation encompasses removing any residual, host cell-derived impurities and/or process contaminants carried over from prior upstream purification steps, as well as concentrating the final product and buffer exchange. The present invention utilizes well known methods of precipitating DNA with polyethylene glycol (see, e.g., L is, J. T. and R. Schleif, 1975, *Nucleic Acids Res.* 2:383-389; Sadhu, C. and L. Gedamu, 1988, *Biotechniques* 6:20-21; Yeung, M. C. and A. S. Lau, 1993, *Biotechniques* 15:381-382; and Horn, N. A. et al., 1995, *Hum. Gene Ther.* 6:565-573) or alcohols (see, e.g., Wallace, D. M., "Precipitation of Nucleic Acids," *Methods in Enzymology: Guide to Molecular Cloning Techniques*, Eds. S. L. Berger and A. R. Kimmel, 1987, 41-48; Serghini, M. A. et al., 1989, *Nucleic Acids Res.* 17:3604) in combination with microfiltration in a tangential flow filtration mode in a final polishing procedure to complete plasmid DNA purification. This process eliminates the high recirculation rates and large membrane areas required for ultrafiltration procedures commonly used in final polishing processes.

U.S. Pat. No. 5,561,064, issued to Marquet, M. et al. on Oct. 1, 1996, discloses a differential polyethylene glycol ("PEG") precipitation strategy utilized during the purification of pharmaceutical-grade plasmid DNA. Importantly, the first PEG precipitation step occurs after the production of a clarified lysate and prior to size exclusion of anion exchange chromatography.

U.S. Pat. No. 5,707,812, issued to Horn, N. et al. on Jan. 13, 1998, discloses the use of PEG as a condensation agent to enhance the binding of plasmid DNA to a chromatographic matrix, from which said DNA is subsequently eluted in a salt buffer containing PEG.

SUMMARY OF THE INVENTION

The present invention relates to methods of isolating pharmaceutical-grade plasmid DNA from microbial cells, wherein said methods represent component alternatives for plasmid DNA purification from manufacturing processes, including large-scale fermentation regimes, which result in reduced production cost and increased process robustness. The present invention further relates to two core unit operations common to plasmid DNA purification processes including a novel upstream (i.e., prior to and including host cell lysate clarification) and a novel downstream (i.e., post lysate clarification) purification step. More specifically, the upstream purification step disclosed herein includes a two-part lysis/lysate clarification procedure whereby a cell lysate is first generated from host cells containing a supercoiled plasmid DNA of interest, and said cell lysate is then clarified by flocculation to remove host cell debris. The novel downstream purification process of the present invention encompasses a final concentration/polishing procedure whereby a cell lysate enriched in supercoiled plasmid DNA via upstream and prior downstream purification steps is first precipitated to remove residual impurities and then subjected to microfiltration under a tangential flow filtration mode. These steps may be used in combination, in further combination with additional purification steps known in the art, and/or wherein at least one of the above-mentioned steps is omitted, preferably in combination with other methodologies known in the art, associated with DNA plasmid purification technology.

In one embodiment of the present invention, the methods described herein allow for clinical-grade DNA plasmid purification from microbial cells including, but not limited to, bacterial cells, plant cells, yeast and baculovirus, with *Escherichia coli* ("*E. coli*") being the preferred microbial host. The clinical-grade plasmid DNA purified by the methods described herein is extremely useful for administration to humans as a vaccine or gene therapy vehicle. While the methods of the present invention are specifically drawn to the purification of clinical-grade DNA plasmid purification from microbial cells, the application of said methods is not limited to purification from microbial cells. Thus, the present invention additionally relates to the isolation of clinical-grade plasmid DNA purified from mammalian cells, as well as the isolation and purification of alternative biomolecules (e.g., proteins) from various host cells (e.g., microbial or mammalian), using one or more of the novel steps disclosed herein.

The present invention relates to a method of purifying supercoiled plasmid DNA from a cell lysate of a large-scale microbial fermentation which comprises: (a) lysing microbial host cells containing supercoiled plasmid DNA, forming a host cell lysate; and (b) clarifying said lysate of step (a) by flocculating host cell debris. Lysis of host microbial cells can take place in the presence or absence of lysozyme. In one embodiment of the present invention, the host cell debris is flocculated with polyethylene glycol ("PEG"). The flocculant, including but not limited to PEG, used to clarify the cell lysate may be included as a component of the lysis buffer (e.g., a standard STET buffer) or added to the cell lysate after lysis has occurred. The flocculated host cell debris can be removed from the host cell lysate by, for example, settle and decant or centrifugation methods, including but not limited to continuous centrifugation, resulting in a clarified cell lysate. After the flocculated cell debris is removed, the supercoiled plasmid DNA in the clarified cell lysate is further purified away from remaining contaminants by downstream purification processes. Therefore, one embodiment of the present invention relates to a method of generating a clarified host cell lysate containing supercoiled plasmid DNA using the novel upstream purification process described herein.

The present invention further relates to a method of purifying supercoiled plasmid DNA from a cell lysate of a large-scale microbial fermentation which comprises: (a) lysing microbial host cells containing supercoiled plasmid DNA, forming a host cell lysate; (b) subjecting the host cell lysate of step (a) to an alkaline pH shift and subsequent neutralization; and (c) clarifying said pH-shifted cell lysate of step (b) by flocculating host cell debris. The alkaline-pH shift and subsequent neutralization step described herein help prepare the host cell lysate for the flocculation procedure; however, said pH shift can occur either prior to or after the addition of flocculant to said lysate. In one embodiment of the present invention, the pH of the initial cell lysate is shifted to an alkaline value (e.g., about pH 12-13) with the addition of a concentrated base solution, enabling denaturation of soluble host cell chromosomal DNA. The alkaline-shifted cell lysate is then neutralized to approximately the pH of the initial lysis buffer with the addition of a concentrated acid solution, preferably resulting in a cell lysate with a pH of between about 8-9. Thus, one embodiment of the present invention relates to a method of purifying supercoiled plasmid DNA from a cell lysate of a large-scale microbial fermentation which comprises: (a) lysing microbial host cells containing supercoiled plasmid DNA in a physiological buffer, forming a host cell lysate; (b) subjecting the host cell lysate of step (a) to an alkaline pH shift by raising the pH of said lysate to between about pH 12 and about pH 13 with the addition of base; (c) neutralizing the alkaline-shifted cell lysate of step (b) to approximately the pH of the physiological buffer in which the cells were lysed; and, (d) clarifying said pH-shifted, neutralized cell lysate by flocculating host cell debris with a flocculant, including but not limited to PEG.

The upstream lysis and lysate clarification technique of the present invention can be followed by a number of downstream purification processes, including but not limited to (i) precipitation of plasmid DNA from the clarified lysate using a cationic detergent, including but not limited to CTAB; (ii) dissolution of plasmid with a salt solution; (iii) adsorption of residual impurities onto hydrated calcium silicate; and, (iv) precipitation of purified plasmid DNA with polyethylene glycol or alcohol prior to final formulation of the clinical-grade plasmid preparation.

The present invention further relates to a novel downstream purification process for the isolation of clinical-grade plasmid DNA from a large-scale fermentation regime, representing a final concentration/polishing step that results in powdered plasmid DNA product. The downstream purification process of the present invention acts to remove residual impurities from a cell lysate that has been enriched in supercoiled plasmid DNA as a result of prior purification steps. Thus, the present invention relates to a method of purifying supercoiled plasmid DNA from a cell lysate of a large-scale microbial fermentation which comprises: (a) precipitating said supercoiled plasmid DNA; and, (b) concentrating said precipitated, supercoiled plasmid DNA by microfiltration under a tangential flow filtration mode. Precipitation of the supercoiled plasmid DNA in step (a) may occur by well known methods using polyethylene glycol or alcohols, including but not limited to ethanol, methanol and isopropanol. The microfiltration process of step (b) may directly replace ultrafiltration procedures commonly used in final concentration/buffer exchange procedures of plasmid DNA purification processes, minimizing recirculation rates, filter membrane areas, and total batch volume.

In one embodiment of the present invention, supercoiled plasmid DNA is precipitated from an enriched, clarified cell lysate (i.e., a host cell lysate that has been enriched in supercoiled plasmid DNA due to upstream and prior downstream purification process) with PEG as a first step in the novel downstream concentration/polishing purification process disclosed herein. Said precipitated plasmid DNA is then subjected to microfiltration operated under a tangential flow filtration mode. Thus, one embodiment of the present invention relates to a method of purifying supercoiled plasmid DNA from a cell lysate of a large-scale microbial fermentation which comprises: (a) precipitating said supercoiled plasmid DNA with PEG; and, (b) concentrating said precipitated, supercoiled plasmid DNA by microfiltration under tangential flow filtration mode. The microfiltration process of the present invention may be part of a stepwise filtration process. Thus, in one embodiment of the present invention, PEG-precipitated, supercoiled plasmid DNA, as described above, is concentrated via a stepwise filtration process comprising a first filtration step wherein microfiltration and subsequent diafiltration concentrates the precipitated plasmid DNA slurry and clears residual RNA and impurities. A second filtration step displaces the PEG within the DNA precipitate with ethanol and further concentrates the plasmid DNA, resulting in a final wet product of dehydrated plasmid DNA that the can be dried to obtain a fine powdered form. This second filtration step can take place in a filter dryer apparatus under a stirred-cell operation (e.g., a single-plate Nutsche filter dryer) permitting pressure filtration and vacuum drying. Therefore, the present invention relates to a method of purifying supercoiled plasmid DNA from a cell lysate of a large-scale microbial fermentation which comprises: (a) precipitating said supercoiled plasmid DNA with PEG; and, (b) concentrating said precipitated, supercoiled plasmid DNA using a stepwise filtration process comprising microfiltration in a tangential flow filtration mode. Said stepwise filtration process comprises: (a) a first filtration concentrating step comprising microfiltration under tangential flow filtration; (b) a first diafiltration step against a PEG-containing diafiltration buffer, wherein said diafiltration buffer contains a sufficient concentration of PEG, and optionally salt, to keep said supercoiled plasmid DNA precipitated; (c) a dehydration step wherein the precipitated, supercoiled plasmid DNA is partially dehydrated by the addition of ethanol; (d) a second filtration concentrating step; and (e) a second diafiltration step against 100% (v/v) ethanol. In a further embodiment, the second filtration and diafiltration steps of (d) and (e) occur in a filter dryer, including but not limited to a single-plate Nutsche filter dryer, under pressure filtration and in a stirred-cell mode.

The present invention further relates to a method of purifying supercoiled plasmid DNA from a cell lysate of a large-scale microbial fermentation which comprises: (a) precipitating said supercoiled plasmid DNA with alcohol, including but not limited to ethanol, methanol and isopropanol; and, (b) concentrating said precipitated plasmid DNA by microfiltration under tangential flow filtration. In one embodiment of this part of the present invention, said microfiltration concentration step is part of a stepwise filtration process which comprises: (a) a first filtration concentrating step comprising microfiltration under tangential flow filtration; (b) a first diafiltration step against an ethanolic solution, wherein the ethanol concentration of said solution is sufficient to keep said supercoiled plasmid DNA precipitated; (c) a second filtration concentrating step; and, (d) a second diafiltration step against 100% (v/v) ethanol. In a further embodiment, the second filtration and diafiltration steps of (c) and (d) occur in a filter dryer, including but not limited to a single-plate Nutsche filter dryer, under pressure filtration and in a stirred-cell mode.

As used interchangeably herein, the terms "clinical-grade plasmid DNA" and "pharmaceutical-grade plasmid DNA" refer to a preparation of plasmid DNA isolated from host cells which is of a level of purity acceptable for administration to humans for any known prophylactic or therapeutic indication, including but not limited to gene therapy and/or polynucleotide vaccination applications.

As used herein, "non-supercoiled plasmid DNA" refers to any DNA that is not supercoiled plasmid DNA, including any other form of plasmid DNA such as nicked, open circle, and linear, as well as host genomic DNA.

As used herein, "NTU" refers to—normalized turbidity units—. Turbidity is defined as particle "counts" which pass by the optical field of a submerged probe. Solution turbidity can be monitored with a laser-based, light-scattering device.

As used herein, "PEG" refers to—polyethylene glycol—.

As used herein, "$OD_{600}$" refers to—optical density at 600 nm—, a light scattering, spectrophotometric measurement of the number of cells/mL.

As used herein, "L.O.D." refers to—limit of detection—.

As used herein, "MW" refers to molecular weight in Daltons.

As used herein, "LRA™" refers to—Lipid Removal Agent™.

As used herein, "CTAB" refers to—hexadecyltrimethylammonium bromide—or—cetyltrimethylammonium bromide—.

As used herein, "hcCaSiO$_3$" refers to—hydrated, crystallized calcium silicate—.

As used herein, "IPA" refers to—isopropanol—.

As used herein, "MF" refers to—microfiltration—.

As used herein, "UF" refers to—ultrafiltration—.

As used herein, "STET buffer" refers to a buffer comprising approximately 50 mM Tris-HCl (~pH 7.0-9.0), about 50-100 mM EDTA, about 8% sucrose, and about 2% Triton®-X-100.

BRIEF DESCRIPTION OF THE DRAWINGS

FIGS. 4A and 4B demonstrate the effect of PEG molecular weight on the flocculation of E. coli cell debris. Cells were incubated in the presence of lysozyme and subjected to alkaline pH shift/acid neutralization. PEG stock solutions of different molecular weights (PEG 400-6000) were added to 10-mL aliquots of the lysate to achieve final PEG concentrations of between about 1.0% and 15.0%. The resulting mixtures were allowed to settle at room temperature for approximately 16 hours, and then $OD_{600}$ measurements were take (FIG. 4A). FIG. 4B shows a plot of $OD_{600}$ dependence and DNA concentration in solution for the study using only PEG 3000.

FIGS. 6A and 6B compare the general process flow diagrams of two final concentrating/polishing procedures of large-scale plasmid DNA purification processes.

FIGS. 7A and 7B depict DNA solubility in different PEG solutions. FIG. 7A shows a sharp drop in solubility of DNA in a solution of PEG 8000 when the PEG concentration is >2% w/v; however, there is no effect on DNA solubility due to solution temperature or DNA concentration for the range investigated. FIG. 7B shows that DNA is completely soluble in 400 MW PEG for the range studied; but as the MW increases, the critical mass of PEG necessary to precipitate DNA decreases.

FIG. 8 shows that after about 5 minutes, greater than 99% of the initial DNA is precipitated.

FIGS. 9A and 9B show solubility data for plasmid DNA in water-ethanol mixtures. Concentrations of NaCl are on an ethanol free basis. FIG. 9A shows that NaCl concentrations of 1.8 to 3.4 M have little effect on plasmid solubility. In FIG. 9B, lower concentrations of NaCl were studied with various concentrations of ethanol. The dashed line represents the plasmid concentration that would be present for each solution if no precipitation occurred.

FIGS. 12A and 12B depict plasmid solubilities in 25% (A) or 67% (B) IPA, with sodium chloride and sodium acetate salts.

FIG. 14A shows permeate volumes collected over time during microfiltration of precipitated plasmid. The initial concentration of DNA in the precipitated suspension is shown for each data set; and the initial suspension volume was 500 mL. Suspensions filtered easily at 15 mL/min, with no decrease in permeate flux over the course of the experiment and maintaining pressure readings of 10 psig throughout the filtration. FIG. 14B shows the ethanol and NaCl concentrations during diafiltration of the precipitated plasmid suspension with 80% v/v ethanol.

FIG. 15A-C show three attempts at continuous alcohol precipitation during microfiltration under tangential flow filtration ("TFF") conditions using Masterflex size 14 (5/16") tubing for feed and ethanol addition during filtration. FIG. 15A shows results from a continuous precipitation/microfiltration study using a 100 kD PES membrane and precipitating with 40% v/v ethanol. The feed flow-rate to the filtration cartridge was about 30 mL/min. After about 200 mL of permeate was collected, the flux decreased to about 20% of its initial value. FIG. 15B shows results from a continuous precipitation/microfiltration study using a 0.1 micron PVDF membrane and precipitating with 40% v/v ethanol. The feed flow-rate was also about 30 mL/min; however, a one minute lag time was incorporated between vessel and filter. FIG. 15C shows results from an experiment performed similar to that in FIG. 15B (0.1 µm PVDF membrane, one minute lag time); however, 50% ethanol, rather than 40% ethanol, was used to precipitate the plasmid DNA. The decrease in permeate flux was slightly reduced from the 40% v/v ethanol trial (FIG. 15B), but the pressure increase made continuing the filtration experiment for more than 30 minutes unfeasible.

FIGS. 16A and 16B show two attempts at continuous alcohol precipitation using microfiltration under TFF using HPLC tubing for feed and ethanol addition during filtration. FIG. 16A shows continuous precipitation/microfiltration using 40% ethanol concentration and no lag time.

FIGS. 17A and 17B show process yields (A) and impurity levels (B) of two purification runs using the plasmid DNA purification process described in Example 8. Purification of each plasmid began using 75-80 L of $OD_{600}$=70 E. coli lysates from 17.5-18.6 L fermentations. FIG. 17A compares the quantity of supercoiled plasmid DNA ("scDNA (g)") in grams and the percent of supercoiled DNA ("% scDNA") during various stages of the purification process: cell lysate ("Lys"); clarified lysate after flocculation of host cell debris ("CL"); DNA slurry after first calcium silicate batch adsorption and filtration ("LRA1F"); DNA slurry after second calcium silicate batch adsorption and filtration ("LRA2F"); and resuspended DNA that was powdered during PEG precipitation and subsequent microfiltration steps ("FRB"). FIG. 17B compares the quantities of endotoxin (log EU/mL), protein (%) and RNA (%) at the same stages of the purification process described in FIG. 17A.

DETAILED DESCRIPTION OF THE INVENTION

Figure 1:
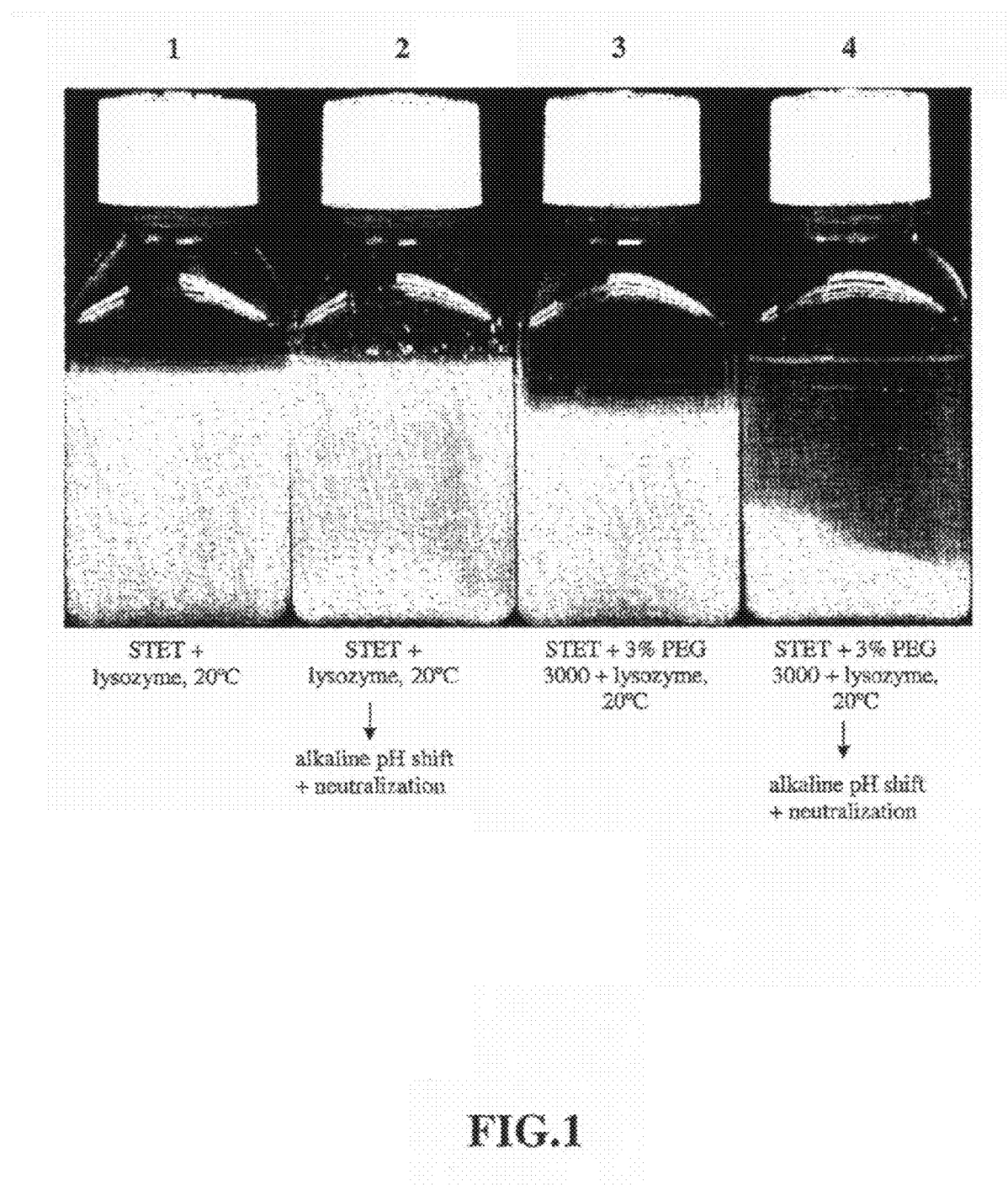
FIG. 1 shows *E. coli* cell lysates allowed to settle over a 2-day period. The lysate in Bottle 1 was generated by resuspending cells in a STET buffer (defined herein) and incubating with lysozyme (500 U/mL) at 20° C. The lysate in Bottle 2 is similar to that in Bottle 1, except after lysozyme incubation, first base was added to raise the pH to pH 12, and then acid was added to neutralize the pH. The lysate in Bottle 3 was generated by resuspending cells in a STET buffer containing 3% PEG 3000 and incubating with lysozyme at 20° C. The lysate in Bottle 4 is similar to that in Bottle 3, except after lysozyme incubation, base and acid were sequentially added, as described for Bottle 2, to induce an alkaline pH shift and subsequent neutralization. This figure illustrates the potential of PEG as a flocculant for cell debris from alkaline lysates.

The present invention relates to a scaleable methodology of purifying clinical-grade plasmid DNA resulting in reduced production costs and increased process robustness. It is oft considered that the principal unit operations for plasmid DNA purification include cell lysis, filtration (microfiltration/ultrafiltration) and chromatography. However, when isolating pharmaceutical-grade plasmid DNA in large scale, said identified, principal unit operations must be tailored to suit the process goals of both high quantity and high quality at minimum unit cost. For example, the expense of raw materials, such as resins and buffers, for multiple chromatographic steps has proven to result in a prohibitively high unit cost and poor capacity when applied to large-scale plasmid DNA purification processes. A recent disclosure, U.S. patent application Ser. No. 09/875,379 (U.S. publication number US2002/0012990), has identified an alternative plasmid DNA purification process that eliminates the requirement of relatively expensive chromatography steps while ensuring the isolation of grain quantities of plasmid DNA of clinical-grade quality (i.e., useful in at least human vaccination and human gene therapy applications). The present invention further expands upon the goal of generating economical, scaleable processes for the purification of clinical-grade plasmid DNA. To this end, the present invention identifies alternatives to two core operations of plasmid DNA purification processes, the generation of a clarified cell lysate and the final concentration/polishing of supercoiled plasmid DNA.

Therefore, the present invention relates to two core unit operations common to plasmid DNA purification processes including a novel upstream (i.e., prior to and including host cell lysate clarification) and a novel downstream (i.e., post lysate clarification) purification procedure. The disclosed upstream purification step includes a two-part lysis/lysate clarification procedure whereby a cell lysate is first generated from host cells, including but not limited to microbial cells, containing supercoiled plasmid DNA, and said cell lysate is then clarified by flocculation, removing host cell debris. The plasmid DNA of interest remains in the clarified lysate from which it is further purified via downstream processes. The disclosed downstream purification step of the present invention encompasses a final concentration/polishing step comprising a process whereby plasmid DNA is first precipitated from a solution enriched with said DNA, a result of prior purification steps, to aid in the removal of residual impurities remaining after said prior enrichment procedure, and subjected to microfiltration ("MF") in a tangential flow filtration mode. The purified plasmid DNA can then be dried to form a plasmid DNA product powder. As further described and exemplified herein, the upstream and downstream purification steps of the present invention are associated with additional purification processes, including but in no way limited to those purification methods disclosed in U.S. patent application Ser. No. 09/875,379 (supra). As such, it is within the scope of the present invention to utilize either or both of the purification steps described herein to formulate an overall scaleable purification process which results in the recovery of clinical-grade plasmid DNA. It is within the discretion of the skilled artisan to tailor a purification scheme required for a specific lot of plasmid DNA and of a quality required thereof. Various examples of utilizing the novel purification steps of the present invention are presented herein; however, in no way are these examples intended to limit the present disclosure.

One embodiment of the present invention relates to a method of purifying supercoiled plasmid DNA from a cell lysate of a large-scale microbial fermentation which comprises: (a) lysing microbial host cells containing supercoiled plasmid DNA, forming a host cell lysate; and, (b) clarifying said lysate of step (a) by flocculating host cell debris. In a further embodiment of the present invention, the host cell debris is flocculated with polyethylene glycol ("PEG"). Therefore, one embodiment of the present invention relates to a method of purifying supercoiled plasmid DNA from a large-scale microbial fermentation which comprises: (a) lysing microbial host cells containing supercoiled plasmid DNA, forming a host cell lysate; and, (b) clarifying said lysate of step (a) by flocculating host cell debris with PEG.

The microbial host cells are harvested from fermentation medium prior to lysis and resuspended in a sterilized, physiologically acceptable buffer (e.g., a standard STET buffer) to an appropriate dilution. One of skill in the art will recognize that optimal lysis conditions, in part, depend upon the concentration of microbial host cells within the lysis buffer. The host cell concentration ($OD_{600}$) in lysis buffer at which optimal lysis occurs can be easily determined, as demonstrated with *E. coli* host cells in Example 1, infra. Optimal lysis conditions can also be measured in terms of a dry cell weight ("DCW") dilution of host cells. An initial $OD_{600}$ of 70 may be preferred when lysing *E. coli* host cells by the novel lysis/lysate clarification process of the present invention (see Example 1). Alternatively, the inventors herein have determined that lysis of *E. coli* cells containing a supercoiled plasmid DNA of interest at a DCW of approximately 23 g/L also results in robust lysis. Lysis of said host cells generates a solution which includes, but is not limited to, the extrachromosomal supercoiled plasmid DNA to be purified, soluble host cell chromosomal or genomic DNA and host cell debris, e.g., insoluble host cell chromosomal or genomic DNA, cell membranes, organelles and modified solids. The cell lysis step of this embodiment of the present invention may occur in either the presence or absence of the enzyme lysozyme. In bacterial cells, lysozyme acts to break down the peptidoglycan cell wall of the bacterium, hydrolyzing the β-linkage between N-acetylmuramic acid (NAM) and N-acetylglucosamine (NAG) of the peptidoglycan layer. This exposes the inner cell membrane, leaving it vulnerable for further disruption, e.g., by detergent. Thus, lysozyme addition represents a gentle method of lysing bacterial cells, making mechanical disruption of larger plasmids less likely.

As taught in the Examples herein, the effect of lysozyme addition on the ultimate process yield is easily determined. Depending on the microbial, preferably bacterial, host cell chosen in which to amplify a supercoiled plasmid DNA of interest, one of skill in the art can empirically determine whether lysozyme addition will further aid in purification of said plasmid, e.g. ultimately maximizing the yield of purified plasmid DNA. In one embodiment of the present invention, host microbial cells, as exemplified in the Examples herein with *E. coli* cells, comprising a supercoiled plasmid DNA of interest are lysed in a standard STET buffer (e.g., 50 mM Tris-HCl, 100 mM EDTA, 2% v/v Triton®-X-100, 8% w/v sucrose, pH 8.2) in the presence of lysozyme. It is readily apparent to those skilled in the art that modifications to any basic buffer resuspension formula disclosed herein may be made and are suitable for use in the present invention. Thus, any basic buffer formula that does not substantially affect or alter the outcome of the present process is intended to be within the scope of the process described herein. However, it is preferred that the lysis step of the present invention takes place in the presence of a physiologically acceptable buffer comprising a chelator which effectively removes divalent cations such as $Mg^{++}$ and $Ca^{++}$ (e.g., EDTA), a non-ionic detergent (e.g., a Triton®-based detergent), and sucrose, especially if a downstream CTAB-based precipitation is contemplated. EDTA inhibits DNAse activity by associating with divalent metal ions which otherwise activate DNAse. EDTA continues to play a favorable role in CTAB-based, downstream precipitation steps since divalent metal ions will prevent complexation of plasmid with CTAB. Additionally, the CTAB concentration range in which to precipitate plasmid DNA is dependent upon both Triton® and DNA concentration (see U.S. patent application Ser. No. 09/875,379; supra). The buffer pH range may be adjusted according to the best results determined for the particular microbial strain; however, the preferred pH range is between about 7.0-9.0, with an optimal pH range of about 8.0-8.5.

In another embodiment of the present invention, complete cell lysis may include passage of host cells through a heat exchange apparatus as disclosed in PCT International Application Nos. PCT/US95/09749 (publication no. WO96/02658) and PCT/US96/07083 (publication no. WO96/36706), incorporated by reference herein, wherein said cells may or may not have been treated with lysozyme, preferably treated with lysozyme, prior to heat exposure. High-pressure homogenizers known to generate severe fluid dynamic forces are not preferable for the host cell lysis step of the present invention due to risk of damaging the supercoiled plasmid DNA and/or shearing of the genomic DNA to a size comparable to that of the desired plasmid. However, a mechanical cell lysis technique that has been found to protect DNA from shear damage, e.g., lysis in the presence of a compaction agent, small polycations that condense nucleic acids (as described in U.S. patent application Ser. No. 10/158,753, published as US20020197637 on Dec. 26, 2002) can be used.

A further aspect of the present invention includes subjecting the host microbial cell lysate generated in step (a), as described above, to an alkaline pH shift followed by neutralization to approximately the initial pH of said lysate, as dictated by the buffer in which the cells are originally lysed. Thus, in one embodiment of the present invention, supercoiled plasmid DNA is purified from a cell lysate of a large-scale microbial fermentation comprising the method of: (a) lysing host microbial cells containing supercoiled plasmid DNA, forming a host cell lysate; (b) subjecting the host cell lysate of step (a) to an alkaline pH shift and subsequent neutralization; and, (c) clarifying said pH-shifted lysate of step (b) by flocculating host cell debris. In a further embodiment, said pH-shifted lysate is clarified by flocculating host cell debris with PEG. The alkaline pH shift and subsequent neutralization of the host cell lysate may occur prior to the addition of the flocculant to the lysate. Alternatively, the flocculant may be present in the host cell lysate, either as a component of the initial lysis buffer or added after lysis has occurred, prior to the alkaline pH shift and neutralization step. In one embodiment of the present invention, the pH of the initial cell lysate is approximately between about pH 7.0 and about pH 9.0, preferably between about pH 8.0 and about pH 8.5, a result of the buffer in which the cells are initially suspended and lysed (e.g., a standard STET buffer consisting of 50 mM Tris-HCl, 100 mM EDTA, 2% v/v Triton®-X-100, 8% w/v sucrose, pH 8.2). The alkaline pH shift comprises shifting the lysate pH to a value which enables complete denaturation of the soluble host cell chromosomal DNA, e.g., approximately between about pH 12 and about pH 13. Over time, exposure of supercoiled plasmid DNA to this elevated pH will also cause plasmid to denature; however, due to the small size of plasmid DNA, it will re-anneal easily when conditions have neutralized. It is important that the lysate pH is not elevated above approximately pH 13, wherein plasmid DNA rapidly denatures and has increased sensitivity to shear damage. The pH of the lysate can be elevated by the addition of a concentrated base solution, including but not limited to 5 N sodium hydroxide ("NaOH"); and the pH-shifted cell lysate is then held at the elevated pH for a length of time to ensure denaturation of the chromosomal DNA (e.g., approximately 60 minutes). The pH of the cell lysate is then neutralized by the addition of a concentrated acid solution, including but not limited to a concentrated acetic acid solution (e.g., acetic acid with a normality of approximately between 1.7 to 2.5), decreasing the lysate pH to approximately that of the buffer in which the host cells were initially lysed.

Without being bound by theory, the pH shift described herein may be loosely compared to the classic alkaline lysis technique originally described by Birnboim and Doly (1979, *Nucleic Acid Res.* 7:1513-1523). The alkaline lysis method of Birnboim and Doly is well known for its ability to concurrently remove host cell genomic DNA and proteins by denaturation and then selectively precipitating the denatured material. The traditional alkaline lysis procedure uses a cell resuspension solution comprising Tris buffer plus glucose or fructose, to which a high base solution and sodium dodecylsulfate ("SDS") detergent is added for cell lysis. The high base selectively and completely denatures high molecular weight chromosomal DNA. The chromosomal DNA is then precipitated when the lysate is neutralized by the addition of 3 M potassium acetate (with acetic acid) at pH 5.5, retaining the plasmid DNA in the supernatant. Importantly, however, there are major drawbacks associated with use of this traditional alkaline lysis method for large-scale purification of plasmid DNA, including but not limited to large process volumes, the need for multiple process vessels, reported shear sensitivity of DNA at high pH, and high levels of sodium acetate (see Chamsart, S. et al., 2001, *Biotechnol. Bioeng.* 75:387-392). As explained above, the basic pH shift of this embodiment of the present invention is also important for denaturing chromosomal or genomic DNA present in the initial microbial cell lysate. Experiments described herein investigating the effect of high pH (e.g., pH 12) on supercoiled plasmid DNA (presented in Example 7, infra) demonstrate no damage to supercoiled plasmid DNA when exposed to pH 12 for over an hour at high impeller tip speeds. While the alkaline pH shift and subsequent neutralization step described herein removes a portion of the host genomic DNA from solution, complete clearance is not achieved, necessitating the subsequent flocculation procedure. As such, the basic pH shift and subsequent neutralization step of the present invention is performed to prepare the host cell lysate for the flocculation procedure, not to lyse the cells or clarify the lysate in itself. Thus, without being bound by any particular theory, the pH shift of the present invention has proven to be an important preparatory step for the subsequent flocculation of cell debris (described further infra; see Example 1).

Again, one embodiment of the present invention relates to a method of purifying supercoiled plasmid DNA from a cell lysate of a large-scale microbial fermentation which comprises: (a) lysing host microbial cells containing supercoiled plasmid DNA, forming a host cell lysate; and, (b) clarifying said lysate in step (a) by flocculating host cell debris. After the host cell lysate is generated, and optionally subjected to an alkaline pH shift and subsequent neutralization step as described above, the host cell lysate is flocculated to remove host cell debris (e.g., insoluble genomic host cell DNA, cell membranes, modified solids), generating a clarified lysate containing components which include, but are not limited to, supercoiled plasmid DNA and soluble chromosomal or genomic DNA. In one embodiment of the present invention, the flocculant which effectuates flocculation of host cell debris is a component of the initial lysis buffer. Alternatively, said flocculant can be added to the host cell lysate after lysis has occurred. Flocculation of the cell lysate by the method disclosed herein greatly enhances the separability of said microbial cell lysate. A low cut detergent precipitation step (e.g., CTAB) can be performed after flocculation to further decrease levels of soluble protein. Cell debris can settle from solution after flocculation (e.g., settle/decant), or it can be easily removed via centrifugation (e.g., 15,000×g, 15 minutes), including but not limited to continuous centrifugation. A polish filtration (e.g., using cellulosic or diatomaceous earth-based depth filters) can also be used, in addition to centrifugation, to remove residual solids from the lysate. After the flocculated cell debris is removed, the supercoiled plasmid DNA remaining in the lysate supernatant is then further purified away from other contaminants by downstream purification processes encompassing those known in the art (e.g., U.S. patent application Ser. No. 09/875,379; supra) and/or those novel downstream steps disclosed as part of the present invention.

Flocculation of host cell debris represents the aggregation of cellular particles, i.e. formation of cell debris agglomerates. A "flocculant" or "flocculation agent" is a material (e.g., a polymer) used to clarify particulate suspensions whereby said material induces the formation of agglomerates when added to the suspension. The flocculated material, representing insoluble particulate matter, can usually settle under gravity. However, large insoluble flocs (i.e., the aggregated material formed as a result of flocculation), including those cell debris flocs described herein, can be easily separated from solution by low speed centrifugation or simple filtration methods. Many different factors can affect the extent of flocculation, including but not limited to the surface charge, chemistry and physical characteristics of the material to be flocculated; flocculant adsorption rates and concentration; particle collision rates and concentration; and, suspension mixing conditions. Flocculation is thought to occur as a result of either the charge of the added flocculant ("charge neutralization") or its molecular weight ("bridging flocculation") (see Cumming, R. H. et al., 1996, *Bioseparation* 6:17-23). Flocculation via charge neutralization occurs by adhesion between a flocculation agent that carries an opposite charge from that of the material to be flocculated, causing either an overall neutralization of surface charge or a local reversal of charge and allowing effective particle collisions and increased floc growth. The efficiency of flocculation via a charge neutralization mechanism is not dependent upon flocculant molecular weight or its degree of polymerization. In comparison, aggregation of cellular material by bridging flocculation can occur with charged or non-ionic flocculants and is more dependent on flocculant molecular weight and/or degree of polymerization. Bridging flocculation is usually achieved by adding a high molecular weight polymer to a dispersion of colloidal particles. The flocculant adsorbs to the surface of more than one of the particles in a loops and tails conformation, thereby joining them together.

A number of different flocculants can be used to aggregate the host cell debris as described herein, including but not limited to synthetic (e.g., polyethylene glycol) or naturally occurring (e.g., chitosan) polymers, charged (e.g., anionic or cationic) or uncharged. Thus, in one embodiment of the present invention, a polymer flocculant is used to trigger cell debris aggregation in the host cell lysate generated as described above. It is important to consider both the characteristics of the material intended to be flocculated and subsequently discarded, as well as the material intended to be reserved (i.e., purified), when choosing the type of flocculant to affect cell debris agglomeration in the current process. In a plasmid DNA purification regime, an important issue to consider is that DNA is a negatively charged biomolecule, making positively charged flocculants, those most commonly known to flocculate bacterial cell debris, undesirable. A positively-charged flocculant will aggregate cellular debris along with the plasmid DNA intended to be purified. Therefore, it is preferable that a negatively-charged, and more preferable, that an uncharged polymer is selected to perform the flocculation step described herein. To this end, it is shown herein that polyethylene glycol ("PEG") is a non-toxic, cost-effective flocculant for lysates containing plasmid DNA. PEG is a non-ionic polymer composed of repeating units ($-O-CH_2-CH_2-$) to make a range of molecular weight polymers from 400 to greater than 15,000 (e.g., PEG polymers with molecular weights of up to 400,000 are commercially available). PEG is compatible with most organic solvents and has excellent water-solubility. PEG additionally has a proven safety profile as it is an ingredient in many over-the-counter medicaments and ointments. As shown in the Examples herein, PEG induces flocculation of host cell debris from a microbial lysate solution; however, the precise mechanism of this PEG-induced flocculation is not clear. It is possible that PEG acts via a traditional bridging flocculation mechanism whereby cell debris interacts directly with the polymer, adsorbing onto the polymer surface. Alternatively, PEG may exclude an unidentified component of the lysate from solution, wherein this excluded material then acts to flocculate host cell debris. Thus, PEG is herein identified as a flocculant of microbial host cell debris, wherein a "Rocculant" is defined as a material which induces the flocculation of host cell debris via either a direct or indirect mechanism.

It was shown by Lis and Schleif (1975; supra) that sufficient PEG concentrations can precipitate DNA; thus, if PEG is chosen as the flocculant in the methods described herein, it is important that the concentration of PEG used minimizes the possibility of plasmid DNA precipitation during the flocculation step of the present invention. As described above, since PEG is a non-ionic polymer, the extent of flocculation is likely dependent on both the molecular weight and the degree of polymerization of the polymer. One of skill in the art can empirically determine the most appropriate concentration and molecular weight of PEG to achieve the most efficient flocculation of host cell debris, keeping in mind a variety of factors, such as the size of the plasmid DNA to be purified and the particular host cell used for plasmid DNA amplification. As used herein, the most appropriate concentration and molecular weight of PEG polymer used to flocculate a particular host cell lysate represents that which results in the most efficient flocculation of said lysate, i.e., achieving a maximal amount of flocculated cellular debris combined with a minimal amount of plasmid DNA precipitation. For example, comparably efficient flocculation may be achieved by utilizing a high molecular weight PEG at a low concentration as when using a low molecular weight PEG at a high concentration. As such, it should be appreciated that there is a close interplay between PEG polymer concentration and molecular weight, and thus any specific PEG concentration and PEG molecular weight disclosed herein for flocculation purposes should be viewed as a guideline and not limiting to the invention as a whole.

In Example 1, screening studies were initially conducted to generally characterize the effects of PEG flocculation on the settling of bacterial cell debris. It was determined that PEG is a highly efficient flocculant of *E. coli* cell debris, especially after base/acid treatment of the *E. coli* cell lysate (e.g., pH shift from approximately pH 8.5 to approximately pH 12.5, and then back to approximately pH 8.5). Bacterial cell lysates from *E. coli* fermentation containing a plasmid DNA of interest were generated by four different methods (as shown in FIG. 1): (1) resuspending cells in STET buffer (described supra) and incubating with lysozyme at 20° C.; (2) resuspending cells in STET buffer, incubating with lysozyme at 20° C. and then subjecting lysate to base/acid treatment; and (4) resuspending cells in STET buffer containing 3% PEG 3000, incubating with lysozyme at 20° C. and subjecting lysate to base/acid treatment. Results from FIG. 1 demonstrate the highly efficient flocculation of cell debris in the pH-shifted, PEG-treated lysate (lysate #4) after material was permitted to settle over a 2-day period by gravity alone. The lysates shown in FIG. 1, and variations thereof, were further tested to characterize the observed PEG-induced flocculation (see FIG. 2). Aliquots of said lysates were incubated for 15 minutes and then centrifuged. Turbidity measurements (FIG. 3) demonstrate the action of PEG as a flocculant when added to a lysate subjected to base/acid treatment, showing a solution turbidity of 16 NTU after flocculating with 5% PEG 3000 (lysate #6), compared to 730 NTU of the control lysate (lysate #2). These results indicate that continuous centrifugation can be used as a clarification strategy to separate the flocculated material from the plasmid DNA-containing suspension, achieving sub 20 NTU clarity without using a polishing filtration to prepare a clarified lysate. Example 1 further demonstrates the effects of PEG concentration and molecular weight on flocculation of bacterial cell debris, describing how one of skill in the art can identify an appropriate PEG concentration and molecular weight when designing a strategy to achieve the most efficient flocculation of host cell debris. The effects of PEG concentration and molecular weight on flocculation of cell debris from host bacterial cells containing plasmid DNA were investigated using a rapid screening method based on settling performance of the cell debris. *E. coli* cells containing plasmid DNA were first lysed in the presence of lysozyme and subjected to a base/acid treatment as described above. Various PEG stock solutions (PEG 400-6000) were mixed into 10-mL aliquots of the lysates, resulting in PEG concentrations of between about 1% and 15% (w/v). The mixtures were then allowed to settle at room temperature for approximately 16 hours. The volume of settled solids and the turbidity of the supernatants ($OD_{600}$) were measured (see FIG. 4A). DNA concentration (as determined by AEX assay) and supernatant turbidity were further investigated using PEG 3000 as a flocculant (FIG. 4B). These results demonstrate, for example, that a PEG 3000 concentration range exists for which cell debris flocculates but DNA is not precipitated (see FIG. 4B). A similar plasmid DNA precipitation curve was also generated for PEG 6000 over a concentration range of between about 0% and 10%% (w/v) (see FIG. 5).

Therefore, in one embodiment of the present invention, supercoiled plasmid DNA is purified from a large-scale microbial fermentation by a method which comprises: (a) lysing host cells containing supercoiled plasmid DNA, forming a host cell lysate; and, (b) clarifying said lysate in step (a) by flocculating host cell debris with a polymer, including but not limited to polyethylene glycol ("PEG"). The host cells in step (a) can be lysed in the presence or absence of lysozyme, preferably in the presence of lysozyme, in a physiological buffer (e.g., a standard STET buffer as described above). Alternatively, harvested host cells can be lysed via passage through a heat exchange apparatus as disclosed in PCT International Application Nos. PCT/US95/09749 (supra) and PCT/US96/07083 (supra). The flocculation of the host cell debris in step (b) with a polymer, including but not limited to PEG, is performed such that a maximal amount of cell debris is aggregated into flocs, wherein said flocs contain a minimal amount of precipitated plasmid DNA. In one embodiment of the present invention, the host cell debris is flocculated with the addition of PEG, preferably of a molecular weight greater than about 1000, more preferably of a molecular weight between about 1450 and about 15,000, and most preferably of PEG 6000, to a final concentration of between about 2% and about 5% (w/v), more preferably between about 3% and about 4% (w/v), and most preferably of about 3.7% (w/v).

In a further embodiment of the present invention, prior to flocculation of host cell debris, and especially when PEG is chosen as the flocculant for the described lysate clarification process, the host cell lysate is subjected to an alkaline pH shift and subsequent neutralization step as described herein. Thus, said embodiment comprises a method of purifying supercoiled plasmid DNA from a cell lysate of a large-scale microbial fermentation comprising: (a) lysing host cells containing supercoiled plasmid DNA, forming a host cell lysate; (b) subjecting the host cell lysate of step (a) to an alkaline pH shift and subsequent neutralization; and, (c) clarifying said pH-shifted lysate of step (b) by flocculating host cell debris with a polymer, including but not limited to polyethylene glycol. In one embodiment of the present invention, the pH of the initial cell lysate is approximately between about pH 7 and about pH 9, preferably between about pH 8.0 and pH 8.5, a result of the buffer in which the host cells are initially suspended and lysed (e.g., a standard STET buffer consisting of 50 mM Tris-HCl, 100 mM EDTA, 2% v/v Triton®-X-100, 8% w/v sucrose, pH 8.2). The pH of the cell lysate is then shifted to a value which enables complete denaturation of the soluble chromosomal DNA, e.g., approximately between about pH 12 and about pH 13. As described above, the pH can be elevated with the addition of a concentrated base solution, including but not limited to 5 N NaOH; and the pH-shifted cell lysate is then held at the elevated pH for a period of time to ensure denaturation of the chromosomal DNA (e.g., 60 minutes). It is important, however, that the pH is not elevated to an extent such that plasmid DNA rapidly denatures and demonstrates an increased sensitivity to shear damage (i.e., approximately above pH 13). The pH of the cell lysate is then neutralized with the addition of a concentrated acid solution, including but not limited to a concentrated acetic acid solution (e.g., having a normality between about 1.7 and 2.5), decreasing the lysate pH to approximately that of the buffer in which the host cells were initially lysed. Thus, one embodiment of the present invention relates to a method of purifying supercoiled plasmid DNA from a cell lysate of a large-scale microbial fermentation which comprises: (a) lysing host cells containing supercoiled plasmid DNA in a physiological buffer, forming a host cell lysate; (b) subjecting the host cell lysate of step (a) to an alkaline pH shift by raising the pH of said lysate to between about pH 12 and about pH 13; (c) neutralizing the alkaline-shifted cell lysate of step (b) to approximately the pH of the initial physiological buffer in which the host cells were lysed, preferably between about pH 7 and about pH 9, more preferably between about pH 8.0 and pH 8.5; and, (d) clarifying said pH-shifted, neutralized host cell lysate by flocculating host cell debris with a polymer, including but not limited to polyethylene glycol ("PEG"). The physiological buffer (e.g., a standard STET buffer as described herein) in which the cells are lysed may or may not contain lysozyme. In the alternative, the alkaline pH shift and subsequent neutralization step can be performed after the addition of PEG to the cell lysate. For example, PEG may be present in the initial lysis buffer at a concentration which has been empirically determined to effectuate flocculation of host cell debris, wherein said PEG-containing cell lysate is then subjected to the alkaline pH-shift/neutralization step described herein in order to attain efficient flocculation of said cell debris (see Example 1). The present invention further relates to a method of purifying supercoiled plasmid DNA from a cell lysate of a large-scale microbial fermentation which comprises: (a) lysing host cells containing supercoiled plasmid DNA in a physiological buffer, forming a host cell lysate; (b) subjecting the host cell lysate of step (a) to an alkaline pH shift by raising the pH of said lysate to between about pH 12 and about pH 13; (c) neutralizing the alkaline-shifted cell lysate of step (b) to approximately the pH of the host cell lysate of step (a); (d) clarifying the cell lysate of step (c) by flocculating host cell debris with the addition of PEG 6000 to said lysate; and, (e) centrifuging said flocculated host cell debris of step (d), obtaining a supernatant which contains supercoiled plasmid DNA. In one embodiment of this part of the present invention, the physiological lysis buffer of step (a) is a standard STET buffer that contains lysozyme and has a pH of between about pH 7 to about pH 9, preferably a pH between about pH 8 and pH 8.5. In another embodiment, a concentrated PEG 6000 solution is added to said lysate to a concentration of about 3.7% (w/v). In a further embodiment of this part of the present invention, the PEG flocculant is fed to the alkaline-shifted, neutralized host cell lysate in step (d) under continuous centrifugation conditions, obtaining a pellet of flocculated cell debris with plasmid DNA remaining in the supernatant.

In one embodiment of the present invention, microbial host cells containing a supercoiled plasmid DNA are incubated in a physiological buffer in the presence or absence of lysozyme, preferably in the presence of lysozyme, and subjected to a basic pH-shift and subsequent neutralization step (as described above). This represents a novel lysis procedure which further prepares said microbial cell lysate for clarification by flocculating cell debris (e.g., insoluble genomic or chromosomal host cell DNA, cellular membranes and modified solids), retaining the supercoiled plasmid DNA in the supernatant. This lysis procedure can be performed at two times the concentration of a prior disclosed lysis process for purification of large-scale plasmid DNA, described in U.S. Pat. No. 6,197,553 issued to Lee and Sagar, which comprises a lysozyme lysis followed by rapid heating and cooling. Thus the novel lysis/lysate clarification process of the present invention allows for greatly reduced process volumes. In addition, the new lysis process described herein represents a simpler procedure than the earlier disclosed lysis technique. For example, it can be carried out in one tank, in comparison to the two large tanks required for the heat lysis procedure of U.S. Pat. No. 6,197,533, representing a large capital cost savings, and only requires mixing and addition of components, rather than complicated in-line heat exchangers. Additionally, the novel lysis and flocculation procedure of the present invention creates a feed from which cell debris is easily removed, including but not limited to settling of flocculated cell debris and decanting of the plasmid DNA-containing supernatant and centrifugation. Either batch or continuous centrifugation, whereby the plasmid DNA-containing supernatant is removed continuously as it is formed, can be used. The novel lysis and lysate clarification (via flocculation of host cell debris) technique of the present invention can be followed by downstream purification processes, including but not limited to (i) precipitation of plasmid DNA from the clarified lysate using cationic detergent, preferably CTAB; (ii) dissolution of plasmid with a salt solution; and, (iii) adsorption of residual impurities onto hydrated calcium silicate. A preferred downstream step remains the concentration and polishing of supercoiled plasmid DNA by either PEG- or alcohol-induced precipitation followed by microfiltration separation (see infra). Thus, another embodiment of the present invention relies on additional purification steps beyond the novel two-step lysis/lysate clarification process newly disclosed herein. A combination of process steps included as part of the present invention may include, for example, the following: (i) cell lysis, in the presence or absence of lysozyme, preferably in the presence of lysozyme; (ii) lysate clarification via flocculation of cell debris, including but not limited to PEG-induced flocculation; (iii) single or stepwise precipitation of plasmid DNA with detergent, such as CTAB; (iv) selective dissolution of plasmid with salt solution; (v) removal of remaining impurities by single or stepwise adsorption onto $hcCaSiO_3$; and, (vi) PEG- or alcohol-induced (e.g., ethanolic) precipitation of purified plasmid DNA, generating a stable bulk product from which concentrated formulation solutions can be readily prepared.

In one embodiment of the present invention, the methods described herein allow for clinical-grade plasmid DNA purification from microbial cells, including but not limited to bacterial cells, plant cells, yeast and baculovirus, with *E. coli* being the preferred microbial host. Thus, it is readily apparent to those skilled in the art that microbial fermentations other than *E. coli* fermentations are suitable for use in the present invention. Additionally, the methods of the present invention are not limited to purification of clinical-grade plasmid DNA solely from microbial cells and, thus, include purification of said plasmid DNA from other cell types, including mammalian cells, assuming that appropriate cell densities are attained. As such, the purification of clinical-grade plasmid DNA that has been amplified in either a mammalian culture system or from microbial fermentation is contemplated as part of the present invention. It will be within the purview of the skilled artisan to alter and optimize the specifics of the present invention to adjust to the specificities of different host cell types. For example, depending on the host cell chosen, it may be unnecessary to subject the initial cell lysate containing the amplified plasmid DNA to an alkaline pH shift and subsequent neutralization as a preparatory step to lysate flocculation. Lysozyme incubation alone and/or in combination with heat lysis may be sufficient to effectively prepare a cell lysate amenable to flocculation. One skilled in the art can easily adapt the harvest and lysis/lysate clarification processes disclosed in detail herein for purification from bacterial cells to purification from mammalian cells. For example, said skilled artisan would be aware that lysozyme addition, effective to aid in lysis of bacterial cells, would not be necessary for mammalian cell lysis. Instead, an alkaline pH shift as described herein would likely result in complete mammalian cell lysis. Similarly, purification of plasmid DNA from yeast cells would likely benefit from the substitution of lysozyme for yeast lytic enzyme (e.g., lytocase); although, yeast lytic enzyme may be unnecessary in favor of the alkaline pH shift disclosed herein. Thus, one of skill in the art, using the disclosures and detailed Examples herein, can easily alter the methods described as part of the present invention and apply it to whichever host cell type chosen in which to amplify the plasmid DNA. As such, while the application is written with a focus on purification of plasmid DNA from a large-scale "microbial fermentation," this terminology does not limit the invention to such. Thus, throughout the instant specification, the terminology "microbial fermentation" can be replaced to read on any type of host cell propagation or amplification process.

The plasmid to be isolated and purified by the methods disclosed herein can be any extrachromosomal DNA molecule, e.g., high copy or low copy number per cell, and virtually of any size. Thus, it is readily apparent to those skilled in the art that virtually any plasmid capable of amplification in a host cell, preferable a microbial host cell, can be isolated by the method of the present invention. The clinical-grade plasmid DNA purified by the methods described herein is extremely useful for administration to humans as a vaccine or gene therapy vehicle.

As described in detail above, the proposed use for the novel lysis/lysate clarification (via flocculation of microbial cell debris) process of the present invention is to purify clinical-grade plasmid DNA from large-scale microbial fermentation for use, for example, as polynucleotide vaccine or gene therapy vectors. The present invention further relates to a method of generating a clarified cell lysate containing supercoiled plasmid DNA comprising the novel lysis/lysate clarification process described herein. Importantly, the novel lysis/lysate clarification technology described herein can be extended to the purification of any recombinant biomolecule, including but not limited to proteins, monoclonal antibodies, fusion proteins, genomic DNA, RNA, lipids, and polysaccharides, from a microbial host. Thus, the lysis/lysate clarification process described herein, encompassing the (i) generation of a host cell lysate, (ii) an optional basic pH-shift and subsequent neutralization step, and (iii) clarification of said cell lysate by flocculation of host cell debris, may be extended to the production of any recombinant biomolecule using, for example, E. coli, other bacterial hosts, other microbial hosts (e.g., yeast) or mammalian cells. It will be within the purview of the skilled artisan to alter the lysis/lysate clarification (via flocculation) process of the present invention to adjust to the specificities both of a particular host cell types and of a particular product biomolecule to be purified. For example, exposure times to elevated pH conditions during the alkaline pH shift/neutralization step described herein, in addition to maximum pH stabilities, will need to be considered when designing an efficient and effective lysis/lysate clarification process related to that disclosed in the present invention for the purification of biomolecules other than plasmid DNA. The upstream purification step described herein which includes the alkaline pH shift will be an attractive purification step as long as the biomolecule to be purified is resistant to short term exposure to elevated pH and not precipitated by low levels of polyethylene glycol. Additionally, in processes where DNA is considered to be a contaminant (e.g., protein purification processes), PEG concentrations could be raised to precipitate DNA with the flocculated cell debris.

The large-scale microbial fermentations of the present invention may be cultivated in any liquid medium which is suitable for growth of the chosen microbial cell. Again, the present invention can easily be adapted to provide for methods of purifying plasmid DNA from large-scale mammalian cell culture, wherein any culture medium suitable for mammalian cell growth can be used. While the disclosed methodology is applicable to smaller fermentation or culture volumes, an especially useful aspect of the present invention is scaleability to large-scale cell fermentations or cultures. The term "large-scale," as used herein, is considered to be total cell fermentation volumes of greater than about 5 liters, or the cells harvested from a fermentation volume greater than about 5 liters. The large-scale fermentation methodology of the present invention is applicable to clinical size lots which represent, but are not limited to, approximately 300-2000 liter fermentations. For the upstream purification process described as part of the present invention, host cells containing a supercoiled plasmid DNA of interest are first harvested from culture medium to provide a cell paste or slurry. The goal of the harvest step is to concentrate and wash the cells for use in purification. Any conventional means to harvest cells from a liquid medium is suitable, including but not limited to centrifugation or microfiltration. For example, the harvest step may consist of a filtration process comprising (i) concentrating the cells using tangential flow filtration across a 500 kDa nominal molecular weight A/G Tech membrane, and (ii) diafiltering the concentrated cells with sterilized saline. Critical parameters in such a filtration process include transmembrane pressure, inlet pressure, crossflow rate, concentration factor and flux. In addition, the cells may be harvested utilizing continuous centrifugation. For a detailed description of a harvest procedure for bacterial cells, see Example section 9 infra.

The present invention further relates to a novel downstream purification process for the isolation of clinical-grade plasmid DNA from a large-scale fermentation regime, representing a final concentration/polishing step that results in powdered plasmid DNA product. As used herein, a downstream purification process, as it relates to plasmid DNA purification regimes, represents that which occurs after the initial host cell lysate has been clarified, a result of upstream purification processes (e.g., after the flocculation step of the upstream purification process described as part of the present invention). The plasmid DNA of interest remains in the clarified lysate after said upstream purification processes. The final concentration/polishing step of the present invention represents a downstream purification technique used to remove residual impurities from a cell lysate that has been enriched in supercoiled plasmid DNA as a result of both upstream and prior downstream processes. Said residual impurities may include host cell genomic DNA, cellular proteins remaining after prior purification processes, or process components present as a result of prior purification steps (e.g., detergents used to selectively precipitate plasmid DNA). It will be evident that the novel downstream purification step described as part of the present invention may by utilized with any of various combinations of earlier steps to finally purify supercoiled plasmid DNA away from remaining impurities while also concentrating said DNA and allowing for resuspension into a more workable buffer volume. Thus, as described and exemplified herein, the novel downstream purification step of the present invention will be associated with additional purification processes, including but in no way limited to those purification methods disclosed in U.S. patent application Ser. No. 09/875,379 (supra), as well as the novel upstream purification process disclosed as part of the present invention. It is within the scope of the present invention to include the novel downstream purification step described herein, representing a final concentration/polishing purification technique, when designing an overall scaleable purification process which results in the recovery of clinical-grade plasmid DNA. It is within the discretion of the skilled artisan to tailor a purification scheme required for a specific lot of plasmid DNA and quality required thereof.

Therefore, one embodiment of the present invention encompasses a downstream concentration/polishing step, wherein said downstream purification step relates to a method of purifying supercoiled plasmid DNA from a cell lysate of a large-scale microbial fermentation which comprises: (a) precipitating said supercoiled plasmid DNA; and, (b) concentrating said precipitated, supercoiled plasmid DNA by microfiltration ("MF") under tangential flow filtration mode ("TFF"). The use of precipitation with MP, rather than ultrafiltration ("UF"), to concentrate plasmid DNA as part of the final polishing step of plasmid DNA purification regimes is favored for a number of reasons. First, solution phase plasmid DNA is susceptible to shear damage when ultrafiltration processes are scaled-up to purify factory production quantities. Additionally, solution viscosities are reduced under microfiltration conditions, providing material that is more manageable at increased concentrations and allows decreased filter areas. This also permits greatly reduced volume requirements for diafiltration buffers. The supercoiled plasmid DNA to be precipitated in step (a) above will have been enriched in the cell lysate as a result of prior upstream and downstream processes, thus making the concentration/polishing purification technique of the present invention one of the last processes in the overall plasmid purification regimen. For example, in one embodiment of the present invention, supercoiled plasmid DNA is purified from a cell lysate of a large-scale microbial fermentation by a process including but not limited to the following steps: (i) cell lysis, in the presence or absence of lysozyme, preferably in the presence of lysozyme; (ii) lysate clarification, including but not limited to flocculation of cell debris by a polymer (e.g., PEG) as described herein, (iii) single or stepwise precipitation of plasmid DNA with detergent, such as a cationic detergent (e.g., CTAB); (iv) selective dissolution of plasmid DNA with a salt solution; (v) removal of remaining impurities by single or stepwise adsorption onto hcCaSiO$_3$; and, (vi) concentration of plasmid DNA via precipitation and microfiltering of said precipitated plasmid under tangential flow filtration mode. Of this list, the final concentration/polishing step of present invention represents unit operation (vi). The additional purification processes listed above are known to the skilled artisan or described, for example, in detail in the instant application and/or in U.S. patent application Ser. No. 09/875,379 (supra), incorporated by reference herein.

Prior to performing the final downstream concentration/polishing purification step of the present invention, supercoiled plasmid DNA will have been enriched in the host cell lysate as a result of prior upstream and downstream purification processes. For example, said final concentration/polishing purification step of the present invention can be incorporated within the multi-process plasmid DNA purification regime exemplified in U.S. patent application Ser. No. 09/875,379 (supra), resulting in large quantities of clinical-grade plasmid DNA in powdered form which, if desired, can be resuspended in a liquid formulation of choice. As an example, after clarification of a microbial host cell lysate (e.g., by an upstream purification process including but not limited to the novel upstream purification process described as part of the present invention), cationic detergent (e.g., cetyltrimethylammonium bromide or chloride as CTAB) may be used to precipitate the plasmid DNA from said clarified lysate. While CTAB is preferred for the selective precipitation of plasmid DNA, other monoalkyltrimethyl amino salts may be used, including but not limited to tetradecyltrimethylammonium bromide or chloride (TTA), alkyltrimethyl ammonium chloride, alkylaryltrimethyl ammonium chloride, dodecyltrimethylammonium bromide or chloride, dodecyldimethyl-2-phenoxyethylammonium bromide, hexadecylamine: chloride or bromide salt, dodecyl amine or chloride salt, and cetyldimethylethyl ammonium bromide or chloride. In addition, alternative quaternary ammonium compounds can be used to selectively precipitate plasmid DNA, such as monoalkyldimethylbenzyl ammonium salts (examples include alkyldimethylbenzyl ammonium chlorides and benzethonium chloride as BTC), dialkyldimethyl ammonium salts (commercial products include domiphen bromide as DB, didecyldimethyl ammonium halides, and octyldodecyldimethyl ammonium chloride or bromide), heteroaromatic ammonium salts (commercial products include cetylpyridium halides (CPC or bromide salt and hexadecylpyridinium bromide or chloride), cis-isomer 1-[3-chloroallyl]-3,5,7-triaza-1-azoniaadamantane, alkyl-isoquinoliniumbromide, and alkyldimethylnaphthylmethyl ammonium chloride (BTC 1110)), polysubstituted quaternary ammonium salts (commercially available products include, but are not limited to, alkyldimethylbenzyl ammonium saccharinate and alkyldimethylethylbenzyl ammonium cyclohexylsulfamate), bis-quaternary ammonium salts (product examples include 1,10-bis(2-methyl-4-aminoquinolinium chloride)-decane, 1,6-Bis[1-methyl-3-(2,2,6-trimethyl cyclohexyl)-propyldimethyl ammonium chloride]hexane or triclobisonium chloride, and the bis-quat referred to as CDQ by Buckman Brochures), and polymeric quaternary ammonium salts (including polyionenes such as poly[oxyethylene(dimethylimino)ethylene(dimethylimino)ethylene dichloride], poly[N-3-dimethylammonio)propyl]N-[3-ethylneoxyethylenedimethylammonio) propyl]urea dichloride, and alpha-4-[1-tris(2-hydroxyethyle)ammonium chloride).

Cationic detergent, including but not limited to CTAB, can be used to precipitate plasmid DNA from a flocculated and/or clarified host cell lysate in either a single or stepwise fashion; examples of which are disclosed in U.S. patent application Ser. No. 09/875,379 (supra). A stepwise precipitation process includes a low-cut and a high-cut precipitation step. The low-cut precipitation step can be used to help precipitate cell debris and non-supercoiled plasmid DNA from a cell lysate, leaving the supercoiled plasmid DNA of interest in the supernatant. In one embodiment of the present invention, said cell lysate may have been either flocculated but not yet cleared of the flocculated material or already clarified (i.e., post-flocculation and lysate clarification via, e.g., centrifugation of flocculated material). This low-cut precipitation can be followed by a high-cut precipitation step, whereby supercoiled plasmid DNA of interest is precipitated away from soluble impurities such as proteins, RNA and endotoxin. As described in detail in U.S. patent application Ser. No. 09/875,379 (supra), a stepwise addition of the cationic detergent CTAB may comprise feeding a 2% (w/v) CTAB solution to a clarified lysate in STET buffer, generating a first CTAB-induced precipitation from about 0.25% to about 0.35% (w/v) CTAB, more preferably from about 0.1% to 0.2% (w/v) CTAB, followed by a second CTAB-induced precipitation from about 0.40% to about 0.60%, said ranges best coinciding with the use of a standard STET lysis buffer (e.g., approximately 50 mM Tris-HCl, from about pH 7.0-9.0, about 50-100 mM EDTA, about 8% Sucrose and about 2% Triton®-X-100). It will be within the purview of the skilled artisan to alter precipitation ranges to adjust to any peculiarities of various buffer systems. Thus, in one embodiment of the present invention, a low-cut detergent precipitation step is used to further remove residual proteins and endotoxins from a DNA-plasmid containing cell lysate after flocculation (see Example 1, infra). More specifically, 2% (w/v) CTAB in 40 mM NaCl can be added to the cell lysate to a final concentration of about 0.15% over the span of about one hour to prevent hot spot filtration. If this low-cut detergent precipitation step is performed on a flocculated lysate before clarification of said lysate (i.e., before removal of the flocculated cell debris), said lysate can be subsequently clarified by centrifugation methods alone or in conjunction with a polishing filtration step. In a further embodiment of the present invention, a single, high-cut detergent precipitation step can be utilized as the first step in the overall downstream plasmid DNA purification process (i.e., after lysate clarification). Thus, in one embodiment, CTAB is added to a flocculated and/or clarified lysate generated by the novel upstream purification process of the present invention to a final concentration of between about 0.40% and about 0.60%, wherein said ranges coincide best with the use of a standard STET lysis buffer as described above. Again, it will be within the purview of the skilled artisan to alter said precipitation range to adjust to any peculiarities of various buffer systems. Thus, either before or after the removal of host cell debris flocs (e.g., by either settle/decant or centrifugation methods, alone or in conjunction with a polishing filtration), cationic detergent (e.g., CTAB) can be added by feeding a 2% (w/v) detergent solution to a cell lysate to a final concentration such that either residual proteins and endotoxins (low-cut step) and/or supercoiled plasmid DNA (high-cut step) are precipitated, wherein both detergent precipitation steps function to further separate the plasmid DNA from impurities. A single or stepwise cationic-based detergent step will be associated with a filtration step to generate a filter cake precipitate (containing supercoiled plasmid DNA) for subsequent salt dissolution (as described in U.S. patent application Ser. No. 09/875,379; supra). Salt dissolution of the recovered filter cake (comprising supercoiled plasmid DNA) is performed in a buffer solution of optimal ionic strength and composition. The concentration is determined by measuring the concentration of supercoiled plasmid in solution at various salt increments or, indirectly, by measuring the solution viscosity.

Another prior downstream purification technique which may be used to help generate the plasmid DNA-enriched cell lysate from which supercoiled plasmid DNA will be purified via the novel concentration/polishing step described as part of the present invention is the adsorption of remaining impurities in a single or stepwise fashion onto hydrated, crystallized calcium silicate ($hcCaSiO_3$), such as synthetic hydrated calcium silicate LRA™ (Advanced Minerals Corporation, Lompoc, Calif. 93438). As described in detail in U.S. patent application Ser. No. 09/875,379 (supra), addition of $hcCaSiO_3$ to a microbial host cell lysate results in adsorption of residual impurities away from the supercoiled plasmid DNA. Hydrated calcium silicate binds a variety of impurities, including but not limited to detergent (e.g., CTAB, Triton®), endotoxin, genomic DNA, plasmid degradates, proteins and RNA. The precise amount of $hcCaSiO_3$ required for addition is governed by (i) the amount of impurities present; (ii) the buffer conditions (e.g., salt concentration); (iii) the amount of total DNA in solution; (iv) the volume of solution; and, (v) perhaps other variables which include the temperature and the type of salt utilized throughout the purification process. Thus, it will be evident that the amount of $hcCaSiO_3$ to be added during a specific purification run may vary. It is anticipated that the amount of $hcCaSiO_3$ to be added would be in the range of up to about 200 grams $hcCaSiO_3$/grams of total DNA, depending upon the conditions described above as well as potential differences depending on the lot of $hcCaSiO_3$ available for that specific run. Example section 8 gives guidance in a range from about 8 to about 200 grams $hcCaSiO_3$/grams of total DNA During a typical plasmid DNA purification run, the preferable range of added $hcCaSiO_3$ is between about 125 and 200 grams $hcCaSiO_3$/grams of total DNA, and more preferably between about 30 and 70 grams $hcCaSiO_3$/grams of total DNA. The inventors have found that a typical plasmid purification run requires between about 30-70 g LRAII/g total DNA. But again, the conditions for $hcCaSiO_3$ adsorption may scale upward or downward in relation to the conditions explained above, thus potentially necessitating addition of $hcCaSiO_3$ at a higher end of the range, toward 200 grams $hcCaSiO_3$/grams of total DNA. For example, a higher concentration of NaCl increases the capacity of LRA™ for DNA and other impurities. Therefore, it will be useful in some instances to consider higher salt concentrations, which should decrease the amount of the $hcCaSiO_3$ needed. It is expected that useful salt concentrations may be in a range, for example with NaCl, of up to about 5 M NaCl. As noted above, the adsorption of impurities onto $hcCaSiO_3$ may occur in a single of stepwise fashion. As described in Example 8 herein, a stepwise LRA adsorption process wherein the first adsorption step is combined with the salt dissolution of detergent-induced, precipitated plasmid DNA leads to a more robust redissolution. A second stage calcium silicate batch adsorption is then used in order to (a) minimize the amount of calcium silicate during resuspension, and (b) to act as an initial polishing step for the reduction of residual host-cell genomic, open circular plasmid and linear plasmid DNA.

With the generation of a cell lysate enriched in supercoiled plasmid DNA as a result of a variety of both prior upstream and downstream purification techniques, some type of concentration and final buffer exchange step is generally performed, representing the final product purification step of the overall process. This final concentration/polishing step ensures that essentially all residual impurities are removed from the plasmid DNA-containing solution and concentrates said plasmid DNA into a physiologically acceptable buffer at an desired product concentration. The present invention relates to the disclosure of a novel final concentration/polishing step that includes precipitation of plasmid DNA by well known methods using a DNA precipitant (e.g., polyethylene glycol, alcohols, PEI, polyamines, cationic detergents, crowding polymers, triplex agents and other organic agents) in combination with microfiltration in a tangential flow filtration mode. The ultimate goal of the novel concentration/polishing step described herein is the purification of plasmid DNA resulting in a powder formulation. However, liquid formulations are also attainable when said powdered product is resuspended in a desired liquid. This portion of the present invention solves scale-up problems that often plague large-scale plasmid DNA purification regimens. The use of plasmid DNA precipitation with, for example, either PEG or alcohol in combination with microfiltration concentration can directly replace final ultrafiltration procedures commonly used in final buffer exchange/concentration procedures for plasmid DNA purification processes. Ultrafiltration often requires high recirculation rates and large membrane areas providing minimal contaminant clearance. A batch alcohol precipitation-based batch process disclosed in a prior application, U.S. patent application Ser. No. 09/875,379 (supra), avoided these limitations, drastically decreasing the necessary membrane area and recirculation rates and creating a powdered DNA to minimize bulk storage requirements. However, batch alcohol precipitation requires large solvent ratios and excessive solvent waste disposal, impractical for large-scale solvent precipitation. The microfiltration based process of the present invention greatly reduces the membrane area that is required for an alternative liquid bulk ultrafiltration approach; and when used in conjunction with alcohol precipitation, a continuous solvent recovery system avoids difficulties that often accompany batch type filtration of alcohol precipitated product.

Therefore, the present invention relates to a method of purifying supercoiled plasmid DNA from a cell lysate of a large-scale microbial fermentation which comprises: (a) precipitating said supercoiled plasmid DNA; and, (b) concentrating said precipitated, supercoiled plasmid DNA by microfiltration under tangential flow filtration mode. In one embodiment of the present invention, said supercoiled plasmid DNA is precipitated in step (a) using a precipitant selected from the group consisting of polyethylene glycol (PEG) and alcohol (including but not limited to ethanol, methanol and isopropanol). Additional DNA precipitants which may be used to precipitate the supercoiled plasmid DNA in step (a) include, but are not limited to, PEI, polyamines, cationic detergents, crowding polymers, triplex agents and other organic solvents.

Therefore, the present invention relates to a method of purifying supercoiled plasmid DNA from a cell lysate of a large-scale microbial fermentation which comprises: (a) precipitating said supercoiled plasmid DNA with polyethylene glycol; and, (b) concentrating said precipitated, supercoiled plasmid DNA by microfiltration under tangential flow filtration mode. Precipitation of plasmid DNA by PEG is rapid and gentle, causing little damage to the DNA (Humphreys, G. O. et al., 1975, *Biochim. Biophys. Acta.* 383:457-463). As discussed previously herein, PEG precipitation of plasmid DNA is highly dependent on the concentration of the polymer in the DNA solution (see Humphreys et al., 1975, supra). Addition of PEG to a cleared cytoplasmic extract to a final concentration of 10% was shown to precipitate all the plasmid DNA contained within said extract, leaving some RNA and most proteins in solution (Pulleyblank, D. et al., 1983, *Molec. Biol. Rep.* 9:191-195). Lis and Schlief (1975, supra) demonstrated the separability of DNA molecules of different molecular weights with PEG. After determining that higher molecular mass DNA precipitated preferentially at a lower PEG concentration, they developed a size fractionation method for plasmid DNA molecules based on precipitating said molecules using varying PEG concentrations. PEG promotes condensation of DNA molecules from an elongated coiled state to a compacted globular state (Minagawa, K et al., 1994, *Biopolymers* 34:555-558), wherein said DNA molecules undergo a first-order phase transition (Yoshikawa, K. et al., 1996, *J. Am. Chem. Soc.* 118:929-930). At low concentrations of PEG, DNA molecules stay as elongated coils, while at high concentrations, they contract into small globule conformations. Without being bound by any particular theory, PEG is thought to precipitate DNA by volume exclusion such that as PEG is added to the plasmid-containing solution, it interacts with the water molecules rather than with the DNA. DNA will not interact with the PEG because of its negative surface charge. As more PEG is added, this exclusion effect forces more and more DNA into small pockets until, eventually, the local DNA concentration exceeds the limit of solubility. As shown in the Examples herein, the concentration of PEG required for complete precipitation is mainly a function of salt concentration, PEG molecular weight, product impurities and plasmid size.

As noted above, the mechanism of PEG-induced precipitation of plasmid DNA is highly dependent upon both the concentration and molecular weight of the PEG precipitant in the plasmid DNA-containing solution. As described in the Examples section infra, PEG molecular weights from 400 to 10,000 Da were tested for the ability to precipitate plasmid DNA out of solution (FIG. 7B). Said studies demonstrate that DNA is completely soluble in 10% (w/v) PEG 400; but as the molecular weight of PEG increases, the critical mass of PEG necessary to precipitate DNA decreases. Thus, while the purification processes exemplified herein utilize either PEG 6000 or PEG 8000 as the precipitant for this part of the present invention, one of skill in the art will appreciate that virtually any molecular weight PEG can be used to effectively precipitate plasmid DNA, especially between the PEG MW range of about 3,000 to about 20,000. However, when choosing a particular molecular weight PEG with which to precipitate supercoiled plasmid DNA as part of the final concentration/polishing technique described herein, the PEG concentration must be adjusted to complement said PEG molecular weight. It is within the purview of one skilled in the art to make this determination, especially in light of what is taught in the instant application. For example, determining the appropriate concentration of PEG 8000 in order to completely precipitate plasmid DNA from a post-LRA filtrate is demonstrated herein (Example section 3). The test was performed under both differing temperatures and total DNA concentrations, varying said DNA concentration between 0.3 and 1.0 mg/mL since this is likely what will be encountered in large-scale purifications procedures. A sharp decrease in DNA solubility was noted in a solution of PEG 8000 when the PEG concentration was greater than about 2% (w/v) (see FIG. 7A). There was no effect on DNA solubility, however, due to solution temperature or DNA concentration for the range investigated. While the results in FIG. 7A show that DNA within the concentration range tested is completely precipitated by about 4% PEG 8000, a PEG 8000 concentration of 8% was chosen in the remainder of the studies described in Example section 3, giving a 2× safety factor. Alternatively, the purification process exemplified in Example 8 uses a 10% PEG 6000 solution to precipitate plasmid DNA. The concentration range shown in FIG. 5 indicates that plasmid DNA is completely precipitated in at least an 8% PEG 6000 solution. Thus, in one embodiment of the present invention, a concentrated PEG 6000 solution (e.g., 50% w/v) is fed to a cell lysate enriched in supercoiled plasmid DNA (a result, for example, of prior purification processes including but not limited CTAB-induced, selective precipitation of plasmid DNA and adsorption of impurities onto hydrated calcium silicate) to a final concentration of 10% (w/v) as a first step in the novel downstream concentration/polishing process of the present invention. It is also important to assess the time period in which to incubate the plasmid DNA-containing cell lysate with PEG to ensure that DNA precipitation is complete. The kinetics of PEG precipitation can be investigated to ensure that the hold time after PEG addition is sufficient to complete DNA precipitation. In the studies disclosed in the Examples section infra (Example 3), greater than 99% of the DNA was precipitated after about a five minute incubation period with PEG (see FIG. 8), indicating that, for example, a two hour hold time, as used in the purification process exemplified herein, is more than sufficient.

As described in detail in the Examples section infra, a prior DNA purification process disclosed in U.S. patent application Ser. No. 09/875,379 (supra) utilized a membrane ultrafiltration/concentration step as part of the final polishing process for plasmid DNA purification from an enriched, plasmid-DNA containing *E. coli* cell lysate (e.g., a post-calcium silicate filtrate, such as a post-LRA filtrate). This was followed by a 10× diafiltration for buffer exchange into formulation buffer, PBS (see FIG. 6A). While this final polishing step was satisfactory at volumes of approximately 100 L or less, larger manufacturing scale purification processes showed pump sizes and flow-rates beginning to reach the limit of technology. Thus, to avoid problematic process scale-up issues, the present invention relates to the replacement of a commonly used final polishing technique in plasmid DNA purification regimes (e.g., a first ultrafiltration, concentration step followed by a diafiltration, buffer exchange step) with a PEG precipitation step followed by a DNA concentration process which includes microfiltration under tangential flow filtration (compare FIG. 6A with FIG. 6B). Microfiltration under tangential flow filtration can represent one component of a stepwise filtration process whereby said microfiltration (and subsequent diafiltration) is the first part of said process, helping to clear residual RNA and impurities from the precipitated-DNA solution. The second filtration step (and subsequent diafiltration) both further concentrates the DNA and displaces the PEG with ethanol, dehydrating the DNA such that the final wet product can be dried under full vacuum to obtain a fine powdered form. While this final concentration/polishing technique requires more steps in comparison to the ultrafiltration/diafiltration technique of the prior disclosed process (see FIG. 6), the PEG precipitation process described herein is more easily scalable to large manufacturing volumes without compromising product quality or requiring the use of extremely large pumps and flow-rates. Importantly, this new process includes a final purification step that further reduces impurities, whereas the prior process was only employed for concentration and buffer exchange. Additionally, the need for sterile filtration after the DNA product is dried is eliminated due to ethanol addition in said second filtration/diafiltration step described above, as long as said step is performed aseptically. Importantly, the powdered product can also be resuspended in a liquid formulation. Thus, the benefits of the new unit operation described herein are the further reduction of residual RNA levels, possibly by 2 logs or more, elimination of excessive flow-rates and large pumps, reduction of cycle-time, and generation of a powdered product, reducing necessary storage space and possibly providing a more stable product.

Once the plasmid DNA has been precipitated by PEG as described above, impurities are cleared from the solution via a microfiltration step that concurrently concentrates the PEG-precipitated plasmid DNA slurry, wherein said microfiltration step occurs under tangential flow filtration mode. Thus, this microfiltration process concentrates the precipitated plasmid DNA in the retentate at the expense of impurities that are lost with the permeate. Membrane filtration is a separation technique widely used in purification regimes. Depending on membrane type, it can be classified as microfiltration or ultrafiltration. Microfiltration represents a size-exclusion, pressure-driven membrane process using a typical membrane pore size of between about 0.1 to about 10.0 microns. There are two main membrane filtration methods: (1) single pass, dead-end or direct flow filtration ("DFF"), and (2) crossflow or tangential flow filtration ("TFF"). It was found that when using DFF, impurities to be cleared from the precipitated plasmid DNA slurry can often become clogged at the membrane surface along with the precipitated plasmid DNA. TFF solves this clogging problem by re-circulating the precipitated plasmid solution, allowing the solution to flow tangentially to the surface of the membrane (synonymous to the term crossflow). The sweeping action of the fluid acts to minimize gel layer formation and surface fouling; and therefore, TFF is often quicker and more efficient than DFF. There are two important variables involved with all tangential flow techniques, namely the transmembrane pressure (i.e., the force that pushes impurities through the pores of the filter) and the crossflow velocity (i.e., the flow rate of the lysate across the membrane). Fluid is pumped from the sample feed across the membrane surface (crossflow) of the filter and back into the sample feed as the retentate. Backpressure applied to the retentate tube by a clamp or valve creates a transmembrane pressure which drives impurities smaller than the membrane pores through the filter and into the filtrate (or permeate) fraction. The crossflow sweeps larger molecules, which are retained on the surface of the membrane, back to the feed as retentate. Thus, the key to using TFF effectively is to regulate the transmembrane pressure and the crossflow velocity so that the largest volume of sample can be filtered without creating pore-plugging.

The Examples section infra demonstrates the use of TFF during microfiltration, acting to concentrate precipitated plasmid DNA (i.e., reduce the working volume) and to wash away any residual RNA and non-product soluble matter left in solution after precipitation. In the particular example disclosed, the post-LRA filtrate, as defined in U.S. patent application Ser. No. 09/875,379 (supra), is a plasmid containing solution of 3 M NaCl, 1.0 mg/mL purified DNA and some residual RNA. PEG 8000 MW was used to precipitate the plasmid DNA, added as a concentrated solution of 33% (w/v), over 15 minutes, until the final solution concentration was about 8% (w/v). The precipitate was aged for two hours and then concentrated using a 0.45-micron, hollow fiber membrane, tangential flow filter. The loading on the membrane was 180 g DNA/$m^2$ of membrane area; the recirculation rate was 9 L/m/min; and the flux was controlled at 2.5 L/$m^2$/min. Permeate was collected until a 20× concentration was achieved. In one embodiment of the present invention, after the PEG-precipitated DNA is concentrated, as described herein using microfiltration under TFF, the precipitate is then diafiltered against a PEG solution, wherein said diafiltration buffer contains PEG and salt at concentrations sufficient to ensure that the plasmid DNA remains precipitated during diafiltration. For example, plasmid DNA will remain precipitated if the diafiltration buffer contains approximately the same percentage of PEG used in the prior precipitation step (e.g., 8% w/v PEG 8000 in the example above and as further described in Example section 3) and about 1.2 M NaCl. Experiments have shown that salt concentration of between about 100 and about 600 mM NaCl is preferred to keep DNA precipitated in a 50% (v/v) ethanol solution. Thus, in order for the second filtration/diafiltration step described further infra to operate near 600 mM NaCl limit, it is preferable that the salt concentration exiting the first diafiltration is approximately 1.2 M. While it is possible to use a higher NaCl concentration value, this may cause precipitation of a larger amount of residual salt during the subsequent ethanol addition/dehydration step (described further below). Alternatively, it is possible to diafilter the precipitated DNA against a buffer with a lower NaCl concentration (e.g., 100 mM); however, under these conditions, the PEG concentration of said buffer should be increased to account for the low salt. As demonstrated in the Examples herein, if plasmid DNA is initially precipitated using PEG 8000 at a final solution concentration of about 8% (w/v), then a PEG 8000 solution of about 8% (w/v) with about 1.2 M NaCl is preferable to diafilter the precipitated DNA slurry after TFF microfiltration described above. Since PEG precipitates DNA by volume exclusion, and not via dehydration as with ethanol precipitation, the PEG-precipitated plasmid forms a soft, gel-like precipitate that can be dissociated into smaller pieces by mixing.

The second filtration/diafiltration process of the final concentration/polishing step of the present invention wherein plasmid DNA is first precipitated with PEG comprises: (a) partially dehydrating the precipitated, supercoiled plasmid DNA with the addition of ethanol; (b) concentrating the dehydrated plasmid DNA precipitate of step (a) by filtration; and, (c) diafiltering the precipitated plasmid DNA against 100% ethanol. The PEG-precipitated, concentrated (via the prior MF/diafiltration step) plasmid can be dehydrated by feeding an ethanolic solution (e.g., 100% or 200-proof) to the diafiltered precipitate to a final ethanol concentration such that the characteristic of precipitation changes from a volume exclusion to a dehydration mechanism. As a result, the physical property of the precipitated plasmid DNA also changes from a gel-like substance to a harder, less compressible precipitate. The resulting precipitate packs into a porous structure resulting in good fluxes and high loading capacities in the second filtration step (step (b) above). According to the present invention, partially dehydrating the precipitated, supercoiled plasmid DNA with ethanol occurs when incubating the precipitated DNA in an ethanolic solution which contains less than about 100% (v/v) ethanol. As such, different ethanol concentrations can be used to achieve the partial dehydration of step (a) above; however, a final ethanol concentration within the range of between about 30-80% (v/v) is preferred. Concentrations below about 30% (v/v) risk redissolving DNA back into solution; while concentrations above about 80% (v/v) begin to precipitate salts along with the plasmid DNA. In one embodiment of the present invention, the PEG-precipitated, concentrated (via the prior MF/diafiltration step described above) plasmid is dehydrated by the addition of 100% (200-proof) ethanol to a final concentration of 50% (v/v). After dehydrating the plasmid DNA precipitate, said precipitated DNA slurry is further concentrated (e.g., to approximately 30 g/L) by filtration and then diafiltered against 100% ethanol in preparation for vacuum drying. In the example provided herein, the dehydrated plasmid DNA slurry is concentrated by said second filtration in a filter dryer under stirred-cell operation which permits pressure filtration and vacuum drying, commonly known as a single-plate Nutsche filter dryer. The stirred-cell operation of said system creates flow of the alcohol-precipitated DNA solution on the filter surface with an impeller rather than by recirculation of said solution through channels. The filter dryer used to exemplify the second filtration/diafiltration process disclosed herein is fitted with a 25 µm stainless steel, mesh filter. Thus, the second filtration step of this portion of the novel downstream concentrating/polishing process preferably occurs using a single-plate Nutsche filter under stirred-cell mode and having a filter of between about <0.1 µm to 100 µm pore size, preferably of about a 25 µm pore size. The pore size is only important to trap the plasmid DNA precipitate on the filter while allowing the filtrate and any associated impurities to pass through the filter. In the example described infra, the concentrated DNA precipitate is then diafiltered against 100% (200 proof) alcohol, flux controlled at 3.2 L/m$^2$/min, in the same filter-dryer unit. Following the filtration, the powder is dried under vacuum for approximately 24 hours at 25-37° C., forming a fine product power. Alternatively, the powdered DNA product may be resuspended in a formulation buffer of choice. This second filtration/diafiltration procedure is performed to remove any remaining PEG from solution, to further dehydrate the product and to remove as much salt as possible.

Thus, the present invention relates to a method of purifying supercoiled plasmid DNA from a cell lysate of a large-scale microbial fermentation which comprises: (a) precipitating said supercoiled plasmid DNA with polyethylene glycol; and, (b) concentrating said precipitated, supercoiled plasmid DNA using a stepwise filtration process comprising microfiltration in a tangential flow filtration mode. This stepwise filtration process comprises: (a) a first filtration concentrating step comprising microfiltration under tangential flow filtration mode; (b) a first diafiltration step against a PEG-containing diafiltration buffer, wherein said diafiltration buffer contains sufficient concentrations of PEG, and optionally salt, to maintain the supercoiled plasmid DNA in precipitated form; (c) a dehydration step wherein the precipitated, supercoiled plasmid DNA is partially dehydrated by the addition of ethanol, (d) a second filtration concentrating step; and, (e) a second diafiltration step against 100% (v/v) ethanol. In a preferred embodiment, the diafiltration buffer of step (b) contains about 10% (w/v) PEG 6000 and about 1.2 M NaCl. The precipitated, supercoiled plasmid DNA can be dehydrated in step (c), after the microfiltration and first diafiltration step, with the addition of ethanol to a final concentration of between about 30% and about 80% (v/v). In a preferred embodiment, said precipitated, supercoiled plasmid DNA is partially dehydrated with the addition of ethanol to the microfiltration/diafiltration retentate to a final concentration of about 50% (v/v). In a further preferred embodiment, the second filtration and diafiltration of steps (d) and (e) above occur in a filter dryer equipped with a stainless steel mesh (or equivalent) screen, including but not limited to a single-plate Nutsche filter dryer operated under stirred-cell mode. Thus, the present invention relates to a method of purifying supercoiled plasmid DNA from a cell lysate of a large-scale microbial fermentation which comprises: (a) precipitating said supercoiled plasmid DNA with PEG; (b) concentrating said precipitated, supercoiled plasmid DNA using microfiltration under tangential flow filtration; (c) partially dehydrating said concentrated, precipitated DNA by the addition of ethanol; and, (d) concentrating said partially dehydrated, precipitated DNA in a stirred-cell filter dryer.

The present invention further relates to a method of purifying supercoiled plasmid DNA from a cell lysate of a large-scale microbial fermentation which comprises: (a) precipitating said supercoiled plasmid DNA with alcohol (including but not limited to ethanol, methanol and isopropanol); and, (b) concentrating said precipitated plasmid DNA by microfiltration under tangential flow filtration mode. The use of precipitation (either by PEG or alcohol), rather than ultrafiltration, to concentrate the product plasmid DNA is favored since solution phase plasmid is susceptible to shear damage when said ultrafiltration is modified for factory-sized production processes using standard pumps (e.g., lobe pumps). Earlier development work described in U.S. patent application Ser. No. 09/875,379 (supra) demonstrated that ethanol could be utilized as a precipitation solvent in batch mode to gain a dry powder form of plasmid DNA. However, this approach was inconsistent in terms of the post-precipitation filtration and wash steps, showing slow filtration rates and extreme cake compaction unless a gradual wash gradient was applied. Thus, in one embodiment of the present invention, the final downstream concentration/polishing step of the present invention features alcohol precipitation augmented by microfiltration in a tangential flow filtration mode to ultimately generate a purified bulk powder form of plasmid DNA. As an enhancement of this approach, continuous precipitation with concurrent microfiltration may significantly reduce vessel volumes relative to batch alcohol precipitation methods.

As noted earlier, prior to performing the final downstream concentration/polishing step of the present invention encompassing a first step of precipitating supercoiled plasmid DNA from a cell lysate (including, but not limited to, precipitating with PEG or alcohol), supercoiled plasmid DNA will have been enriched in said cell lysate as a result of both upstream and prior downstream purification processes (described in detail supra). Once a cell lysate enriched in supercoiled plasmid DNA is generated, said plasmid DNA-containing lysate is further processed to remove any residual impurities, representing the final polishing step in the plasmid DNA purification regimen. To demonstrate the final downstream concentration/polishing step of the present invention which comprises alcohol precipitation, supercoiled plasmid DNA is first precipitated from a post-LRA filtrate (as defined in U.S. patent application Ser. No. 09/875,379; supra). Without being bound by any particular theory, experiments presented in the Examples section herein testing the ability of various solvents (ethanol, isopropanol and methanol) and salts to precipitate plasmid DNA yield insight into the mechanism of DNA precipitation. DNA contains hydrophobic base pairs in addition to negatively charged phosphate groups that repel each other. If the phosphate repulsion is overcome, hydrophobic regions stack and DNA precipitates from solution. FIG. 9B shows that plasmid solubility is decreased by the addition of either salt or solvent. Solution ionic strength (salt concentration) affects solubility electrostatically whereby cations shield the repulsion of the negatively charged phosphate groups. One of skill in the art, using the investigations provided herein, as well as those already disclosed in the art, will appreciate the interplay between solvent and salt when precipitating plasmid DNA with alcohol as a first step in the final concentration/polishing purification step of the present invention.

As stated above, one embodiment of the present invention relates to a method of purifying supercoiled plasmid DNA from a cell lysate of a large-scale microbial fermentation which comprises: (a) precipitating said supercoiled plasmid DNA with ethanol; and, (b) concentrating said precipitated plasmid DNA by microfiltration under tangential flow filtration mode. Studies described in detail in the Examples section herein demonstrate that a sharp decrease in plasmid DNA solubility occurs in a 0.5 g/L plasmid solution with ethanol concentrations of between about 30% and 33% (v/v) and NaCl concentrations between about 1.8 and 3.4 M. As noted above, one of skill in the art will recognize that solution ionic strength (salt concentration) plays a role in the efficiency of plasmid DNA precipitation with alcohol and, thus, will appreciate the need for providing salt and ethanol at sufficient concentrations for a plasmid solution of a particular DNA concentration to achieve precipitation of said plasmid. In addition, the importance of maintaining appropriate concentrations of said components to ensure that plasmid DNA remains precipitated during subsequent filtration and wash steps will be recognized by the skilled artisan. In one embodiment of the present invention, supercoiled plasmid DNA is precipitated as a first step of the downstream concentration/polishing process disclosed herein (step (a) above) with the addition of ethanol to a plasmid DNA-enriched cell lysate to a final concentration of about 40% (v/v), wherein said cell lysate contains approximately about 3 M NaCl.

In a further embodiment of the present invention, after the plasmid DNA has been precipitated by alcohol (including but not limited the ethanol, methanol and isopropanol), said precipitated plasmid is then concentrated via a stepwise filtration process. Said stepwise filtration process comprises: (a) a first filtration concentrating step comprising microfiltration under tangential flow filtration mode; (b) a first diafiltration step against an ethanolic solution, wherein the ethanol concentration of said solution is sufficient to keep said supercoiled plasmid DNA precipitated; (c) a second filtration concentrating step; and (d) a second diafiltration step against 100% (v/v) ethanol. In the Examples described herein, an attempt was made to diafilter a precipitated plasmid solution (0.86 g/L plasmid solution precipitated with about 40% (v/v) ethanol and about 3 M NaCl) against 80% (v/v) EtOH under direct flow filtration with a sidearm flask and a 0.2 micron membrane filter (2.1 cm² filter area). A significant decrease in flux was noted as filtration progressed, resulting in the formation of a gel-like filter cake. For a large scale batch filtration, it was thus estimated that when using a 5 ft diameter, 0.2 micron filter (19.6 ft² membrane area), filtration under direct flow would be completed after 243 hours. Due to this impractical filtration time, a high-area, tangential flow filtration ("TFF") membrane was considered as an alternative method. To this end, plasmid DNA precipitated with about 40% (v/v) ethanol and about 3 M NaCl was microfiltered using a 0.22-μm PVDF tangential flow filtration membrane. The suspension filtered easily at 15 mL/min, with no decrease in permeate flux over the course of the experiment. This indicates that solids were freely removed from the membrane surface and did not form a cake layer.

The microfiltration and first diafiltration step of the stepwise filtration process that accompanies alcohol-induced plasmid precipitation is performed in order both to clear residual salt and excess water from the solution and to concurrently concentrate the alcohol-precipitated (e.g., ethanol-precipitated) plasmid DNA. This process concentrates the precipitated plasmid DNA (i.e., reduces the working volume) in the retentate at the expense of salt and water lost with the permeate. The concentrated, precipitated plasmid DNA is then diafiltered, also aiding in the removal of salt. In one embodiment of the present invention, the ethanol-precipitated plasmid DNA that has been concentrated by TFF microfiltration is subsequently diafiltered against a solution comprising between about 60% to about 100% ethanol. Because plasmid DNA is completely insoluble in an 80% v/v ethanolic solution, even in the absence of salt, diafiltration with 80% ethanol can be used to remove NaCl from the suspension while maintaining conditions in which plasmid DNA is insoluble. The precipitated plasmid DNA slurry is then further concentrated by a second filtration step and diafiltered a second time against 100% (200-proof) ethanol. In one embodiment of the present invention, this second filtration/diafiltration process is performed in a filter dryer including but not limited to a single-plate Nutsche filter dryer, as described above. The wet powder can be vacuum dried (e.g., at 25-37° C.); and, the resulting powdered DNA product may be resuspended in a formulation buffer of choice.

Alcohol-induced plasmid precipitation in batch mode requires a vessel large enough to hold both the batch volume and the amount of ethanol required for precipitation. However, if both feed and ethanol could be continuously pumped into a smaller, intermediate container from which microfiltration simultaneously removes liquors to maintain constant volume, the large precipitation vessel would no longer be needed, even if precipitation were conducted at high solvent ratios. In this mode, solvent waste could also be minimized by continuously distilling the permeate and recycling to the precipitation vessel. Thus, one embodiment of the present invention relates to a method of purifying supercoiled plasmid DNA from a cell lysate of a large-scale microbial fermentation which comprises: (a) precipitating said supercoiled plasmid DNA using alcohol (including but not limited to ethanol, methanol and isopropanol); and (b) concentrating said precipitated supercoiled plasmid DNA by microfiltration under tangential flow filtration; wherein step (a) and step (b) are performed under continuous precipitation/microfiltration conditions. Said continuous precipitation/microfiltration process occurs when ethanol and plasmid solution are added continuously to a stirred vessel while microfiltration is simultaneously conducted from the same vessel, maintaining a constant volume. As an adjunct to this approach, continuous distillation of the permeate provides recycling of enriched ethanol to the precipitation, minimizing the required solvent volume and permitting precipitation at higher and even more favorable alcohol concentrations. Thus, the continuous precipitation/microfiltration process included as part of the present invention may or may not include alcohol (e.g., ethanol) recovery. As described in detail in the Examples section infra, a sufficient hold time whereby the plasmid particles can fully dehydrate is necessary prior to initiation of microfiltration to avoid clogging the microfiltration membrane. Ensuring that the precipitated plasmid DNA is fully dehydrated also helps to eliminate potential pressure increases caused due to channel plugging by large, hydrated particles. The continuous precipitation/microfiltration approach may be especially attractive for certain preparations that require high alcohol levels for precipitation.

In one embodiment of the present invention, the novel upstream and novel downstream purification processes described herein are combined in a single process for the isolation of supercoiled plasmid DNA from a cell lysate of a large-scale microbial fermentation. Thus, the present invention further relates to a method of purifying supercoiled plasmid DNA from a cell lysate of a large-scale microbial fermentation which comprises: (a) lysing microbial host cells containing supercoiled plasmid DNA in a physiological buffer, forming a host cell lysate; (b) clarifying said host cell lysate by flocculating host cell debris, retaining supercoiled plasmid DNA in solution; (c) precipitating said supercoiled plasmid DNA; and, (d) concentrating said precipitated supercoiled plasmid DNA using microfiltration under a tangential flow filtration mode. In one embodiment of this part of the present invention, the host cell lysate of step (a) above is generated by lysis of microbial host cells in a standard STET buffer containing lysozyme. In another embodiment of this part of the present invention, the host cell lysate of step (a) is generated by passage of microbial host cells through a heat exchange apparatus as disclosed in PCT International Application Nos. PCT/US95/09749 and PCT/US96/07083. As described in detail supra, it is shown herein that polyethylene glycol (PEG) is an effective flocculation agent of host cell debris for purposes of generating a clarified cell lysate in preparation for downstream purification of supercoiled plasmid DNA from microbial cells. Thus, in one embodiment of this portion of the present invention, the host cell lysate is clarified in step (b) above with PEG. The PEG flocculant can be a component of the original lysis buffer or can be added to the cell lysate after lysis has occurred. As explained supra, the quantity of PEG flocculant used to clarifying the host cell lysate is dependent on its molecular weight. In a preferred embodiment of the present invention, approximately 3.7% (w/v) PEG 6000 is used to flocculate host cell debris, as described herein; however, it should be appreciated that due to the close interplay between PEG polymer concentration and molecular weight on effectuating flocculation, any specific PEG concentration and PEG molecular weight disclosed herein should be viewed as a guideline and not limiting to the invention as a whole. To prepare the cell lysate for flocculation, said lysate may be subjected to an alkaline pH shift and subsequent neutralization prior to flocculation. The alkaline pH shift comprises raising the pH of the host cell lysate to an alkaline value of between about pH 12 and about pH 13 with the addition of a concentrated base. The subsequent neutralization of the alkaline-shifted, host cell lysate comprises lowering the pH of said cell lysate to a value of between about pH 7 and about pH 9 (i.e., lowering the pH to approximately the same level of the lysate prior to the alkaline shift). The alkaline pH shift and subsequent neutralization process may occur either prior to or after the addition of the PEG flocculant. Thus, the present invention relates to a method of purifying supercoiled plasmid DNA from a cell lysate of a large-scale microbial fermentation which comprises: (a) lysing microbial host cells containing supercoiled plasmid DNA in a STET buffer containing lysozyme; (b) subjecting said host cell lysate to an alkaline pH shift and subsequent neutralization; (c) clarifying said host cell lysate by flocculating host cell debris with a PEG flocculant; (d) precipitating said supercoiled plasmid DNA; and (e) concentrating said precipitated supercoiled plasmid DNA using microfiltration under a tangential flow filtration mode. In one embodiment of the present invention, the supercoiled plasmid DNA located in solution is precipitated in step (d) with a precipitant selected from the group consisting of alcohol (e.g., 40% v/v ethanol) and PEG (e.g., 10% w/v PEG 6000). Additionally, the concentrating step of step (e) described above may be a stepwise filtration process. If said plasmid DNA was first precipitated with PEG, said stepwise filtration process comprises: (a) a first filtration concentrating step comprising microfiltration under tangential flow filtration; (b) a first diafiltration step against a PEG-containing diafiltration buffer, wherein said diafiltration buffer contains sufficient PEG and salts to keep said supercoiled plasmid DNA precipitated; (c) a dehydration step wherein the precipitated, supercoiled plasmid DNA is partially dehydrated by the addition of ethanol; (d) a second filtration concentrating step; and, (e) a second diafiltration step against 100% (v/v) ethanol. If said plasmid DNA was first precipitated with alcohol (e.g., ethanol), said stepwise filtration process comprises: (a) a first filtration concentrating step comprising microfiltration under tangential flow filtration; (b) a first diafiltration step against an alcoholic solution (e.g., ethanol), wherein the concentration of the alcoholic solution is sufficient to keep said supercoiled plasmid DNA precipitated; (c) a second filtration concentrating step; and (d) a second diafiltration step against 100% (v/v) alcohol (e.g., 100% ethanol).

To this end, the present invention further relates to a combined process of purifying supercoiled plasmid DNA from a cell lysate of a large-scale microbial fermentation which comprises: (a) harvesting microbial host cells from a fermentation broth or culture medium; (b) lysing the host cells in a sufficient amount of a physiological lysis solution; (c) subjecting the host cell lysate to an alkaline pH shift by raising the pH of said lysate to between about pH 12 and about pH 13; (d) neutralizing the alkaline-shifted cell lysate to approximately the pH of the lysis buffer; (e) clarifying the cell lysate of step (d) by flocculating host cell debris with PEG; (f) removing said flocculated host cell debris; (g) selectively precipitating supercoiled plasmid DNA with a hexadecyltrimethylammonium bromide-induced precipitation; (h) redissolving the supercoiled plasmid DNA and adsorbing impurities in a well defined buffer of optimized ionic strength further containing hydrated, crystallized calcium silicate; (i) adsorbing remaining impurities with a second hydrated, crystallized calcium silicate-induced adsorption; (j) precipitating supercoiled plasmid DNA with PEG; (k) concentrating the precipitated, supercoiled DNA using microfiltration under a tangential flow filtration mode; (l) partially dehydrating the precipitated, supercoiled DNA with addition of ethanol; (m) concentrating the dehydrated supercoiled DNA in a stirred-cell filter dryer; and, (n) drying to remove ethanol, leaving a fine, powdered DNA product. In one embodiment of the present invention, a stepwise detergent precipitation is used in the purification process described immediately above. Said stepwise process comprises a first low-cut precipitation step to remove residual proteins and endotoxins from the cell lysate followed by a high-cut precipitation step to precipitate plasmid DNA. The first, low-cut step can be performed prior to removal of the flocculated host cell debris. In such a case, the high-cut precipitation step would occur using the clarified lysate (i.e., after removal of the host cell debris), represented by step (g) above.

The present invention also relates to a combined process of purifying supercoiled plasmid DNA from a cell lysate of a large-scale microbial fermentation which comprises: (a) harvesting microbial host cells from a fermentation broth or culture medium; (b) lysing the host cells in a sufficient amount of a standard STET buffer containing lysozyme; (c) subjecting the host cell lysate to an alkaline pH shift by raising the pH of said lysate to between about pH 12 and about pH 13; (d) neutralizing the alkaline-shifted cell lysate to approximately the pH of the STET buffer; (e) clarifying the cell lysate of step (d) by flocculating host cell debris with PEG; (f) removing said flocculated host cell debris; (g) selectively precipitating supercoiled plasmid DNA with a hexadecyltrimethylammonium bromide-induced precipitation; (h) redissolving the precipitated plasmid DNA and adsorbing impurities in a well defined buffer of optimized ionic strength and further containing hydrated, crystallized calcium silicate; (i) adsorbing remaining impurities with a second hydrated, crystallized calcium silicate-induced adsorption; (j) precipitating supercoiled plasmid DNA with PEG; (k) concentrating the precipitated, supercoiled DNA using microfiltration under a tangential flow filtration mode; (l) partially dehydrating the precipitated, supercoiled DNA with addition of ethanol; (m) concentrating the dehydrated supercoiled DNA a stirred-cell filter dryer; and, (n) drying to remove ethanol, leaving a fine, powdered DNA product. In one embodiment of the present invention, a stepwise detergent precipitation is used in the purification process described immediately above. Said stepwise process comprises a first low-cut precipitation step to remove residual proteins and endotoxins from the cell lysate followed by a high-cut precipitation step to precipitate plasmid DNA. The first, low-cut step can be performed prior to removal of the flocculated host cell debris. Said high-cut precipitation step would then occur using the clarified lysate (i.e., after removal of the host cell debris), represented by step (g) above.

The present invention further relates to a combined process of purifying supercoiled plasmid DNA from a cell lysate of a large-scale microbial fermentation which comprises: (a) harvesting microbial host cells from a fermentation broth or culture medium; (b) lysing the host cells in a sufficient amount of a physiological lysis solution; (c) subjecting the host cell lysate to an alkaline pH shift by raising the pH of said lysate to between about pH 12 and about pH 13; (d) neutralizing the alkaline-shifted cell lysate to approximately the pH of the lysis buffer; (e) clarifying the cell lysate of step (d) by flocculating host cell debris with PEG; (f) removing said flocculated host cell debris; (g) selectively precipitating supercoiled plasmid DNA with a hexadecyltrimethylammonium bromide-induced precipitation; (h) redissolving the precipitated plasmid DNA and adsorbing impurities in a well defined buffer of optimized ionic strength and further containing hydrated, crystallized calcium silicate; (i) adsorbing remaining impurities with a second hydrated, crystallized calcium silicate-induced adsorption; (j) precipitating supercoiled plasmid DNA with ethanol; (k) concentrating the precipitated, supercoiled DNA using microfiltration under a tangential flow filtration mode; (l) further concentrating the dehydrated supercoiled DNA a stirred-cell filter dryer; and, (m) drying to remove ethanol, leaving a fine, powdered DNA product. In one embodiment of the present invention, a stepwise detergent precipitation is used in the purification process described immediately above. Said stepwise process comprises a first low-cut precipitation step to remove residual proteins and endotoxins from the cell lysate followed by a high-cut precipitation step to precipitate plasmid DNA. The first, low-cut step can be performed prior to removal of the flocculated host cell debris. In such a case, the high-cut precipitation step would then occur using the clarified lysate (i.e., after removal of the host cell debris), represented by step (g) above.

The present invention also relates to a combined process of purifying supercoiled plasmid DNA from a cell lysate of a large-scale microbial fermentation which comprises: (a) harvesting microbial host cells from a fermentation broth or a culture medium; (b) lysing the host cells in a sufficient amount of a standard STET buffer containing lysozyme; (c) subjecting the host cell lysate to an alkaline pH shift by raising the pH of said lysate to between about pH 12 and about pH 13; (d) neutralizing the alkaline-shifted cell lysate to approximately the pH of the STET buffer; (e) clarifying the cell lysate of step (d) by flocculating host cell debris with PEG; (f) removing said flocculated host cell debris; (g) selectively precipitating supercoiled plasmid DNA with a hexadecyltrimethylammonium bromide-induced precipitation; (h) redissolving the precipitated plasmid DNA and adsorbing impurities in a well defined buffer of optimized ionic strength and further containing hydrated, crystallized calcium silicate; (i) adsorbing remaining impurities with a second hydrated, crystallized calcium silicate-induced adsorption; (j) precipitating supercoiled plasmid DNA with ethanol; (k) concentrating the precipitated, supercoiled DNA using microfiltration under a tangential flow filtration mode; (l) further concentrating the dehydrated supercoiled DNA a stirred-cell filter dryer; and, (m) drying to remove ethanol, leaving a fine, powdered DNA product. In one embodiment of the present invention, a stepwise detergent precipitation is used in the purification process described immediately above. Said stepwise process comprises a first low-cut precipitation step to remove residual proteins and endotoxins from the cell lysate followed by a high-cut precipitation step to precipitate plasmid DNA. The first, low-cut step can be performed prior to removal of the flocculated host cell debris. Said high-cut precipitation step would then occur using the clarified lysate (i.e., after removal of the host cell debris), represented by step (g) above.

All publications mentioned herein are included for the purpose of describing and disclosing methodologies and materials that might be used in connection with the present invention. Nothing herein is to be construed as an admission that the invention is not entitled to antedate such disclosure by virtue of prior invention.

Having described preferred embodiments of the invention with reference to the accompanying figures, it is to be understood that the invention is not limited to those precise embodiments, and that various changes and modifications may be effected therein by one skilled in the art without departing from the scope or spirit of the invention as defined in the appended claims.

The following examples are provided to illustrate the present invention without, however, limiting the same hereto:

EXAMPLE 1

Flocculation of Host Cell Debris with PEG

Analytical methods—Analytical methods utilized include: (i) anion-exchange ("AEX") HPLC Assay; (ii) gel electrophoresis with E-gels (Invitrogen; 0.8% agarose with ethidium bromide); and (iii) qPCR using a Taq man PCR assay. E-gels were run at 60 volts for 50 minutes with 20 µL loading per well. Prior to running the E-gel assay, samples were pre-treated with ethanol precipitation (2 equivalent volumes) and centrifuged in an Eppendorf microfuge for 5 minutes. Supernatants were decanted, and pellets were allowed to dry for 5 minutes prior to resuspension in 10 mM Tris buffer at pH 8.0.

The pretreated samples were then diluted in 1×TAE buffer prior to loading on the E-gel. An identical pretreatment was performed on samples submitted for qPCR analysis.

Lysis with lysozyme—Initial E. coli lysis studies were performed to assess the impact of lysozyme, base/acid treatment (base addition to a pH of 12-13 and subsequent neutralization by acid addition to approximately pH 7-9), and temperature on lysis performance. Cell lysis was evaluated using cells resuspended to $OD_{600}$ of 45. Lysis without lysozyme, regardless of temperature or base/acid treatment, resulted in lower yields. Lysis at 20° C. with lysozyme (500 U/mL Ready-Lyse™; Epicentre) in a standard STET buffer (50 mM Tris-HCl, 100 mM EDTA, 2% v/v Triton®-X-100, 8% w/v sucrose, pH 8.2) but no base/acid treatment yielded lower plasmid DNA recovery (plasmid DNA concentration of ca. 0.3 g/L) when compared to lysis at 37° C. The highest yields were achieved using lysozyme incubation (500 U/mL) followed by base/acid treatment. The base/acid treatment consisted of addition of concentrated NaOH (5 M stock; final solution concentration of 0.25 M), 15 minute incubation, and addition of acetic acid (5 M stock; final solution concentration of 0.25 M). Plasmid DNA yield was ca. 0.5 g/L from $OD_{600}$ 45 lysates incubated at either 20° C. or 37° C. and subjected to base/acid treatment.

Lysate flocculation studies—Screening studies were conducted to characterize the effects of PEG flocculation on settling of cell debris. FIG. 1 shows four Nalgene bottles with different $OD_{600}$ 45 E. coli lysates (containing plasmid DNA). Bottle 1 contains a lysate generated by resuspending cells in STET buffer (described above) and incubating with lysozyme (500 U/mL Ready-Lyse™) at 20° C. Bottle 2 contains the same lysate as in Bottle 1, but a base/acid step was performed after lysozyme incubation (pH shift from ca. 8.5 to ca. 12.5 and back to ca. 8.5). The lysate in Bottle 3 was generated by resuspending cells in STET buffer containing 3% PEG 3000 and incubating with lysozyme (500 U/mL) at 20° C. Bottle 4 contains the same lysate as in Bottle 3, but the base/acid step was performed after lysozyme incubation. The pH-shifted, PEG-treated material settled over a 2-day period by gravity alone, indicating improved performance during centrifugation would be achieved. It was determined that PEG works extremely well as a flocculant for cell debris, especially after base/acid treatment of the host cell lysate (i.e., pH shift from ca. pH 8.5 to ca. pH 12.5, and then back to ca. pH 8.5; as described above). In fact, the addition of PEG had an opposite effect, i.e., debris became more difficult to pellet if applied to a lysate which had not been subjected to base/acid treatment.

Figure 2:
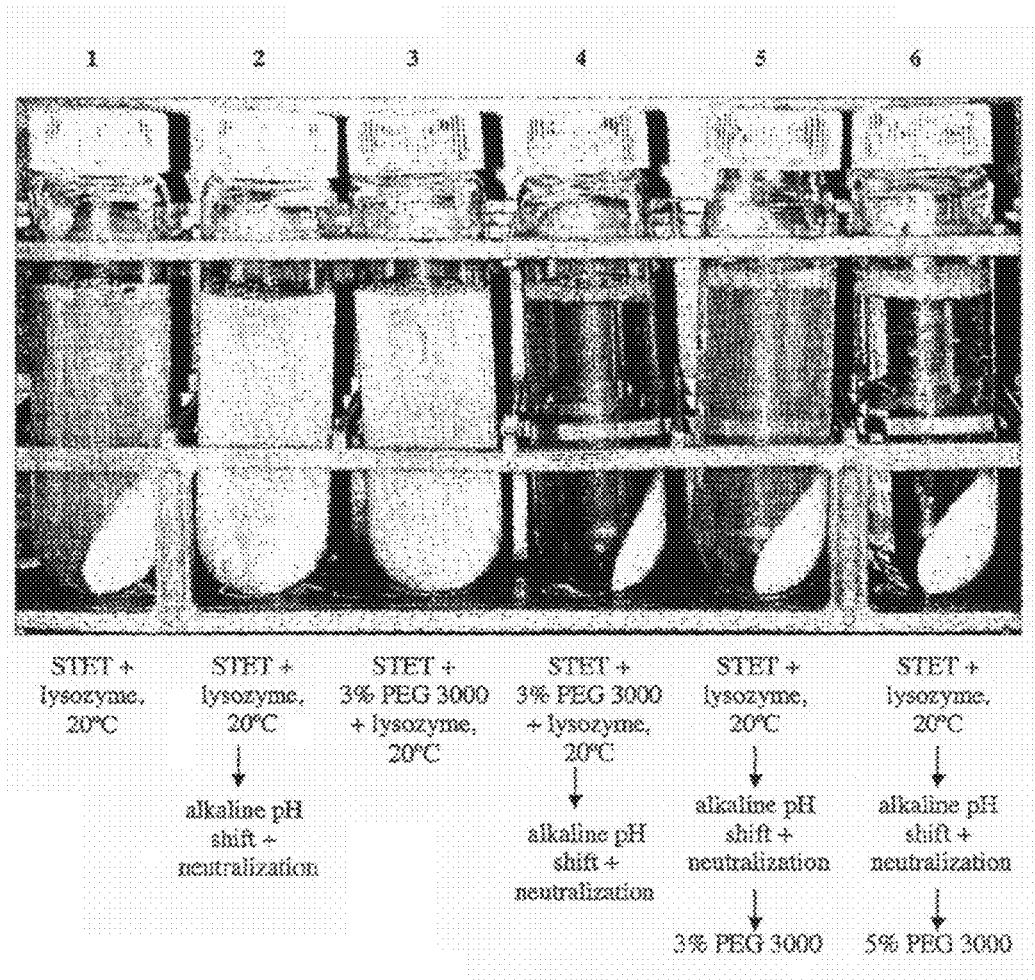
FIG. 2 shows 50 mL centrifuge tubes containing various cell lysates having an initial $OD_{600}$ of 45 and spun at 16,000×g for 5 minutes. The lysate in Tube 1 was generated by resuspending cells in STET buffer and incubating with lysozyme at 20° C. The lysate in Tube 2 is the same as in Tube 1, except it was subjected to an alkaline pH shift and subsequent neutralization (as described above for FIG. 1) after lysozyme incubation. The lysate in Tube 3 was generated by resuspending cells in STET buffer containing 3% PEG 3000 and incubating with lysozyme at 20° C. The lysate in Tube 4 is the same as in Tube 3, except it was subjected to an alkaline pH shift and subsequent neutralization after lysozyme incubation. The lysate in Tube 5 is the same as in Tube 2, except the PEG was added after the alkaline pH shift/acid neutralization step. The lysate in Tube 6 is the same as in Tube 2, except a final concentration of 5% PEG 3000 was added after the alkaline pH shift/neutralization step
Figure 3:
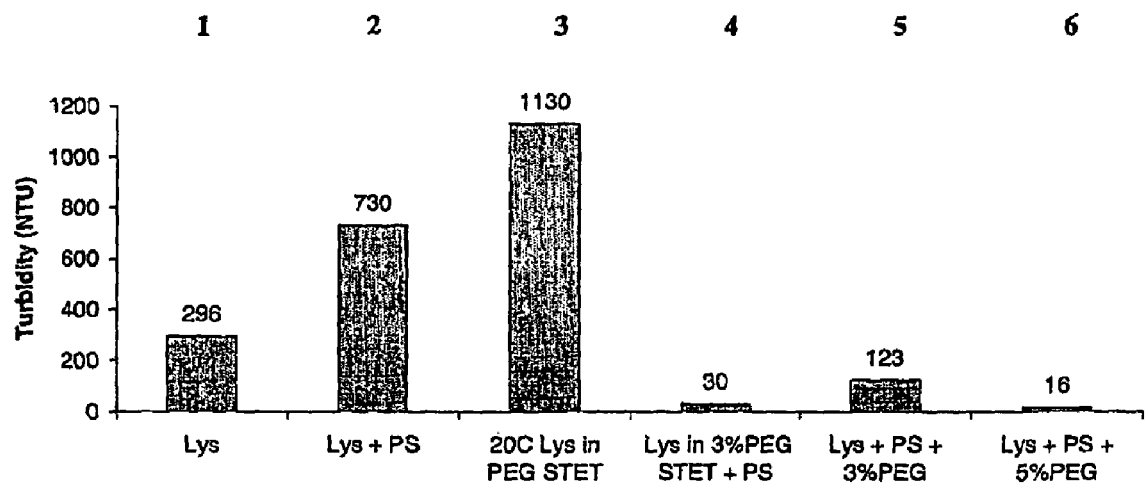
FIG. 3 shows turbidity measurements for the lysates shown in FIG. 2. Lys=lysozyme; PS=pH shift; PEG STET=3% PEG 3000+STET.

To further test PEG-induced flocculation, various cell lysates treated as described in FIG. 2 were aliquoted into 50 mL centrifuge tubes. The bottles were incubated for 15 minutes on a rotary mixer and then centrifuged. Results, shown in FIG. 2, demonstrate the action of PEG as a flocculant when added to a lysate subjected to base/acid treatment. FIG. 3 shows turbidity measurements for the supernatants of the six samples tested in FIG. 2. A solution turbidity of 15.5 NTU after centrifugation was shown with a final PEG concentration of 5% (Tube 6), compared to the 730 NTU turbidity of the control (Tube 2). This indicates that centrifugation can be used as a clarification strategy to achieve sub 20 NTU clarity without using a polishing filtration. These results also indicate that PEG is an effective flocculant if added either prior to or after base/acid treatment.

Effect of PEG molecular weight on flocculation of cell debris—The effects of PEG concentration and molecular weight on flocculation were investigated using a rapid screening method based on settling performance of cell debris. Cells were incubated in the presence of lysozyme (500 U/mL) and subjected to a base/acid treatment as described above. Various PEG stock solutions were mixed into 10-mL aliquots of the lysate, and the resulting mixtures were allowed to settle at room temperature for ca. 16 hours. The volume of settled solids and the turbidity of supernatant ($OD_{600}$) were measured (FIG. 4A). DNA concentrations were also measured since PEG at high concentrations is a known DNA precipitant. FIG. 4B shows both DNA concentration (as determined by AEX assay) and supernatant turbidity for a study using PEG 3000. Results demonstrate that there is a PEG 3000 concentration range for which cell debris flocculates, but DNA is not precipitated. Results also demonstrate that DNA does precipitate if PEG 3000 concentration is increased above approximately 5%.

Figure 5:
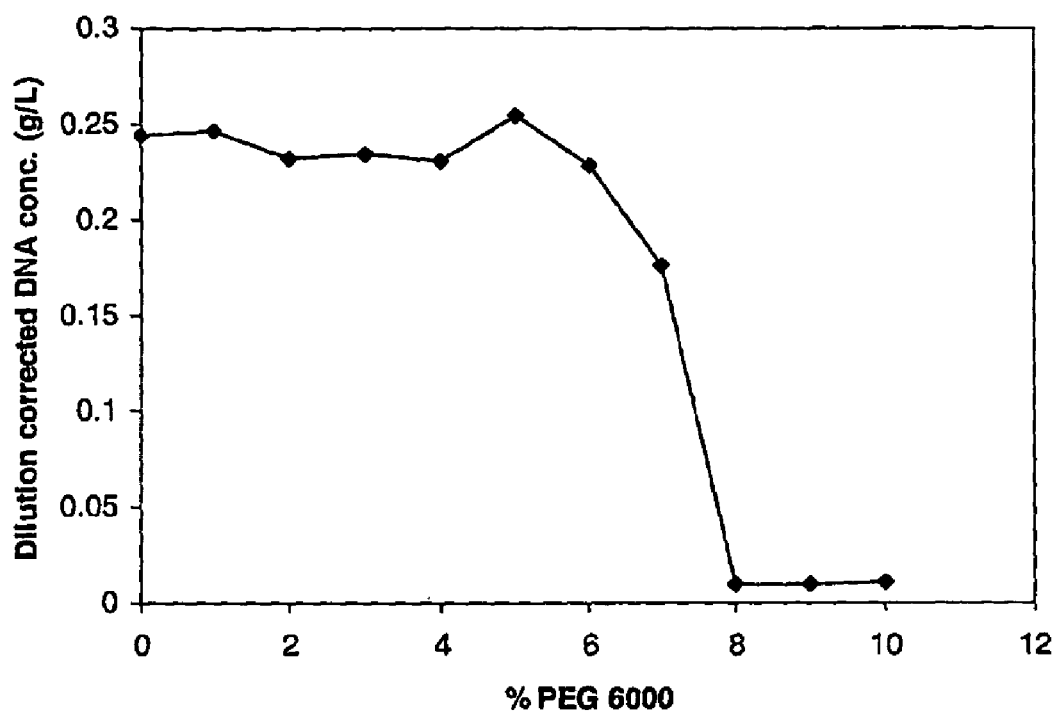
FIG. 5 shows a plasmid DNA precipitation curve for increasing concentrations (0-8% w/v) of PEG 6000 in lysozyme/pH shifted lysates.

PEG 6000 DNA flocculation experiments—Utilizing an alkaline-pH shifted and subsequently neutralized lysate, a plasmid DNA precipitation curve was generated for PEG 6000. The precipitation curve is shown in FIG. 5. From this data, a PEG 6000 concentration of approximately 3.7% during the lysis/lysate clarification step of the present invention will sufficiently remove any danger of precipitating plasmid DNA during flocculation of host cell debris (>6% PEG 6000).

Upper limit in cell slurry concentration for effective lysis—A study was performed to determine the maximum concentration of cells that can be lysed using the novel lysis method described above comprising lysozyme incubation, followed by base/acid treatment and PEG addition for lysate clarification. Several cell slurry concentrations (expressed in terms of optical density at 600 nm, $OD_{600}$) were investigated. It was determined that an initial $OD_{600}$ of 70 was optimal, resulting in a clarified lysate with a total DNA concentration of ca. 0.7 g/L. After the addition of base, acid and PEG solution to this initial cell lysate, the $OD_{600}$ is slightly diluted from its original value to ~60.

Figure 18:
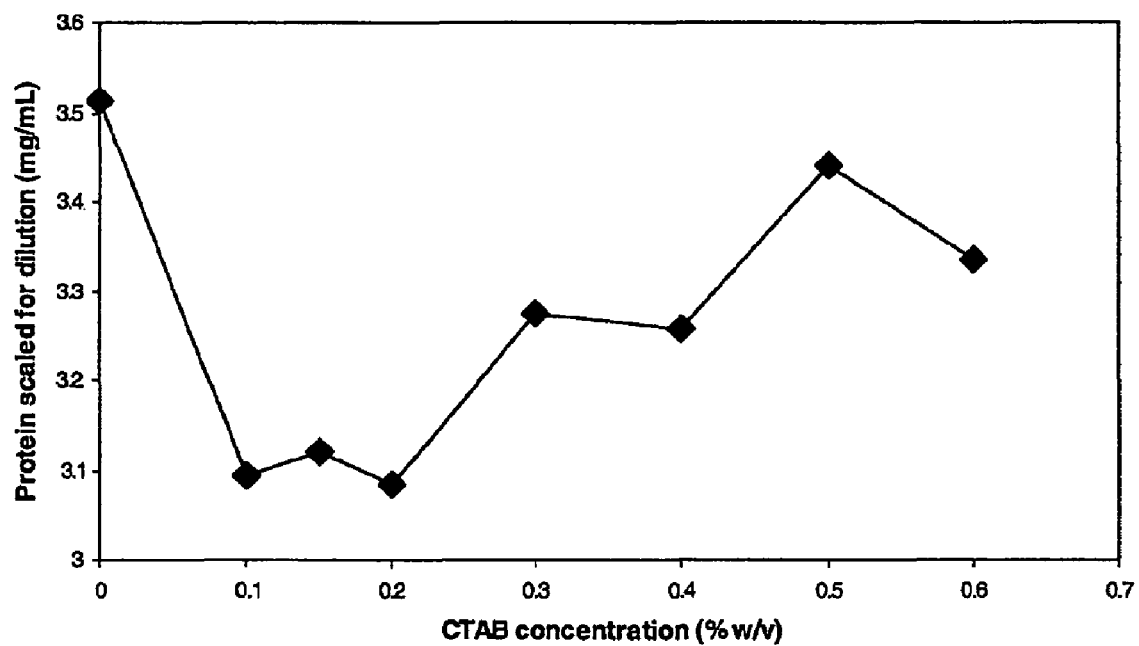
FIG. 18 shows the protein levels, as determined by BCA assay, in a PEG 6000-flocculated cell lysate as a function of final CTAB concentration, whereby CTAB is introduced into the lysate by adding 2% (w/v) CTAB in 40 mM NaCl.

CTAB low-cut impurity precipitation—After flocculation with PEG 6000, it was found that CTAB could be added to the flocculated lysate (prior to lysate clarification) to reduce levels of soluble protein. This was done by adding 2% (w/v) CTAB in 40 mM NaCl to a final concentration of 0.15% (w/v) over 1 hour. FIG. 18 shows the protein level, as determined by BCA assay, as a function of final CTAB concentration. A minimum protein concentration is achieved between 0.1% and 0.2% (w/v) CTAB.

Continuous centrifugation during flocculation procedure—To simulate continuous centrifugation conditions, PEG flocculation of a host cell lysate containing supercoiled plasmid DNA was tested with a model (CTC 3) Westfalia centrifuge. While this model centrifuge is not capable of solids discharge, it has the same internal geometry as larger production centrifuges. The centrifuge has a 2 L bowl with 1 L of holding capacity for solids. A host cell lysate containing supercoiled plasmid DNA of interest (generated via lysozyme incubation, an alkaline pH shift and subsequently neutralization) and flocculated with PEG 6000 was passed through the unit operating at 10,000×g at 250 mL/min. Approximately 18 L of lysate could be passed through the unit before filling the bowl. Although the solids were very thick and compressed, there was no loss in DNA concentration over the course of the run. Turbidities were <30 NTU in the final clarified lysate.

Polish filtration—In addition to the centrifugation procedure described above, a polish depth filtration can be utilized to remove residual solids from the centrifuged lysate. For example, a cellulosic or diatomaceous earth-based depth filters (e.g., Millipore DE40 or CE50 filters) can be used at an approximate loading of about 70 L/m².

EXAMPLE 2

Plasmid DNA Purification after Lysozyme Incubation, Base/Acid Treatment and PEG Flocculation Analytical methods—See methods of Example 1.

30 L lysis: Frozen cells containing supercoiled plasmid DNA harvested from a 2,000 L *E. coli* fermentation process were thawed in a warm (ca. 35° C.) water bath and diluted to $OD_{600}$ 70 using STET buffer (50 mM Tris HCl, 100 mM EDTA, 2% v/v Triton® X-100, 8% w/v Sucrose, pH 8.2) in a 50 L Lee Tank with a 5-inch A310 impeller. A resuspension volume of 30 L was achieved. Ready-Lyse™ lysozyme (500 U/mL, Epicentre) was added, and the resulting cell slurry was incubated at 37° C. for ca. 2 hours. The cell slurry was then cooled to 20° C., and 5 M NaOH was added slowly in subsurface mode over a 60-minute period to increase pH of the lysozyme lysate to ca. 12. After a 30-minute hold period, 2.5 M acetic acid was then added over 60 minutes to reduce the pH to 8-9. PEG 3000 (50% w/v) in RCM 6 (saline, 150 mM NaCl) was then slowly added to a final concentration of 5% (w/v) PEG. The total lysate volume after adding NaOH, acetic acid, and PEG 3000 increased from 30 L (ca. $OD_{600}$ 70) to 35 L (ca. $OD_{600}$ 60). PEG-flocculated lysate was then transferred to 1-L JLA8.1000 centrifuge bottles and spun for 15 minutes at 15.9 kG. Supernatants were pooled, yielding clarified lysate with a turbidity of ca. 17 NTU. The pooled clarified lysate was then stored at 4° C.

4.3 L lysis: An identical 4.3 L lysis from a 1 L *E. coli* fermentation containing a supercoiled plasmid DNA was completed using a 7 L jacketed glass vessel with a 3-inch diameter A310 impeller. The vessel has a rounded bottom, 8 inches in diameter, and the liquid level was approximately 8 inches. The impeller was positioned roughly at a 15-degree angle and run at a speed of 400 rpm. Ready-Lyse™ lysozyme (500 U/mL) was added and allowed to incubate for 2.5 hours at 37° C. prior to the pH shift. Then the temperature was reduced to 20-25° C., and 5 N NaOH (0.0150 L, final solution concentration of 0.25 M) was added over 60 minutes. The pH after base addition was 12.5. After addition of base, the mixing rate was lowered to 250 rpm (to help prevent any DNA degradation due to impeller shear), and the lysate was allowed to incubate at high pH for 30 minutes. Concentrated acetic acid (2.5 N, 0.3 L) was added over 60 minutes to a final solution concentration of 0.25 M. Five minutes into the acid addition the impeller speed was raised to 350 rpm for better mixing. The final pH after acid addition was 8.4. Concentrated PEG 3000 (50%; 0.475 L) stock was then added over 1 hour. After ca. 30 minutes of aging, the lysate was aliquoted into 1-L Beckman centrifuge bottles and centrifuged at 15 kG for 15 minutes. Resulting supernatant was decanted into a 10 L Nalgene container through a 20-μm, 4-inch diameter, stainless steel screen to catch any large particulates.

Results—As a result of the probe experiments described in Example 1, a 4.3-L lysis procedure was performed. The concentration of total DNA in the clarified lysate was 0.8 g/L, as determined by gel electrophoresis assay. Results from qPCR analyses of host genomic DNA concentration are shown in Table 1. Clarified lysate was determined to contain only ca. 2% genomic DNA, which is a significant reduction in genomic DNA levels typically achieved using heat lysis method (ca. 10-15%). This genomic DNA reduction is due to the low diffusivity of *E. coli* genomic DNA relative to plasmid DNA. Since *E. coli* genomic DNA is ~400 kb and a typical plasmid DNA molecule is ~10 kb, the difference in mass drives the drastically different diffusivities. When the DNA is denatured under basic conditions, the plasmid DNA can quickly reanneal while genomic DNA cannot, resulting in secondary interactions with cell debris and a reduction in overall genomic DNA levels.

TABLE 1 qPCR results for 4.3 L lysis.

| Description | Total DNA conc.* (g/L) | Volume (L) | Plasmid DNA mass (g) | Gen. DNA conc. (μg/mL) | Gen. DNA (%) | Gen. DNA reduction (%) |
|---|---|---|---|---|---|---|
| $OD_{600}$ 70 lysate | 0.96 | 4.3 | 4.1 | 64.2 ± 13.1 | 6.3 ± 1.3 | — |
| Post pH shift | 0.85 | 4.7 | 4.0 | 20.9 ± 2.1 | 2.4 ± 0.2 | 62 ± 12 |
| Clarified lysate | 0.82 | 4.8 | 3.9 | 18.5 ± 2.8 | 2.2 ± 0.3 | 65 ± 17 |

*Values derived from integrated electrophoretic gel.

The lysis procedure was also performed at the 30-L scale. The result was a yield of 0.74 g/L of total DNA with 87% peak 3, where percent (%) peak 3 is the ratio of two anion-exchange peaks and correlate to the percentage of supercoiled DNA. The correlation follows that the higher the percentage peak 3, the higher the percentage of supercoiled plasmid DNA. Table 2 shows AEX assay results at different steps during the lysis. The last column in Table 2 demonstrates the enhanced DNA concentration attainable with the upstream purification processes described herein. In addition, the clarified lysate had a final turbidity of 12.1 NTU.

TABLE 2

AEX assay results for 30 L lysis.

| Description | Dilution factor used for AEX assay | Total DNA conc. (g/L) | % total DNA in Peak 3 | Peak 3 conc. (g/L) | Total DNA conc. scaled (g plasmid DNA per mL of original lysate) |
|---|---|---|---|---|---|
| OD 70 lysate | 30 | 0.862 | 93.9% | 0.809 | 0.862 |
| Post pH shift | 30 | 0.820 | 74.4% | 0.610 | 0.906 |
| Clarified lysate | 30 | 0.742 | 87.0% | 0.646 | 0.902 |

The new lysis described herein can be performed at a DNA concentration of ~0.9 g/L and an $OD_{600}$ of 70. Thus, this high concentration allows for substantially smaller tanks and requires one fewer large process vessel than heat lysis procedures. This lysis can be preformed at roughly twice the concentration of the prior plasmid DNA production processes, utilizes a single tank, reduces *E. coli* chromosomal DNA levels, and simplifies downstream solids separations via a novel PEG-based flocculation step.

EXAMPLE 3

Final DNA Polishing Process

PEG-Precipitation and Microfiltration of PEG Precipitates

A prior DNA purification process, described in U.S. patent application Ser. No. 09/875,379 (U.S. publication number US2002/0012990), incorporated by reference herein, utilized a ultrafiltration ("UF") step at the end of the process to concentrate a calcium silicate (e.g., LRA) filtrate to ~7+mg/mL DNA, followed by a 10× diafiltration for buffer exchange into formulation buffer, PBS (see FIG. 6A). This final polishing step was satisfactory at volumes of approximately 100 L or less, but larger manufacturing-scale purification processes showed pump sizes and flow rates beginning to reach the limit of technology. In order to avoid these process scale-up issues, the final UF step of the plasmid DNA process has been replaced with a PEG precipitation procedure followed by two separate filtration/diafiltration steps (see FIG. 6B). The first filtration/diafiltration step, comprising microfiltration under tangential flow filtration mode, concentrates the precipitated slurry and clears residual RNA and impurities. The second filtration/diafiltration step displaces the PEG with ethanol and dehydrates the DNA. The final wet product is dried under full vacuum to obtain a fine powder form of DNA. There is no need for sterile filtration after the product is dried due to ethanol addition, as long as this step is performed aseptically. Although the prior polishing process only required two steps, compared to the four steps of new PEG-precipitation process, the PEG process is scalable to manufacturing volumes without compromising product quality or requiring the use of extremely large pumps and flow-rates. The new process also includes an additional purification step to further reduce impurities, whereas the prior process only concentrated the plasmid and provided for buffer exchange. This new unit operation has the ability to reduce residual RNA levels, possibly by 2 logs or more, does not require excessive flow-rates and large pumps, reduces cycle-time, and provides a powdered product, which reduces necessary storage space and possibly provides a more stable product.

DNA solubility iii PEG (kinetics of precipitation)—The concentration of PEG 8000 necessary to completely precipitate plasmid DNA in a post-LRA filtrate was examined under varying temperatures and total DNA concentrations. The DNA concentration was varied between 0.3 and 1.0 mg/mL since this is likely what will be encountered in large-scale purifications procedures. FIG. 7A shows that there is a sharp decrease in solubility of DNA in a solution of PEG 8000 when the PEG concentration is >2% (w/v). There was no effect on DNA solubility due to solution temperature or DNA concentration for the range investigated. The results in FIG. 7A show that DNA is completely precipitated by about 4% PEG 8000; however, a PEG 8000 concentration of 8% was chosen in the remainder of the studies to provide a 2× safety factor.

Different molecular weights of PEG were evaluated to determine if another size polymer might be more suitable for the precipitation. FIG. 7B shows that DNA is completely soluble in 400 MW PEG for the range studied; but as the polymer MW increases, the critical mass of PEG necessary to precipitate DNA decreases. This indicates, for example, that any PEG between MW 3,000 and 10,000 could be used to effectively precipitate DNA, with the PEG concentration adjusted accordingly.

Figure 8:
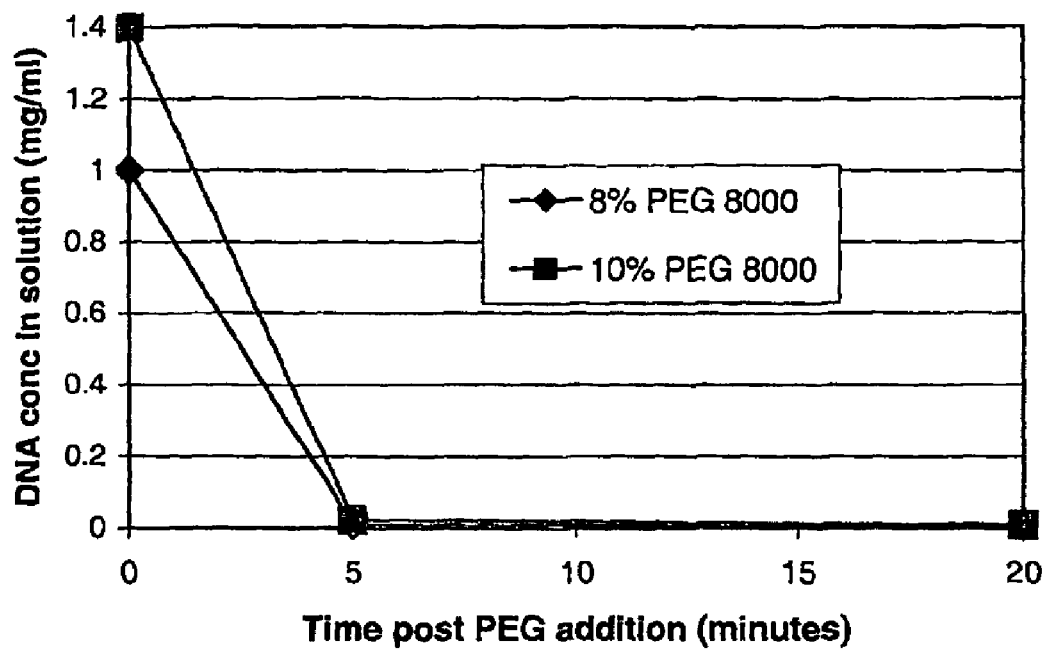
FIG. 8 depicts the kinetics of DNA precipitation in a PEG 8000 solution.

The kinetics of PEG precipitation was investigated to ensure that a 2 hour hold time after PEG addition is sufficient to complete DNA precipitation. FIG. 8 shows that after about 5 minutes, greater than 99% of the DNA is precipitated, indicating that a 2 hour hold time is more than sufficient.

Experimental procedure—The following polishing procedure was developed to further purify plasmid DNA by removing residual RNA and other soluble impurities, resulting in a final powdered product consisting of supercoiled DNA and some residual salts. The powdered product can be resuspended in a liquid formulation.

The starting solution used to demonstrate the novel, downstream concentration/polishing process of the present invention is a post-LRA filtrate, as described in U.S. patent application Ser. No. 09/875,379 (supra). The composition of the solution is 3 M NaCl, 1.0 mg/mL purified DNA and some residual RNA. PEG 8000 MW (Fluka) was used to precipitate the DNA, although MW ranges from 3000-10,000 have been examined. The post LRA filtrate was first warmed to 20° C. and agitated with a stir bar at moderate speed (50 rpm). PEG 8000 was added as a concentrated stock solution of 33% (w/v), over 15 minutes until the final solution concentration was 8% (w/v). The precipitate was aged for 2 hours and then concentrated using a 0.45-micron, hollow fiber membrane, tangential flow filter from Amersham Biosciences. The loading on the membrane was 180 g DNA/$m^2$ of membrane area. The recirculation rate was 9 L/$m^2$/min, and the flux was controlled at 2.5 L/$m^2$/min. Permeate was collected until a 20× concentration was achieved, and the concentrated retentate was then diafiltered against 8% (w/v) PEG 8000 in 1.2 M NaCl for 5 diavolumes. This retentate was collected and the membrane washed with 8% (w/v) PEG 8000 in 1.2 M NaCl at a volume of 4.5 L/$m^2$ of membrane. This wash can be combined with the retentate product. The final retentate was adjusted to 50% (v/v) ethanol by subsurface addition of one equivalent volume of 200-proof ethanol over 30 minutes. During the ethanol addition, the precipitated slurry was kept well agitated to avoid the formation of ethanol "hot spots." This solution was concentrated to approximately 30 g/L precipitated DNA slurry in a filter dryer equipped with a 25 micron 316L stainless steel (SS) filter screen and then diafiltered against 200 proof ethanol for 6 diavolumes, flux controlled at 3.2 L/$m^2$/min. Moderate agitation was used during this diafiltration to keep the slurry suspended. Filter loading was 0.3 kg DNA/$m^2$, but this loading should be considered a lower limit since this number was obtained from experiments that were performed using an under-loaded filter. Following the filtration, the powder was dried under vacuum for 24 hours at 25-37° C.

Analytical methods—DNA concentration was obtained by UV spectroscopy at wavelengths 260, 280, and 320 nm. DNA has an extinction coefficient of 50 $(\mu g/mL)^{-1}$ $(cm)^{-1}$ per 1 absorbance unit at the 260 nm wavelength. The ratio of 260/280 nm was taken to evaluate purity. Sample (500 μL) was loaded into a quartz micro cuvette with a 1 cm pathlength. PEG concentration was evaluated using Fourier Transform Infrared Spectroscopy ("FTIR"). RNA concentration was evaluated by RiboGreen assay.

Concentration of PEG-precipitated slurry (first filtration diafiltration step comprising microfiltration under TFF)—After PEG precipitation, a first concentration step via microfiltration in a tangential flow filtration ("TFF") mode, followed by diafiltration (see FIG. 6B), was used to reduce the working volume of the product and remove any residual RNA and non-product soluble matter left in solution after precipitation. The diafiltration buffer should have appropriate PEG and salt concentrations to ensure the plasmid DNA remains precipitated during diafiltration. For example, plasmid DNA will remain precipitated if the diafiltration buffer contains approximately the same percentage of PEG used in the prior precipitation step (e.g., 8% w/v PEG in the example above) and approximately 1.2 M NaCl. In the example conditions above, if the NaCl concentration drops too far below 1.2 M, additional PEG may be necessary to keep the DNA precipitated. Experiments have shown that a minimum required salt concentration between 100 and 600 mM NaCl is necessary to keep DNA precipitated in a 50% (v/v) ethanol solution. Thus, in order to operate near the upper 600 mM NaCl limit, the salt concentration after the first diafiltration needs to be at least 1.2 M NaCl. The value of 1.2 M NaCl also works well for the subsequent ethanol addition step.

PEG precipitation followed by the microfiltration/diafiltration step described herein shows a considerable reduction in RNA. Table 3 shows the RNA clearance over the first diafiltration step against 8% PEG in 1.2 M NaCl of the purification process described above. Table 4 shows the total clearance across the PEG precipitation step. Table 3 shows that most of the RNA is cleared after the initial diavolumes and is below the quantifiable limit by the third volume. Table 4 shows that the residual RNA is reduced by almost 2 logs. This reduction would probably be greater if the feed concentration of RNA were higher. The final product RNA concentration was near the L.O.D.

TABLE 3

Clearance of RNA during first diafiltration

| | RNA concentration (µg/mL) |
|---|---|
| Post-LRA Filtrate | 37.1 |
| Permeate Diavolume 1X | 3.136 |
| Permeate Diavolume 2X | 0.948 |
| Permeate Diavolume 3X | <0.8** |
| Permeate Diavolume 4X | <0.8** |
| Permeate Diavolume 5X | <0.8** |
| Permeate Diavolume 6X | <0.8** |
| Final Product | 1.12 |

**Below limit of detection.

TABLE 4

Percent RNA comparison between Feed to PEG step and final product

| | DNA concentration (mg/mL) | % RNA |
|---|---|---|
| Post-LRA Filtrate | 7.1 | 0.523 |
| Final Product* | 4.94 | 0.023 |

*The post-LRA filtrate was taken from a previous run diluted into 3M NaCl and used to approximate LRA filtrate.

PEG clearance (second filtration/diafiltration step)—After the first filtration (i.e., microfiltration) and diafiltration step against PEG and NaCl to concentration the plasmid DNA and remove impurities, the plasmid DNA product was adjusted to 50% v/v ethanol by feeding 200-proof ethanol, over 15 minutes. This changes the characteristic of precipitation from a volume exclusion to a dehydration mechanism, changing the physical properties of the precipitated DNA from a gel-like substance to a harder, less compressible precipitate. The resulting precipitate packs into a porous structure resulting in good fluxes and high loading capacities in the second filtration step. Different ethanol concentrations are possible for the adjustment step, but an ethanol concentration within the range between about 30-80% v/v is preferred. Concentrations below 30% risk redissolving DNA back into solution; while concentrations above 80% start to precipitate salts along with the DNA.

A second filtration step, followed by diafiltration against 200-proof ethanol (see FIG. 6B), was used to remove any remaining PEG in solution, to further dehydrate the powder, and to remove as much salt as possible. The ethanol adjusted feed was reduced to a DNA concentration of 50 mg/mL by filtration in a filter dryer system under stirred-cell mode, followed by a 6× diafiltration against 200-proof ethanol. In the example above, the filter loading was 0.3 kg DNA/m$^2$; however, this loading is considered a lower limit since the filter set-up used was under-loaded. Flux through the filter was controlled at 3.2 L/m$^2$/min. When final PEG concentration was assayed by FTIR, all readings were below the limit of detection (<0.05% PEG). The wet powder was then removed and vacuum dried at 25-37° C. If excess salt remains in the dried product, it will become hard and glossy, leaving it very difficult to redissolve. Final yields for tested plasmid DNA have been >90% with purities of approximately 90% DNA, 5% NaCl, residual water, residual EtOH, and possibly residual PEG.

EXAMPLE 4

Plasmid DNA Precipitation with Alcohol

Materials and methods—The plasmid DNA used for the following experiments was purified as per the methods described in U.S. patent application Ser. No. 09/875,379 (supra) and then diluted to the indicated concentration. Ethanol, methanol, isopropyl alcohol, sodium chloride and sodium acetate were purchased from Fisher. Plasmid solubility data was obtained in vortex-mixed test tube experiments. After the precipitating agent was added to the plasmid solution, supernatant samples were taken using syringe filters, and the concentration of plasmid in the filtered sample was measured with a UV plate reader by Molecular Devices. Because alcohols absorb UV light, all samples containing alcohol were dried using a SpeedVac and redissolved in water before measurement. Sodium chloride ion concentration was determined by titrating with silver nitrate, using dichlorofluorescein as the indicator.

Plasmid precipitation with ethanol—FIG. 9A shows plasmid DNA solubility data collected at NaCl feed concentrations between 1.8 and 3.4 M, at ethanol levels of 33, 50 and 67 percent. A sharp solubility decrease occurred between 30 and 33 percent ethanol. At 30% ethanol, plasmid did not precipitate at the salt concentrations used. At 33% ethanol and higher, solubilities corresponded to precipitation yields of approximately 99 percent for an initial plasmid concentration of 0.5 g/L. All NaCl concentrations are reported on a pre-ethanol basis, meaning that the concentration of NaCl in the final solution was lower than that reported. FIG. 9A shows there is little effect of NaCl on plasmid solubility at pre-ethanol concentrations of 1.8 to 3.4 M. However, it was observed that when no NaCl was used, ethanol concentrations in excess of 70% were required to begin precipitating plasmid from solution using a 1.0 g/L feedstock. Thus, NaCl clearly plays a role in plasmid solubility.

Figure 10:
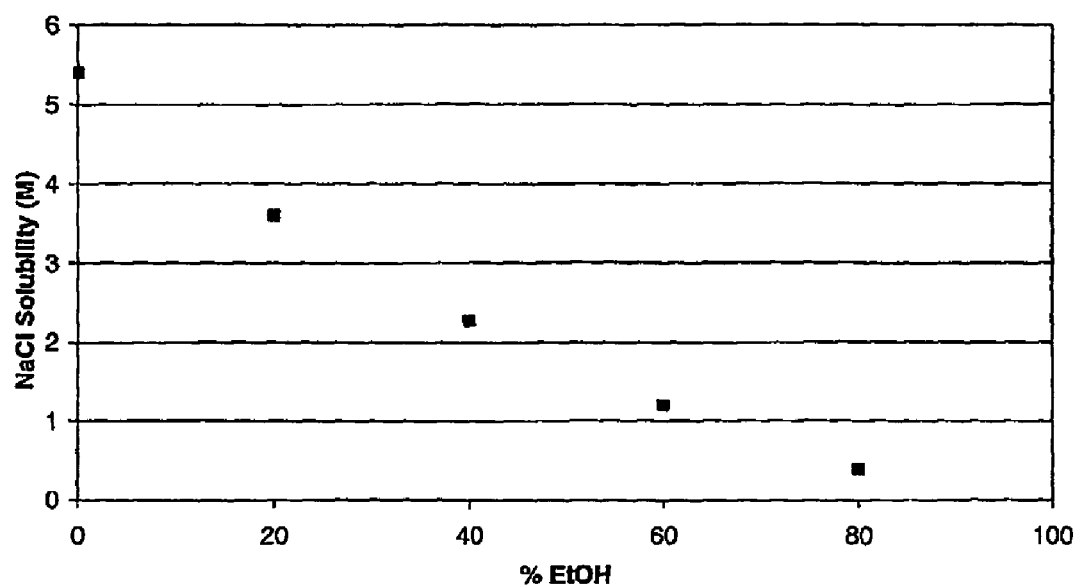
FIG. 10 shows the solubility of NaCl at various ethanol concentrations.

To explore this further, lower concentrations of NaCl were used with various concentrations of ethanol. The results are summarized in FIG. 9B. The dashed line represents the plasmid concentration that would be present for each solution if no precipitation occurred. This value varies with the ethanol level because the feed plasmid concentration remains constant. A clear "salting out" effect is observed. The results of FIG. 9B pose a concern for washing salt from filtered DNA. For example, if a plug type wash is poorly distributed, a combination of low salt and low alcohol could occur, redissolving plasmid. To aid the development of wash protocols that remove sodium chloride without dissolving plasmid, the solubility of NaCl at various ethanol compositions was measured. This data is shown in FIG. 10.

Plasmid precipitation with isopropanol ("IPA")—Table 5 summarizes all solubility data collected for experiments testing the limits of an IPA-NaCl system. NaCl concentrations are reported on a pre-alcohol basis. Conditions for which a yield in excess of 95% is observed are highlighted in gray. It is evident that increasing alcohol or salt concentration initially caused a decrease in plasmid solubility. At high alcohol or salt concentrations, however, further addition caused solubility to increase.

TABLE 6

Plasmid solubility in methanol-water mixtures. Plasmid was fully soluble at 50 percent methanol and lower.

| Percent Methanol | [NaCl], Pre-Methanol | Plasmid Solubility | Yield with 0.5 g/L Plasmid Feed |
|---|---|---|---|
| 67 | 1.8 M | 0.102 g/L | 38.7% |
| 67 | 2.6 M | 0.028 g/L | 82.9% |
| 67 | 3.4 M | 0.0023 g/L | 98.6% |

Summary of alcohol precipitation experiments—When adding ethanol to plasmid solutions containing 3 M NaCl, a sharp decrease in plasmid solubility occurs between ethanol concentrations of 30 and 33 percent. At 33% ethanol and higher, solubility based yields for 0.5 g/L plasmid solutions are approximately 99 percent. In water-ethanol mixtures, increasing concentrations of NaCl reduces solubility of plasmid (i.e., "salting out"). In water-IPA mixtures, addition of salt beyond the salting out concentration causes solubility to increase ("salting in"). When kosmotropic sodium acetate was substituted, both salting out and salting in effects were

TABLE 5

Measured solubility of DNA plasmid in IPA-water mixtures with NaCl.

| % IPA | Expected Plasmid Conc. (g/L) | NaCl concentration (molarity, pre-NaCl basis) | | | | | | | | | |
|---|---|---|---|---|---|---|---|---|---|---|---|
| | | 0 | 0.1 | 0.5 | 1 | 1.8 | 2 | 2.6 | 3 | 3.4 | 4 |
| | | Measured Plasmid Conc. (g/L) | | | | | | | | | |
| 10 | 0.45 | | | | 0.331 | | 0.284 | | 0.398 | | |
| 25 | 0.375 | | 0.368 | 0.250 | 0.015 | | .0042 | | .0056 | | 0.365 |
| 33 | 0.335 | 0.293 | 0.337 | .0084 | .0031 | .0013 | | .0014 | | 0.333 | |
| 50 | 0.25 | | .0047 | .0021 | .0017 | .0017 | .0041 | .0025 | | 0.245 | |
| 67 | 0.165 | | .0019 | | | 0.166 | | 0.164 | | 0.165 | |

Figure 11:
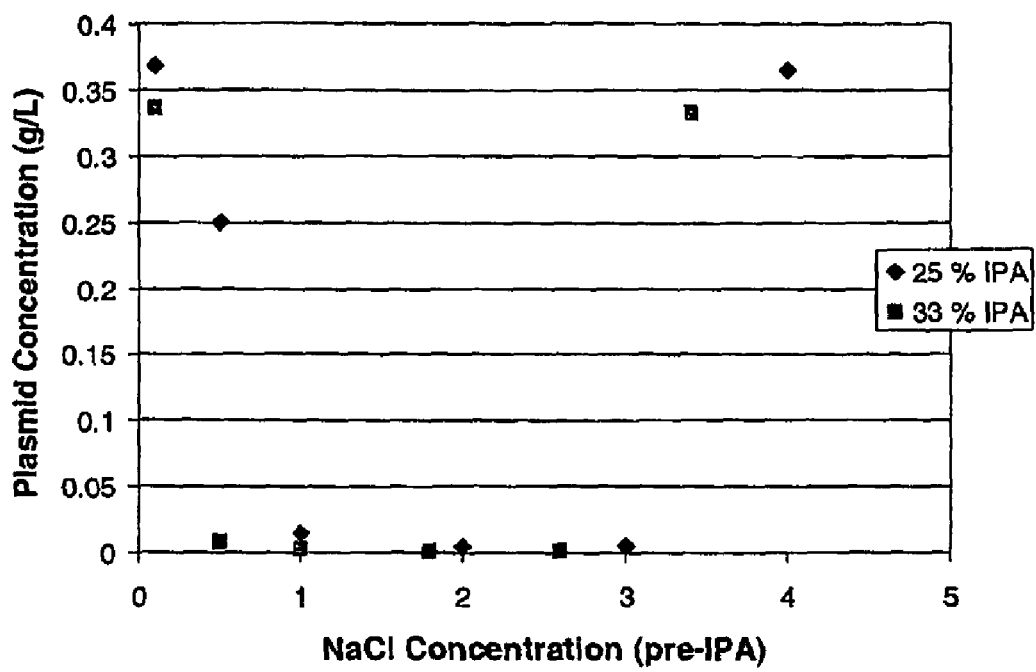
FIG. 11 illustrates the extremes of "salting out" and "salting in" for IPA-NaCl systems at two IPA concentrations.

FIG. 11 illustrates the extremes of "salting out" and "salting in" for EPA-NaCl systems at two IPA concentrations. The figure shows the effect of salt only; however, Table 5 shows that this effect is also achieved for EPA at constant salt concentration. These results are analogous to protein precipitation, where electrostatic shielding causes "salting out" but chaotropes at sufficient concentrations cause "salting in." This indicates that DNA precipitation is the result of intermolecular, hydrophobic interactions between base pairs. To compare with results obtained using the mildly chaotropic NaCl, the solubility of plasmid in IPA with sodium acetate, a kosmotrope, was determined at various conditions. FIGS. 12A and 12B summarize the results of this experiment. At 67 percent ethanol, the presence of sodium acetate decreases plasmid solubility; however, at other points, plasmid solubility is actually higher with sodium acetate than with an equal concentration of NaCl.

Plasmid precipitation with methanol—Methanol concentrations of 33% and 50% in combination with 1-3 M NaCl failed to precipitate plasmid. This makes methanol undesirable for process use, but it was able to precipitate plasmid at 67%. Table 6 displays these results. The "salting out" phenomenon is clearly evident.

diminished. Methanol has the ability to precipitate plasmid from strong salt solutions, but requires a solvent level in excess of 50%.

EXAMPLE 5

Final DNA Polishing Process: Alcohol Precipitation

As shown above, PEG precipitation of plasmid DNA and microfiltration in TFF mode is a viable option to replace ultrafiltration of in the final concentration/polishing step of large-scale plasmid DNA purification processes. Earlier development work described in U.S. patent application Ser. No. 09/875,379 (supra) showed that ethanol could be utilized as a precipitation solvent to gain a dry powder form of plasmid DNA. However, rates were slow and extreme compaction of the cake was evident unless a gradual wash gradient was applied. This Example describes a process to create a purified bulk powder form of plasmid DNA featuring alcohol precipitation augmented by microfiltration. As an enhancement of this approach, continuous precipitation with concurrent microfiltration may significantly reduce vessel volumes relative to the batch method.

Materials and methods—See "Materials and Methods" in Example 4. Pellicon XL microfiltration cartridges, accompanying pressure gauges, and 0.45 μm syringe filters were purchased from Millipore. Vacuum filtration apparatus and membranes were purchased from Fisher.

Stepwise filtration/diafiltration process to make bulk plasmid powder—Once solubility data established the required conditions for plasmid precipitation, collection of precipitated powder by filtration was attempted. Ethanol was chosen as the optimal solvent for precipitation due to its low volume requirement relative to methanol and its robustness relative to IPA.

Figure 13:
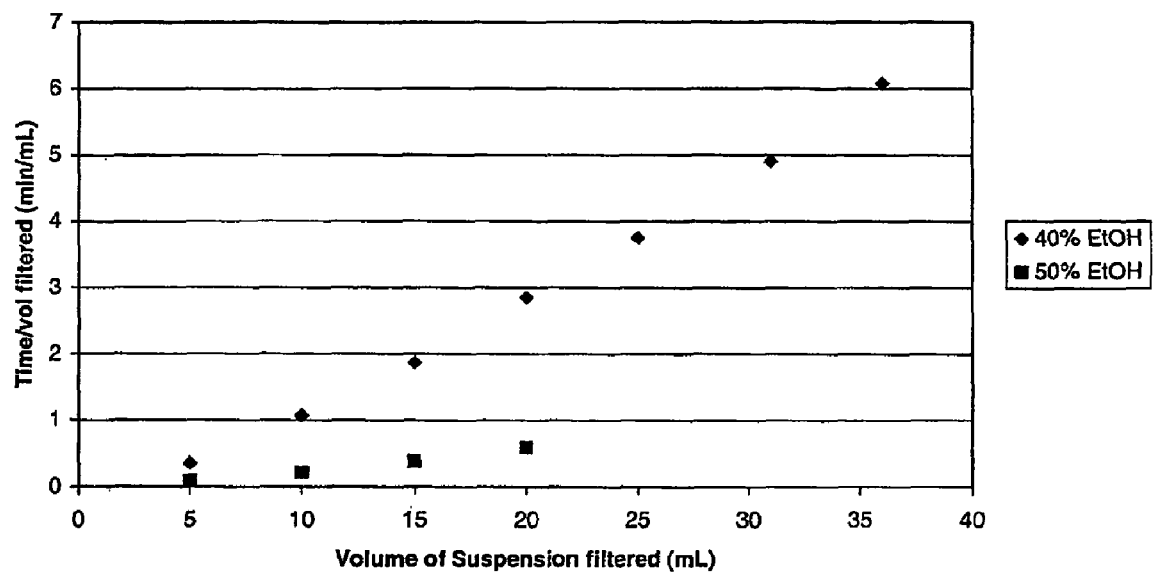
FIG. 13 shows a $V_{max}$ plot of dead-end filtration data for plasmid DNA precipitated from a 3 M NaCl solution (0.22 micron cellulose membrane, 2.1 cm² filtration area, 20 in. Hg vacuum). This filtration data was first retrieved from an original 40% ethanol concentration, and then again after ethanol had been added to produce a concentration of 50%. The relatively straight lines in the t/V versus V plot indicate a nearly incompressible cake. A significantly higher filtration rate with 50% ethanol is observed.

In a first attempt to filter precipitated plasmid, 134 mL of ethanol was slowly added to 200 mL of a post-LRA filtrate solution containing 0.86 g/L plasmid and 3 M NaCl, to produce a final concentration of 40% v/v ethanol. Filtration was attempted using a sidearm flask and a 0.2 micron membrane filter, with 2.1 cm$^2$ of filter area. The sidearm flask was supplied with 20 inches of vacuum. The initial filtration attempt showed a significant decrease in flux as filtration progressed, and a gel-like filter cake was formed. The filter used was a Fisherbrand membrane composed of cellulose acetate and cellulose nitrate. FIG. 13 shows filtration data collected during experiments using this suspension. Data was taken at the original 40% v/v ethanol concentration, and again after ethanol had been added to produce a concentration of 50% v/v. The relatively straight lines in the time/volume (t/V) versus volume (V) plot indicate a nearly incompressible cake. A significantly higher filtration rate with 50% ethanol is observed. This data was used to estimate the time required for a large scale batch filtration using a filter 5 feet in diameter (19.6 ft$^2$ membrane area). The calculated estimate is 243 hours using 40% ethanol and 44 hours using 50% v/v ethanol. Because of these impractical filtration times, a high-area, tangential flow filtration ("TFF") membrane was considered as an alternative method.

The first attempts at microfiltration of precipitated plasmid used a Millipore Pellicon XL TFF cartridge with a 0.22-μm PVDF membrane. Precipitation was achieved by the slow addition of ethanol to a stirred plasmid solution in a baffled glass mixing vessel, reaching a concentration of 40% v/v ethanol. The initial NaCl concentration of the plasmid solution was 3 M. After adding the precipitating agent over a two hour period and allowing approximately 30 minutes of age time, microfiltration was attempted using a recirculation flow-rate of 30 mL/min. FIG. 14A shows permeate volumes collected over time. The initial concentration of DNA in the precipitated suspension is also shown for each data set. The suspensions filtered easily at 15 mL/min, with no decrease in permeate flux over the course of the experiment. A feed pressure gauge maintained readings of about 10 psig throughout the filtration. This result indicates that solids were freely removed from the membrane surface and did not form a cake layer. The initial suspension volume was 500 mL in each case.

In order to dehydrate the slurry, making it suitable for filtration and drying, the concentrated suspensions were subsequently diafiltered against high concentrations of ethanol. This diafiltration also removes any NaCl prior to isolation and drying in a filter dryer. Because plasmid is insoluble in 80% v/v ethanol solutions, diafiltration with 80% v/v ethanol can be used to remove NaCl from the suspension while maintaining conditions in which plasmid is insoluble. FIG. 14B shows the ethanol and salt concentrations during diafiltration; FIG. 9B shows that the small amount of salt remaining before the ethanol concentration approaches 80% v/v will keep plasmid from resolubilizing. The NaCl solubility at the ethanol concentrations throughout the filtration is also shown. In diafiltrations of precipitated suspensions, permeate flux remained constant at about 15 mL/min.

In the first attempt to create a dry powder, a plasmid suspension was diafiltered against two volumes of 80% v/v ethanol after concentrating to about 4 g/L DNA. Solids were then collected by vacuum filtration on a 25-mm diameter, 0.2 micron PES membrane. After overnight drying, the product had a rock-like appearance, due to the ethanol/water azeotrope at 89.4% ethanol. Because the wet cake ethanol concentration was less than the azeotropic composition, the water composition was enriched during drying, causing solids to agglomerate. A subsequent formulation attempt also used diafiltration with 80% v/v ethanol followed by filtration, but then added several cake diafiltration washes with pure ethanol to displace the 80% v/v ethanol remaining in the cake. The washes ensured that the ethanol level in the wet cake would exceed the azeotropic composition prior to drying. The powder was vacuum dried overnight at 37° C. The remaining material was a dry, free flowing white powder. Redissolving the material in water and measuring the absorbance at 260 nm indicated that the powder was 97% pure. The yield for the precipitation and microfiltration was 93%.

Summary—Vacuum filtration of plasmid precipitated using ethanol (40-50% v/v) afforded a nearly incompressible, albeit gel-like, cake; however, filtration rates were unacceptably slow, indicating the need for tangential flow filtration. Tangential flow microfiltration was successfully employed to concentrate and then dehydrate (by alcohol diafiltration) the precipitated plasmid. Dead end filtration and washing of the alcohol-rich slurry became practical, affording a free flowing powder by vacuum drying. Yield for the combined steps of precipitation, microfiltration, recovery and drying was 93%, and solids were 97% pure (by $A_{260}$). Based on fluxes observed at lab scale, this process could be performed for a 40,000 L batch in 8 hours using 215 ft$^2$ of membrane area.

EXAMPLE 6

Continuous Alcohol Precipitation and Microfiltration of Plasmid DNA: Reduced Vessel and Alcohol Volumes Plasmid precipitation in batch mode requires a vessel large enough to hold both the batch volume and the amount of ethanol required for precipitation. If both feed and ethanol could be continuously pumped into a smaller, intermediate container from which microfiltration simultaneously removes liquors to maintain a constant volume, the large precipitation vessel would no longer be needed, even if precipitation were conducted at high solvent ratios. In this mode, solvent waste could be minimized by continuously distilling the permeate and recycling to the precipitation vessel.

The continuous precipitation/microfiltration approach, without ethanol recovery, was first attempted using both ultrafiltration and microfiltration membranes. In these experiments, an initial 500 mL precipitated suspension was made by slowly adding ethanol to a feed solution in a stirred vessel to reach an ethanol concentration of approximately 40% v/v. The particles were allowed to fully dehydrate over about 30 minutes. Microfiltration of the resulting suspension was performed using a Pellicon XL TFF cartridge with 50 cm$^2$ of filtration area. Once the volume of the suspension was reduced to about 300 mL, feed and ethanol solutions were added in to keep the volume of the suspension constant. FIG. 15A shows data for a continuous precipitation/microfiltration using a 100 kD PES membrane. The feed flow-rate to the filtration cartridge was 30 mL/min. As the figure shows, after about 200 mL of permeate had been collected during the continuous process, the flux had decreased to about 20% of its initial value. A similar flux decline was observed in an attempt using a 0.22-μm cartridge. A transcartridge pressure rise was visible immediately after addition began. This increase in pressure is absent in observed batch microfiltration. These attempts used flexible Masterflex size 14 tubing, 5/16" inner diameter, to add feed and ethanol during filtration. This flexible tubing was larger than the narrow tubing used for batch precipitation.

Because it appears that dehydration time is necessary before microfiltration can be successfully conducted, a holdup volume between the vessel and filter may improve filtration rates by creating a lag time in which particles can dry out before reaching the membrane. This theory was tested at lab scale by inserting a length of tubing between the precipitation vessel and filter to create a one minute lag time at a flow-rate of 30 mL/min. FIG. 15B shows data for a trial which incorporated the one minute lag time between vessel and filter. This trial also used 40% v/v ethanol and a feed pump set to 30 mL/min; however, a 0.1 micron PVDF membrane was used in this case. It is evident that the process with lag time shows a smaller percentage loss in flux than seen in FIG. 15A over a permeate volume of 200 mL. However, the initial rate is slower than for the data in FIG. 15A. It is possible that the length of tubing used to create the lag time may have resulted in a frictional resistance that caused peristaltic pump slippage and decreased the flow-rate coming from the stirred vessel. A rapid transcartridge pressure increase is again observed for this attempt, which also used Masterflex size 14 tubing for feed and ethanol addition during filtration.

FIG. 15C shows data for an experiment that used the same lag time setup as FIG. 15B while increasing the ethanol concentration to 50% v/v. In this trial, permeate flux slowdown was lessened somewhat from the 40% v/v ethanol trial, but the pressure increase was even more dramatic. Filtration was stopped after only 30 minutes when it became unfeasible due to the pressure increase. This attempt also used Masterflex size 14 tubing for feed and ethanol addition during filtration.

The rapid pressure increases in FIGS. 15A-C are an issue for the feasibility of the semicontinuous precipitation/microfiltration process. Even if permeate rates are acceptable, pressure increases caused by channel plugging could force filtration to be terminated before the desired slurry concentration has been achieved. It seems likely that channel plugging is caused by large, hydrated particles. In an attempt to create smaller particles during the continuous approach, narrow HPLC tubing was used for feed and ethanol addition during filtration, instead of the 5/16" Masterflex tubing used in previous experiments. FIG. 16A shows data for a trial which used HPLC tubing for feed and ethanol addition, with 40% v/v ethanol and no lag time. The transcartridge pressure increase is less dramatic than in previous experiments, and the relative flux decrease is improved compared to the previous experiment with no lag time, shown in FIG. 15A. It seems that the higher linear velocity exiting narrow tubing causes a finer alcohol dispersion into the plasmid solution, thereby avoiding local excesses of alcohol. Non-uniform alcohol composition will lead to precipitation and rehydration sequences, creating large, sticky particles which may plug membrane channels. FIG. 16B shows data for a similar attempt with 50% v/v ethanol. The rate of permeate flux slowdown is much slower than in FIG. 16A due to the faster dehydration at 50% v/v ethanol. The improved performance at higher solvent concentration bodes well for other products that use high quantities of ethanol for precipitation.

Summary—The size of the plasmid precipitation vessel could be reduced by a continuous process in which ethanol and plasmid solution are added continuously to a stirred vessel while microfiltration is conducted simultaneously from the same vessel, maintaining constant volume. As an adjunct to this approach, continuous distillation of the permeate provides recycling of enriched ethanol to the precipitation, minimizing the required solvent volume and permitting precipitation at higher and even more favorable alcohol concentrations. In experimental runs of continuous precipitation/filtration with both microfiltration and ultrafiltration membranes, permeate fluxes declined and then attained a steady rate, in contrast to the constant permeate fluxes obtained subsequent to batch precipitation. Increases in transcartridge pressure were also observed, in contrast to the batch case. Particle size monitoring of batch precipitation by LASENTEC indicates that, subsequent to alcohol addition, an age time of about 15 minutes is required for particles to increase to an equilibrium size, likely reflecting the simultaneous events of aggregation and dehydration. Failure to provide this age time in the continuous approach could explain the declining flux values since some newly formed, pore fouling particles are withdrawn immediately to the tangential filter. The addition of a one minute holdup volume to permit particle aging between vessel and filter in the continuous precipitation/microfiltration approach improved permeate fluxes. The use of smaller-diameter tubing for feed and ethanol addition during the semicontinuous approach also decreased transcartridge pressure and improved flux. The higher linear velocity of liquid exiting the narrower tube mouth likely improves the dispersion of ethanol and feed into the bulk suspension, thereby affording more uniform, smaller particles that dehydrate quickly and do not clog membrane channels.

EXAMPLE 7

Shear on pH Shifted DNA Lysates

Materials & methods—In a 7 L jacketed glass vessel, 2 L of $OD_{600}$=300 *E. coli* cells containing supercoiled plasmid DNA of interest were resuspended to $OD_{600}$=70 in STET buffer. To this, 500 units/mL of recombinant lysozyme was added and heated to 37±2° C. The harvested cells were incubated in this lysis buffer for at least 2 hours. Approximately 5 L of material was removed for additional studies; and utilizing the remaining 4.7 liters, the lysate was exposed to increasing shear rates with tip speeds from 300 to 2000 ft/min. At each tip speed, the material was held for 10 minutes prior to increasing the speed—up to the final 2000 ft/min tip speed. Finally, the tip speed was reduced to 300 ft/min, and the pH 12 lysate was mixed overnight.

Results—To gauge potential degradation issues with the implementation of the upstream lysis/lysate clarification process of the present invention (i.e., lysozyme lysis/pH shift/ PEG flocculation), the shear sensitivity of a pH 12 lysate exposed to a variety of tip speeds was determined. Table 7 shows the results quantifying the DNA concentration (g/L) and percent supercoiled plasmid DNA content ("% SC") as determined by a 0.8% agarose gel. A high total DNA concentration and percent of supercoiled plasmid DNA was maintained as the tip seed was increased up to 2000 ft/min. Thus, no damage to the plasmid DNA was recorded at tip speeds up to 2000 ft/min, indicating that the lysis technology disclosed as part of the present invention is sufficient to lyse host bacterial cells without shearing DNA in the lysis vessel.

TABLE 7

Data from pH shifted lysate shear study.

| Tip Speed (ft/min) | RPM | Sampling Time | DNA Conc. (g/L) | % SC from Gel |
|---|---|---|---|---|
| 300 | 255 | 0 min | 0.51 | 51.7% |
| 500 | 425 | 11 min | 0.51 | 54.0% |
| 700 | 594 | 22 min | 0.56 | — |
| 900 | 764 | 33.3 min | 0.60 | 64.2% |
| 1100 | 934 | 44 min | 0.64 | 67.3% |
| 1300 | 1104 | 55.7 min | 0.67 | 72.9% |
| 1500 | 1274 | 67 min | 0.69 | 74.5% |
| 2000 | 1699 | 78 min | 0.67 | 77.3% |
| overnight | 255 | ~16 hr | 0.52 | 60.6% |

EXAMPLE 8

Purification of Plasmid DNA

Lysis/lysate clarification—*E. coli* cells containing a plasmid DNA of interest is first resuspended in a STET buffer (50 mM Tris, 100 mM EDTA, 2% Triton X-100, and 8% w/v sucrose, pH 8.2) to an $OD_{600}$ of ~70. Recombinant lysozyme is added at 1167 U/mL (Epicentre technologies), and mixture is first brought to 37±5° C. and then incubated for 2 hours. After incubation is complete, 5 N NaOH is added to the lysate to a final concentration of 0.24 N over 1 hour and allowed to incubate for 1 hour. The solution is returned to pH 8.0±1.0 by adding 2.5 N acetic acid over 0.5-1 hour. The lysate is then flocculated with PEG 6000, added in a 50% w/v slurry (in 150 mM NaCl) to 3.7% w/v over 1 hour. Clarification of the flocculated lysate is performed by centrifugation (e.g., a Sharples AS26 centrifuge) to remove flocculated cell debris, although batch centrifugation is also an option. Post centrifugation turbidities are <30 NTU. If lower post centrifugations are desired, a polish filtration can be used to help remove remaining cell debris. For example, a 12-inch Cuno filtration housing with a Millipore DE40 or CE50 depth filter at a loading of approximately 70 $L/m^2$ can be used to achieve below 10 NTU turbidities.

Additionally, a CTAB low-cut precipitation step can be performed to about 0.15% (w/v) to remove soluble protein and endotoxin, especially if a downstream LRA11 filtration is performed. This can be done by adding 2% (w/v) CTAB in 40 mM NaCl to the flocculated lysate over 1 hour to prevent host spot filtration. The material is then ready for clarification as described above.

CTAB Precipitation—The supercoiled plasmid DNA is precipitated from the clarified host cell lysate with a single 0.50% w/v CTAB-induced precipitation step in the presence of 10 g/L Celpure P300 (diatomaceous earth). A 2% w/v CTAB solution in 40 mM NaCl is added to the clarified lysate over 2 hours to prevent hot spot formation. The lysate is filtered, and the filter cake is first washed with a quarter of the batch volume of 5% IPA with 50 mM NaCl. The filter cake is then washed with one tenth of the batch volume of 50 mM NaCl. Micelles of CTAB and Triton® X-100 are responsible for DNA precipitation. The enhanced selectivity of the CTAB/Triton X-100 micelles for plasmid DNA, over free CTAB, is due to the alignment of CTAB charges in the micelle with the spacing of phosphate charges on the backbone of double-stranded DNA. The washed cake is then taken to the redissolution step.

Redissolution and calcium silicate batch adsorption—Redissolution entails manually removing the CTAB-precipitated DNA-containing cake from the stirred filter tank. This cake is then resuspended in 3 M NaCl, targeting a 1.2 g/L DNA concentration (wherein said target DNA concentration can range from about 0.3 to about 1.2 g/L). The initial 3 M NaCl charge contains 25 g LRAII/g DNA and is incubated for a minimum of 4 hours. This initial LRA11 incubation can be performed in a stepwise process wherein a initial charge of 12.5 g LRAII/g DNA is incubated for a minimum of 4 hours, followed by a second 12.5 g LRAII/g DNA charge that is incubated for additional time (minimum of 6 hours). The resuspended material is then assayed for concentration (e.g., AEX assay) and by gel electrophoresis (E-gel run at 60V for 30-50 minutes). After this initial incubation step, 0.5-0.75 g LRAII/g DNA is added for every percentage supercoiling point below 85% SC by E-gel electrophoresis. This mixture is allowed to sit overnight, and the bulk will be assayed again for concentration and supercoiled percentage. If the material is >85% SC, filtration commences; and if not, more LRAII is added.

The redissolved plasmid DNA solution is filtered using a Cuno 12 inch housing (4-high) with a membrane area proportionate to the total amount of Celpure and LRAII in the bulk solution. Generally, 1 gram of Celpure or LRAII takes up to ~4 mL of volume. Based on the total amount of LRA and Celpure the proper number of Millipore CE50 depth filtration cartridges (Twelve inch round, 6 cell) are utilized in the above Cuno filter housing. After filtration is complete, a sufficient amount of 3 M NaCl is charged to fill the housing and recirculate for 30 minutes. This material is conserved, and the wash is repeated. These wash steps are to recover the large percentage of plasmid DNA entrained with the Celpure and LRAII cake. The material is then placed into another tank for a second LRAII treatment.

Second calcium silicate batch adsorption—A second LRAII incubation is performed to assure substantial removal of residual *E. coli* host cell DNA. Approximately 10 g LRAII/g DNA is added to the plasmid solution and incubated for 4 hours. The solution is then assayed by gel electrophoresis (E-gel 60 V for 30-50 minutes) and charged with LRAII at 2 g/g DNA every 2 hours until >90% supercoiled plasmid DNA purity is reached, assaying prior to each subsequent addition. Filtration if this second LRAII step utilizes a 1-2 Millipore Series 2000 housing that holds a single, 30", 0.45 μm Durapore filter, having adequate cake capacity and preventing the bypass of hydrated calcium silicate into downstream steps.

PEG-based precipitation and ethanol powdering—A precipitation step by addition of polyethylene glycol (PEG) followed by two separate filtration/diafiltration steps represent the final polishing step in the DNA purification process. A 50% w/v PEG 6000 solution is added to the second LRAII filtrate to a final concentration of 10% w/v, generating a final salt concentration of 1.2 M NaCl. A first filtration step is performed using a hollow fiber MF membrane step, concentrating the precipitated slurry and clearing residual RNA and impurities. The concentrated slurry is then diafiltered against 10% w/v PEG 6000 in 1.2 M NaCl for 5 diavolumes. The retentate is then further concentrated using a second stirred filter vessel-based filtration step. First, the retentate is adjusted to 50% v/v ethanol by subsurface addition of one equivalent volume of 200-proof ethanol over 30 minutes, displacing the PEG with ethanol and dehydrating the DNA dehydrating. The solution is then concentrated in the unit using a stainless steel screen with 25 μm pore size and diafiltered against 200-proof ethanol for 6 diavolumes. The final ethanol precipitated product is dried under vacuum to obtain a fine powder form of DNA. Once the powder bulk is produced, the material can be resuspended (e.g., 5-9 g/L). Sterile filtration of the resuspended DNA solution can be performed using a Millipore Millipak 200 filter (0.22 µm, PVDP) at a loading of approximately 400 grams/square meter at a flow rate of 1500 mL/min/m².

Representative process yields/impurity clearance data—The above process yield for two DNA plasmids, Plasmid A and Plasmid B, generated 17.2 and 19.0 grams of plasmid, respectively (see FIGS. 17A & B). FIG. 17A shows total yield of supercoiled plasmid DNA for both production runs, and FIG. 17B shows the key impurity levels over the course of processing. The assay results demonstrate that all key impurities were reduced below the level of assay quantification.

EXAMPLE 9

Bacterial Cell Harvest Procedure

The goal of a harvest step is to concentrate and wash host cells (including, but not limited to bacterial cells; e.g., *E. coli*) containing a biomolecule of interest (including, but not limited to, supercoiled plasmid DNA) for use in purification. This example describes the harvest of *E. coli* host cells carrying a supercoiled plasmid DNA of interest.

Six by 3.7 m² GE Healthcare (formerly A/G Tech) hollow fiber cartridges with 500 MWCO (UFP-500-E-75) are operated in parallel for a total of 22.2 m². Critical parameters are transmembrane pressure ("TMP"), inlet pressure, crossflow rate, concentration factor, and flux. Culture optical density at harvest ranges from 80-100 $OD_{600}$, and volumetric productivity will be ~1 g plasmid/L. At harvest the fermentor broth is cooled to <10° C. This temperature is maintained throughout the microfiltration and dispensing by cooling on the retentate vessel and/or retentate line. The harvest step is operated by initially maintaining TMP at 10 psig by regulating the retentate backpressure by control valve. The cross-flow rate is set to 50 mL/min/fiber (300 LPM for 22.2 m²). As the batch becomes concentrated, the feed pressure increases. When the feed pressure reaches 25 psig (TMP ~15 psig), the cross-flow rate is reduced as needed to maintain feed pressure of ~25 psig. Concentration factor is based on dry cell weight (DCW) correlated to $OD_{600}$ measurement. A final $OD_{600}$ of 300 is the target for purification. Based on initial culture $OD_{600}$ of 80 to 100 obtained in development runs, a concentration factor of 3-4× will be required.

Concentration is performed until the target concentration factor is achieved or until significant flux decay is observed (in the instance of high biomass culture). A threshold flux level can be defined in order to trigger the end of concentration. At the end of concentration, diafiltration is performed with approximately 4 diavolumes of sodium phosphase solution (RCM635-0.12 M NaCl, 5 mM Sodium Phosphate Dibasic ($Na_2HPO_4$ anhydrous), 1 mM Sodium Phosphate Monobasic ($NaH_2PO_4$ Monohydrate) to wash the concentrated cells. If the target concentration factor was not achieved during concentration, then the batch is further concentrated at the end of diafiltration. Concentration and diafiltration are to be performed in a feed and bleed mode, with a constant liquid level maintained in the retentate vessel by adjusting the feed rate of broth to the tank to compensate for the rate of permeation.

At the end of diafiltration, the cell paste is to be maintained in a well-mixed state at <10° C. during dispensing. Aliquots are dispensed in either 2-L Nalgene bottles or 8-L Stedim bags and frozen to <-60° C. for subsequent storage. A dry ice bath or static freezing in an upright freezer are acceptable freezing methods.

An example of process equipment specifications used for host cell harvest is listed in Table 8. In this example, the 600-L vessel designated as the retentate vessel will limit the amount of material that can be processed. Assuming the minimum concentration factor of 3×, an optimum process volume of ~1200 L of culture could be harvested. This volume ensures sufficient head-space in the tank for an optional dilution of concentrated paste prior to diafiltration. Membrane loading with culture volume of 1200 L would be 54 L/m².

TABLE 8

| Equipment Specifications for DNA Harvest Step | |
|---|---|
| Retentate vessel | 600-L Portable Tank (VE-5140) |
| Retentate vessel working volume | 420 L |
| Filtration Skid | Large Microfiltration Skid (MF-4510) |
| Feed pump maximum* | 420 LPM |
| Membrane holder capacity | 22.2 m² (6 × 3.7 m²) |

*Pump maximum at zero backpressure. Pump capacity will decrease with increasing backpressure It is recommended that the concentration factor for the batch be calculated based on an in-process measure of the broth optical density and a target of $OD_{600}$ of ~300 after concentration. Using this example, an initial culture volume of 1200 L will generate >300 L of cell paste for downstream processing. The batch will first be concentrated at least 3× (or until flux decay is observed in the instance of high biomass culture), then diafiltered with 4 diavolumes of sodium phosphate solution, and finally concentrated to the final target of 300 $OD_{600}$. A minimum of 1600 L of buffer will be required for diafiltration, with an additional 400 L needed for pre-use membrane conditioning.

What is claimed is:

1. A method of purifying supercoiled plasmid DNA from a cell lysate of a large-scale microbial fermentation which comprises:
   (a) lysing microbial host cells containing supercoiled plasmid DNA, forming a host cell lysate;
   (b) clarifying said host cell lysate by flocculating host cell debris with a polymer flocculant wherein said flocculant is at a concentration which does not precipitate said supercoiled plasmid DNA; and,
   (c) removing the flocculated, host cell debris, generating a clarified lysate containing the supercoiled plasmid DNA.

2. A method of claim 1, wherein said polymer flocculant is polyethylene glycol (PEG).

3. A method of claim 2, wherein the host cells in step (a) are lysed in a standard STET buffer containing lysozyme.

4. A method of purifying supercoiled plasmid DNA from a cell lysate of a large-scale microbial fermentation which comprises:
   (a) lysing microbial host cells containing supercoiled plasmid DNA, forming a host cell lysate;
   (b) clarifying said host cell lysate by flocculating host cell debris with PEG wherein said PEG is at a concentration which does not precipitate said supercoiled plasmid DNA; and,
   (c) removing the flocculated, host cell debris, generating a clarified lysate containing the supercoiled plasmid DNA.

5. A method of claim 4, wherein the host cells in step (a) are lysed in a standard STET buffer containing lysozyme.

6. A method of claim 5, wherein the STET buffer contains PEG.

7. A method of claim 4, wherein PEG is added to the host cell lysate after lysis.

8. A method of claim 7, wherein the molecular weight of the PEG flocculant is between about 1450 Da and about 15,000 Da.

9. A method of claim 7, wherein the host cell lysate is subjected to an alkaline pH shift and subsequent neutralization prior to addition of PEG.

10. A method of claim 9, wherein the alkaline pH shift and subsequent neutralization comprises raising the pH of the host cell lysate to an alkaline value of between about pH 12 and about pH 13 and then lowering the pH of said cell lysate to a value of between about pH 7 and about pH 9.

11. A method of claim 7, wherein the host cell lysate is subjected to an alkaline pH shift and subsequent neutralization after addition of PEG.

12. A method of claim 11, wherein the alkaline pH shift and subsequent neutralization comprises raising the pH of the PEG-containing, host cell lysate to an alkaline value of between about pH 12 and about pH 13 and then lowering the pH of said lysate to a value of between about pH 7 and about pH 9.

13. A method of purifying supercoiled plasmid DNA from a cell lysate of a large-scale microbial fermentation which comprises:
    (a) lysing microbial host cells containing supercoiled plasmid DNA in a physiological lysis buffer, forming a host cell lysate;
    (b) subjecting the host cell lysate of step (a) to an alkaline pH shift by raising the pH of said lysate to between about pH 12 and about pH 13;
    (c) neutralizing the alkaline-shifted cell lysate of step (b) to approximately the pH of the lysis buffer;
    (d) clarifying the cell lysate of step (c) by flocculating host cell debris with PEG wherein said PEG is at a concentration which does not precipitate said supercoiled plasmid DNA; and,
    (e) removing said flocculated host cell debris of step (d), obtaining a supernatant containing soluble supercoiled plasmid DNA.

14. A method of claim 13, wherein the physiological lysis buffer of step (a) is a standard STET buffer.

15. A method of claim 13, wherein a detergent-induced precipitation step between steps (d) and (e) is added to precipitate debris and non-supercoiled plasmid, further clarifying the cell lysate.

16. A method of claim 1, wherein the detergent is hexadecyltrimethylammonium bromide (CTAB).

17. A method of purifying supercoiled plasmid DNA from a cell lysate of a large-scale microbial fermentation which comprises:
    (a) lysing microbial host cells containing supercoiled plasmid DNA in a physiological lysis buffer, forming a host cell lysate;
    (b) clarifying said host cell lysate by flocculating host cell debris with a PEG flocculant wherein said PEG flocculant is at a concentration which does not precipitate said supercoiled plasmid DNA;
    (c) precipitating said supercoiled plasmid DNA with PEG; and,
    (d) concentrating said precipitated supercoiled plasmid DNA by microfiltration under a tangential flow filtration mode.

18. A method of claim 17, wherein said host cells in step (a) are lysed in a standard STET buffer.

19. A method of claim 18, wherein the host cell lysate is subjected to an alkaline pH shift and subsequent neutralization prior to addition of the PEG flocculant.

20. A method of claim 19, wherein the alkaline pH shift and subsequent neutralization comprises raising the pH of the host cell lysate to an alkaline value of between about pH 12 and about pH 13 and then lowering the pH of said lysate to approximately its pH prior to the alkaline shift.

21. A method for the purification of supercoiled plasmid DNA from a cell lysate of a large-scale microbial fermentation, which comprises:
    (a) harvesting microbial host cells containing supercoiled plasmid DNA from a fermentation broth;
    (b) lysing the host cells in a sufficient amount of a physiological lysis solution;
    (c) subjecting the host cell lysate to an alkaline pH shift by raising the pH of said lysate to between about pH 12 and about pH 13;
    (d) neutralizing the alkaline-shifted cell lysate to approximately the pH of the lysis buffer;
    (e) clarifying the cell lysate of step (d) by flocculating host cell debris with the addition of PEG wherein said PEG is at a concentration which does not precipitate said supercoiled plasmid DNA;
    (f) removing said flocculated host cell debris, generating a clarified lysate containing the supercoiled plasmid DNA;
    (g) selectively precipitating the supercoiled plasmid DNA with a hexadecyltrimethylammonium bromide-induced precipitation;
    (h) redissolving the supercoiled plasmid DNA and adsorbing impurities in a well defined buffer of optimized ionic strength and further containing hydrated, crystallized calcium silicate;
    (i) adsorbing remaining impurities with a second hydrated, crystallized calcium silicate-induced adsorption;
    (j) precipitating the supercoiled plasmid DNA with PEG;
    (k) concentrating the precipitated, supercoiled plasmid DNA by microfiltration under a tangential flow filtration mode;
    (l) partially dehydrating the precipitated, supercoiled plasmid DNA with addition of ethanol;
    (m) concentrating the dehydrated supercoiled plasmid DNA a stirred-cell filter dryer; and,
    (n) drying to remove ethanol.

22. A method of claim 21, wherein said microbial cells are lysed in a standard STET buffer.

23. A method of claim 21, wherein a low-cut hexadecyltrimethylammonium bromide-induced precipitation step between steps (e) and (f) is added to precipitate debris and non-supercoiled plasmid, further clarifying the cell lysate.

* * * * *